(12) United States Patent
Tamura et al.

(10) Patent No.: US 8,642,141 B2
(45) Date of Patent: Feb. 4, 2014

(54) LIQUID CRYSTAL COMPOSITION, LIQUID CRYSTAL ELEMENT, AND LIQUID CRYSTAL DISPLAY DEVICE

(75) Inventors: Tomohiro Tamura, Okinawa (JP); Yasuhiro Niikura, Kanagawa (JP); Tetsuji Ishitani, Kanagawa (JP); Sachiko Kawakami, Kanagawa (JP); Yuko Kawata, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 13/543,695

(22) Filed: Jul. 6, 2012

(65) Prior Publication Data

US 2013/0009094 A1    Jan. 10, 2013

(30) Foreign Application Priority Data

Jul. 8, 2011    (JP) ................. 2011-151598

(51) Int. Cl.
    C09K 19/54    (2006.01)
    C09K 19/52    (2006.01)
    C09K 19/58    (2006.01)
(52) U.S. Cl.
    USPC ............. 428/1.1; 252/299.01; 252/299.5
(58) Field of Classification Search
    CPC ............. C09K 19/542; C09K 19/588
    USPC ............. 428/1.1; 252/299.01, 299.5
    See application file for complete search history.

(56) References Cited

U.S. PATENT DOCUMENTS

| | | | |
|---|---|---|---|
| 7,342,632 B2 | 3/2008 | Miyachi et al. | |
| 7,576,829 B2 | 8/2009 | Kikuchi et al. | |
| 7,648,647 B2 | 1/2010 | Kikuchi et al. | |
| 7,794,621 B2 | 9/2010 | Schott et al. | |
| 2009/0267025 A1 | 10/2009 | Schott et al. | |
| 2010/0195028 A1 | 8/2010 | Kubota et al. | |
| 2010/0258763 A1 | 10/2010 | Schott et al. | |
| 2011/0069245 A1 | 3/2011 | Haseba et al. | |
| 2012/0012785 A1 | 1/2012 | Schott et al. | |
| 2013/0134353 A1* | 5/2013 | Kato et al. | ............. 252/299.01 |

FOREIGN PATENT DOCUMENTS

| | | |
|---|---|---|
| CN | 101080480 | 11/2007 |
| CN | 102007197 | 4/2011 |
| DE | 10 2008 051 260 A1 | 4/2010 |
| EP | 2 302 015 A1 | 3/2011 |
| JP | 2006-348226 | 12/2006 |
| JP | 2008-524347 | 7/2008 |
| JP | 2008-303381 | 12/2008 |
| JP | 2009-057459 | 3/2009 |
| KR | 2007-0087610 | 8/2007 |
| WO | WO 2005-090520 A1 | 9/2005 |
| WO | WO-2006-063662 | 6/2006 |
| WO | WO-2009/139330 A1 | 11/2009 |

OTHER PUBLICATIONS

CAPLUS 2010:468733.*
English translation by machine for DE 102008051260, 2008.*
Kuball.H et al., "174. TADDOLs with Unprecedented Helical Twisting Power in Liquid Crystals,", Helvetica Chimica Acta, 1997, vol. 80, No. 8, pp. 2507-2514.
International Search Report (Application No. PCT/JP2012/066836; PCT15521) Dated Sep. 18, 2012.
Written Opinion (Application No. PCT/JP2012/066836; PCT15521) Dated Sep. 18, 2012.
M. Bauer et al., "Evaluation of Chiral Dopants for LCD Applications", Journal of the SID, vol. 14, No. 9, pp. 805-812 (2006).

* cited by examiner

*Primary Examiner* — Shean C Wu
(74) *Attorney, Agent, or Firm* — Nixon Peabody LLP; Jeffrey L. Costellia

(57) ABSTRACT

A liquid crystal composition including a dioxolane compound represented by the general formula (G1) as a chiral agent is provided. In the general formula (G1), $R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent; $R^1$ and $R^2$ may be bonded to each other to form a ring; $R^3$ and $R^4$ individually represent any of hydrogen, an alkyl group having 1 to 6 carbon atoms, and a cycloalkyl group; and $R^5$ to $R^{40}$ individually represent any of hydrogen, an alkyl group having 1 to 4 carbon atoms, an alkoxy group having 1 to 4 carbon atoms, and an aryl group having 6 to 12 carbon atoms.

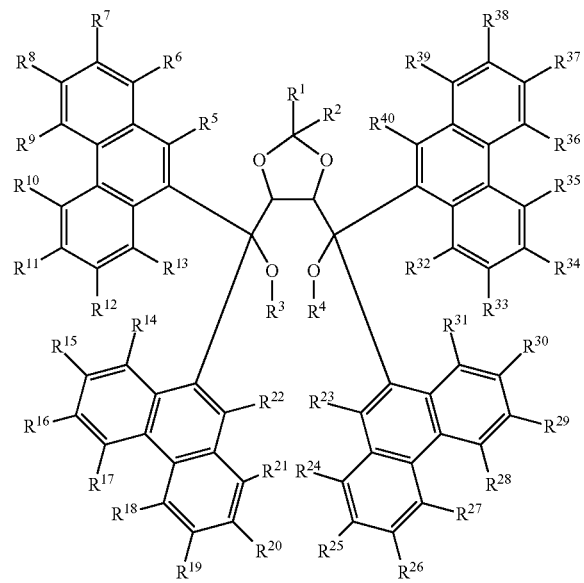

(G1)

24 Claims, 8 Drawing Sheets

LIQUID CRYSTAL COMPOSITION, LIQUID CRYSTAL ELEMENT, AND LIQUID CRYSTAL DISPLAY DEVICE

TECHNICAL FIELD

The present invention relates to a liquid crystal composition, a liquid crystal element, and a liquid crystal display device, and manufacturing methods thereof.

BACKGROUND ART

In recent years, liquid crystal has been applied to a variety of devices; in particular, a liquid crystal display device (liquid crystal display) having advantages of thinness and lightness has been used for displays in a wide range of fields.

For a larger and higher-resolution display screen, shorter response time of liquid crystal has been required, and development thereof has been advanced (for example, see Patent Document 1).

As a display mode of liquid crystal capable of quick response, a display mode using liquid crystal exhibiting a blue phase is given. The mode using liquid crystal exhibiting a blue phase achieves quick response, does not require an alignment film, and provides a wide viewing angle, and thus has been developed more actively for practical use (for example, see Patent Document 2).

REFERENCE

[Patent Document]
[Patent Document 1] Japanese Published Patent Application no. 2008-303381
[Patent Document 2] PCT International Publication no. 2005-090520

DISCLOSURE OF INVENTION

An object is to provide a novel liquid crystal composition that can be used for a variety of liquid crystal devices.

Another object is to achieve a reduction in driving voltage of a liquid crystal element and a reduction in power consumption of a liquid crystal display device with the use of the novel liquid crystal composition.

One embodiment of the present invention provides a liquid crystal composition including a dioxolane compound represented by the general formula (G1) as a chiral agent.

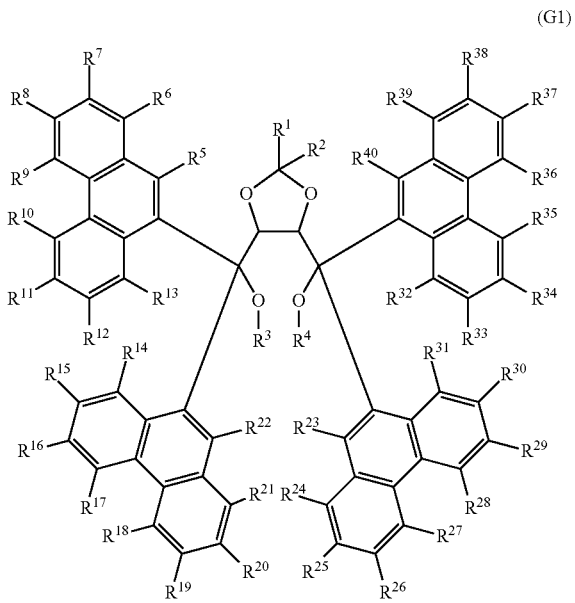

(G1)

In the general formula (G1), $R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent; $R^1$ and $R^2$ may be bonded to each other to form a ring; $R^3$ and $R^4$ individually represent any of hydrogen, an alkyl group having 1 to 6 carbon atoms, and a cycloalkyl group; and $R^5$ to $R^{40}$ individually represent any of hydrogen, an alkyl group having 1 to 4 carbon atoms, an alkoxy group having 1 to 4 carbon atoms, and an aryl group having 6 to 12 carbon atoms.

According to one embodiment of the present invention, a liquid crystal composition exhibiting a blue phase is provided as the above liquid crystal composition.

A blue phase is exhibited in a liquid crystal composition having strong twisting power and the structure of the liquid crystal composition has a double twist structure. The liquid crystal composition shows a cholesteric phase, a cholesteric blue phase, an isotropic phase, or the like depending on conditions.

A cholesteric blue phase which is a blue phase includes three structures of blue phase I, blue phase II, and blue phase III from the low temperature side. A cholesteric blue phase which is a blue phase is optically isotropic, and blue phase I and blue phase II have body-centered cubic symmetry and simple cubic symmetry, respectively. In the cases of blue phase I and blue phase II, Bragg diffraction is seen in the range from ultraviolet light to visible light.

As the indicators of the strength of twisting power, the helical pitch, the selective reflection wavelength, HTP (helical twisting power), and the diffracted wavelength are given, and among them, the helical pitch, the selective reflection wavelength, and HTP are used for evaluation of a cholesteric phase. On the other hand, the diffracted wavelength can be used for only evaluation of a blue phase, so that it is effective for evaluation of the twisting power of a blue phase. In the reflectance spectrum of a liquid crystal composition measured within the temperature range where the liquid crystal composition exhibits a blue phase, as the diffracted wavelength is on the shorter wavelength side, the liquid crystal composition has a smaller crystal lattice of a blue phase and stronger twisting power.

When the twisting power of the liquid crystal composition is strong, the transmittance of the liquid crystal composition in application of no voltage (at an applied voltage of 0 V) can be low, leading to a higher contrast of a liquid crystal display device including the liquid crystal composition.

The chiral agent is used to induce twisting of the liquid crystal composition, align the liquid crystal composition in a helical structure, and make the liquid crystal composition exhibit a blue phase. For the chiral agent, a compound which has an asymmetric center, high compatibility with the liquid crystal composition, and strong twisting power is used. In addition, the chiral agent is an optically active substance; a higher optical purity is better and the most preferable optical purity is 99% or higher.

Since the dioxolane compound represented by the general formula (G1) is a chiral agent with a strong twisting power, the proportion of the dioxolane compound, which serves as a chiral agent, in a liquid crystal composition can be 7 wt % or lower. When a large amount of chiral agent is added to improve the twisting power of the liquid crystal composition, driving voltage applied to drive the liquid crystal composition might increase. As in the liquid crystal composition, reduction in the amount of chiral agent to be added allows decrease in driving voltage, resulting in lower power consumption.

One embodiment of the present invention provides a liquid crystal composition which includes the dioxolane compound represented by the general formula (G1) and a nematic liquid crystal and exhibits a blue phase.

(G1)

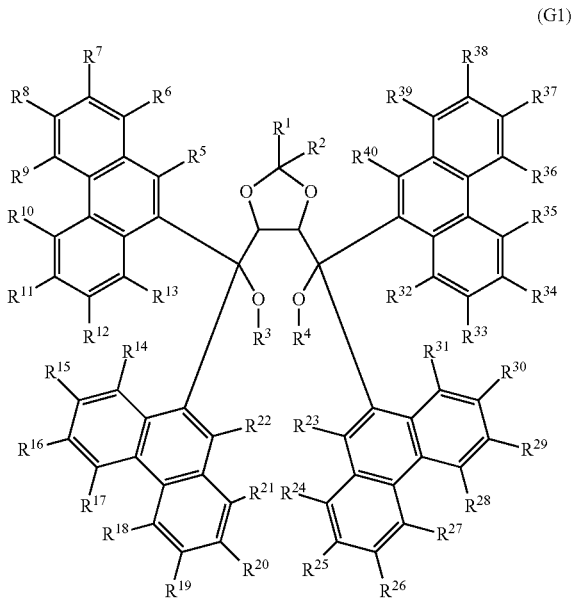

In the general formula (G1), $R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent; $R^1$ and $R^2$ may be bonded to each other to form a ring; $R^3$ and $R^4$ individually represent any of hydrogen, an alkyl group having 1 to 6 carbon atoms, and a cycloalkyl group; and $R^5$ to $R^{40}$ individually represent any of hydrogen, an alkyl group having 1 to 4 carbon atoms, an alkoxy group having 1 to 4 carbon atoms, and an aryl group having 6 to 12 carbon atoms.

One embodiment of the present invention provides a liquid crystal composition which includes a dioxolane compound represented by the general formula (G2) and a nematic liquid crystal and exhibits a blue phase.

(G2)

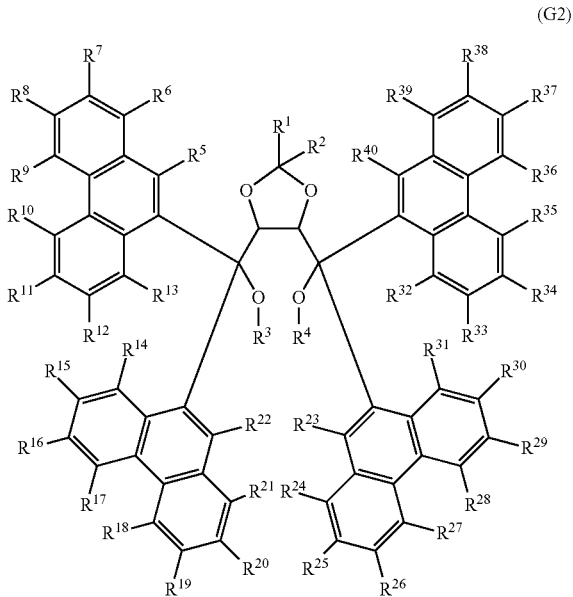

In the general formula (G2), $R^1$ and $R^2$ individually represent any of hydrogen, an alkyl group having 1 to 6 carbon atoms, a methoxy group, and a phenyl group; $R^1$ and $R^2$ may be bonded to each other to form a cyclohexyl ring; and $R^3$ to $R^{40}$ individually represent hydrogen.

One embodiment of the present invention provides a liquid crystal composition which includes a dioxolane compound represented by the structural formula (101) and a nematic liquid crystal and exhibits a blue phase.

(101)

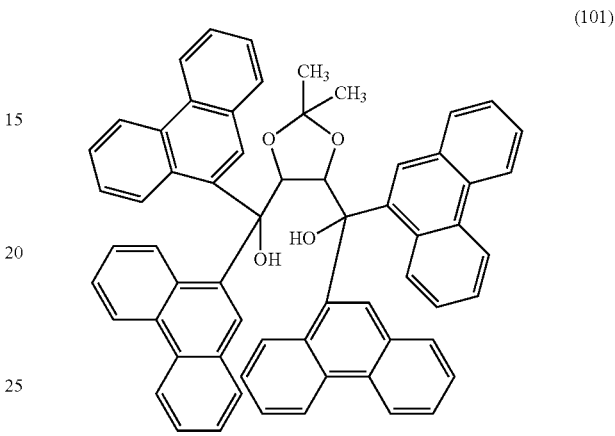

In the liquid crystal composition according to the above embodiment of the present invention, the proportion of the dioxolane compound in the liquid crystal composition is 7 wt % or lower (preferably higher than or equal to 1 wt % and lower than or equal to 7 wt %, further preferably higher than or equal to 3 wt % and lower than or equal to 6 wt %).

In the liquid crystal composition according to the above embodiment of the present invention, a peak of a diffraction wavelength on the longest wavelength side in a reflectance spectrum is less than or equal to 700 nm (preferably less than or equal to 420 nm).

One embodiment of the present invention provides a liquid crystal element, a liquid crystal display device, or an electronic apparatus in which the above liquid crystal composition is used.

According to one embodiment of the present invention, a novel liquid crystal composition which includes the dioxolane compound represented by the general formula (G1) as a chiral agent and a nematic liquid crystal and exhibits a blue phase can be provided.

According to one embodiment of the present invention, a liquid crystal element, a liquid crystal display device, or an electronic apparatus with lower driving voltage and lower power consumption can be provided with the use of the liquid crystal composition.

BRIEF DESCRIPTION OF DRAWINGS

In the accompanying drawings:
FIGS. 4A1, 4A2, and 4B are views illustrating a liquid crystal display module.

BEST MODE FOR CARRYING OUT THE INVENTION

Figure 1A:
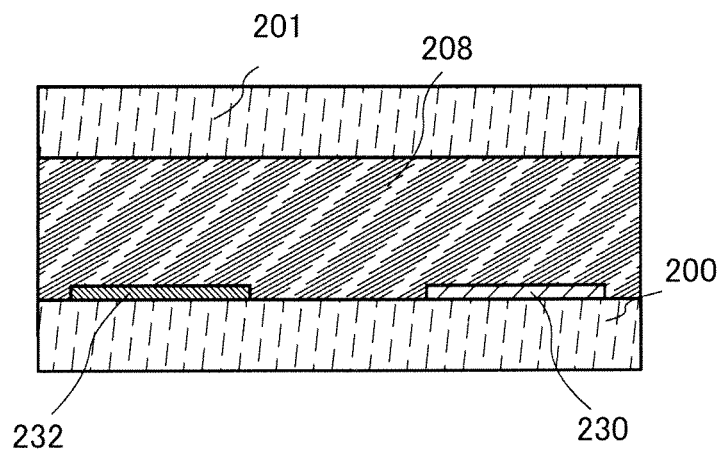
FIGS. 1A and 1B each show an example of a liquid crystal element and a liquid crystal display device.

Embodiments and Examples of the present invention will be described in detail with reference to the accompanying drawings. Note that the present invention is not limited to the following description, and it will be easily understood by those skilled in the art that modes and details can be modified in various ways without departing from the spirit and scope of the present invention. Therefore, the present invention should not be construed as being limited to the description in the following embodiments and examples. In the structures described below, the same portions or portions having similar functions are denoted by the same reference numerals in different drawings, and explanation thereof will not be repeated.

Note that the ordinal numbers such as "first", "second", and "third" in this specification are used for convenience and do not denote the order of steps and the stacking order of layers. In addition, the ordinal numbers in this specification do not denote particular names which specify the present invention.

Embodiment 1

Figure 1B:
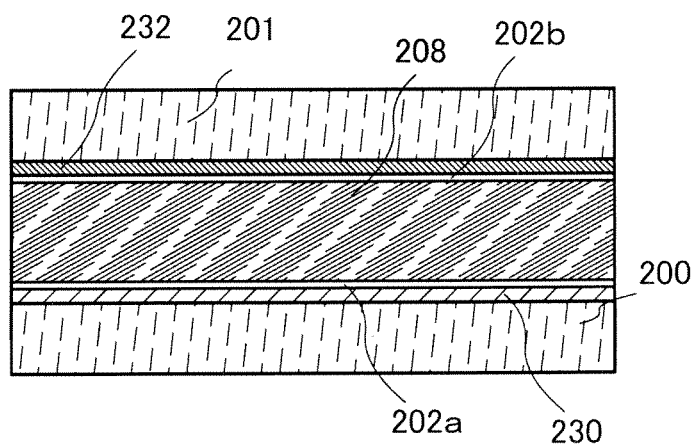

A liquid crystal composition according to one embodiment of the present invention, a liquid crystal element, and a liquid crystal display device including the liquid crystal composition will be described with reference to FIGS. 1A and 1B. FIGS. 1A and 1B are each a cross-sectional view of a liquid crystal element and a liquid crystal display device.

A liquid crystal composition according to one embodiment of the present invention is a liquid crystal composition including the dioxolane compound represented by the general formula (G1) as a chiral agent.

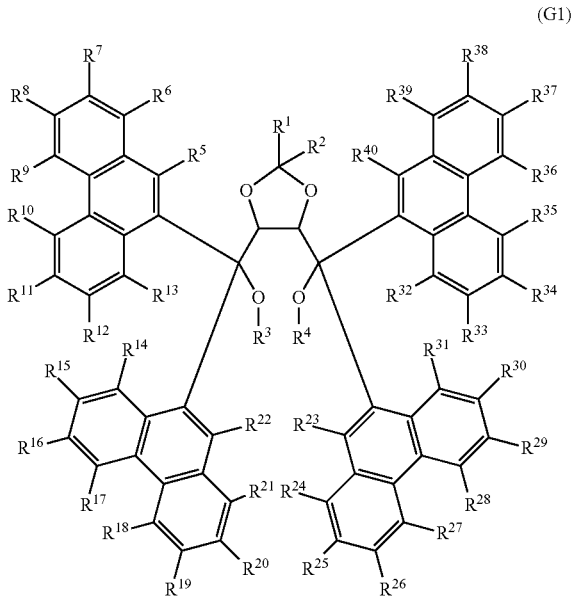

(G1)

In the general formula (G1), $R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent; $R^1$ and $R^2$ may be bonded to each other to form a ring; $R^3$ and $R^4$ individually represent any of hydrogen, an alkyl group having 1 to 6 carbon atoms, and a cycloalkyl group; and $R^5$ to $R^{40}$ individually represent any of hydrogen, an alkyl group having 1 to 4 carbon atoms, an alkoxy group having 1 to 4 carbon atoms, and an aryl group having 6 to 12 carbon atoms.

According to one embodiment of the present invention, a liquid crystal composition exhibiting a blue phase is provided as the above liquid crystal composition.

When the twisting power of the liquid crystal composition is strong, the transmittance of the liquid crystal composition in application of no voltage (at an applied voltage of 0 V) can be low, leading to a higher contrast of a liquid crystal display device including the liquid crystal composition.

The chiral agent is used to induce twisting of the liquid crystal composition, align the liquid crystal composition in a helical structure, and make the liquid crystal composition exhibit a blue phase. For the chiral agent, a compound which has an asymmetric center, high compatibility with the liquid crystal composition, and strong twisting power is used. In addition, the chiral agent is an optically active substance; a higher optical purity is better and the most preferable optical purity is 99% or higher.

Since the dioxolane compound represented by the general formula (G1) is a chiral agent with a strong twisting power, the proportion of the dioxolane compound, which serves as a chiral agent, in a liquid crystal composition can be 7 wt % or lower (preferably higher than or equal to 1 wt % and lower than or equal to 7 wt %, further preferably higher than or equal to 3 wt % and lower than or equal to 6 wt %). When a large amount of chiral agent is added to improve the twisting power of the liquid crystal composition, driving voltage applied to drive the liquid crystal composition might increase. As in the liquid crystal composition, reduction in the amount of chiral agent to be added allows decrease in driving voltage, resulting in lower power consumption.

In the liquid crystal composition according to the above embodiment of the present invention, a peak of a diffraction wavelength on the longest wavelength side in a reflectance spectrum can be less than or equal to 700 nm (preferably less than or equal to 420 nm).

A liquid crystal composition according to one embodiment of the present invention is a liquid crystal composition including the dioxolane compound represented by the general formula (G1) and a nematic liquid crystal and exhibiting a blue phase.

(G1)

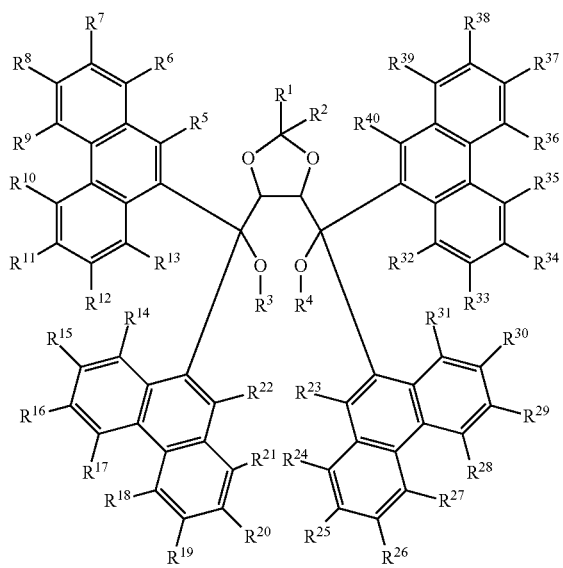

In the general formula (G1), $R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent; $R^1$ and $R^2$ may be bonded to each other to form a ring; $R^3$ and $R^4$ individually represent any of hydrogen, an alkyl group having 1 to 6 carbon atoms, and a cycloalkyl group; and $R^5$ to $R^{40}$ individually represent any of hydrogen, an alkyl group having 1 to 4 carbon atoms, an alkoxy group having 1 to 4 carbon atoms, and an aryl group having 6 to 12 carbon atoms.

A liquid crystal composition according to one embodiment of the present invention is a liquid crystal composition including the dioxolane compound represented by the general formula (G2) and a nematic liquid crystal and exhibiting a blue phase.

(G2)

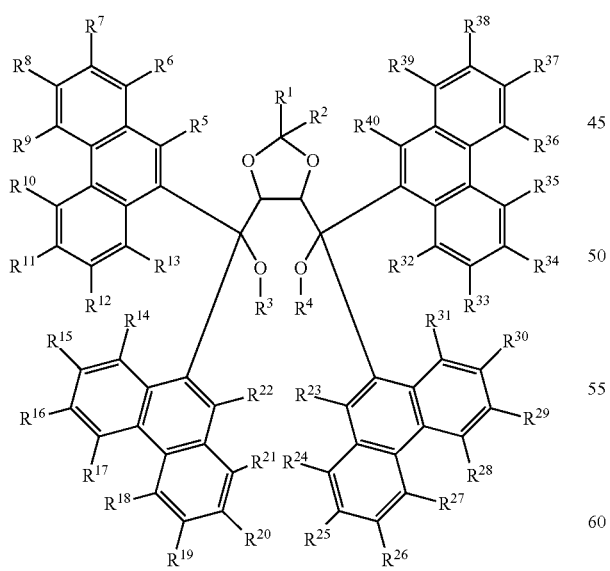

In the general formula (G2), $R^1$ and $R^2$ individually represent any of hydrogen, an alkyl group having 1 to 6 carbon atoms, a methoxy group, and a phenyl group; $R^1$ and $R^2$ may be bonded to each other to form a cyclohexyl ring; and $R^3$ to $R^{40}$ individually represent hydrogen.

Specific examples of the dioxolane compound represented by general formula (G1) include dioxolane compounds represented by the structural formulae (100) to (105) and (110) to (115). Note that the present invention is not limited to these.

(100)

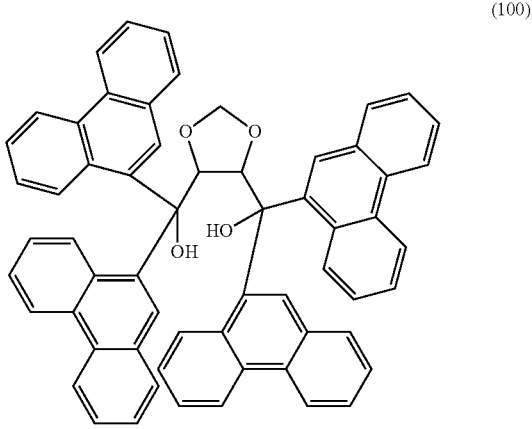

(101)

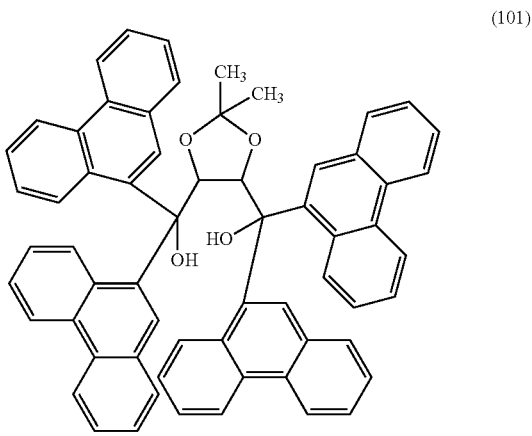 [SMILES: CC1(C)OC(C(O)(c2cc3ccccc3c3ccccc23)c2cc3ccccc3c3ccccc23)C(C(O)(c2cc3ccccc3c3ccccc23)c2cc3ccccc3c3ccccc23)O1]

(102)

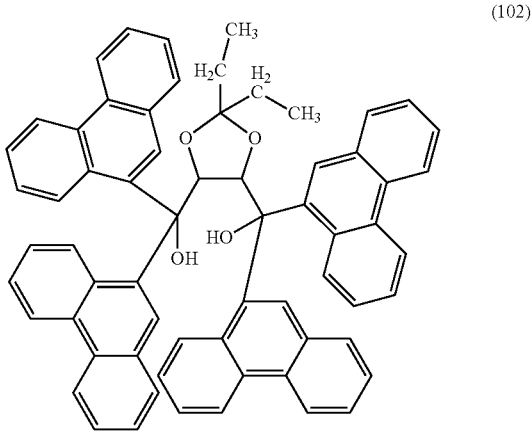

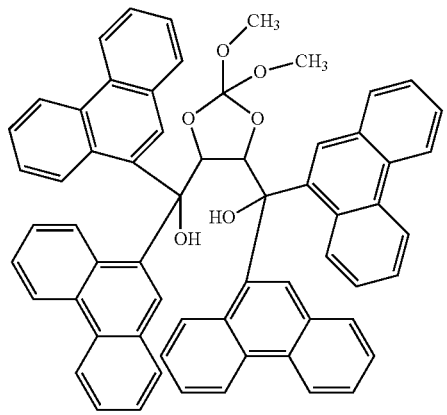
(103)
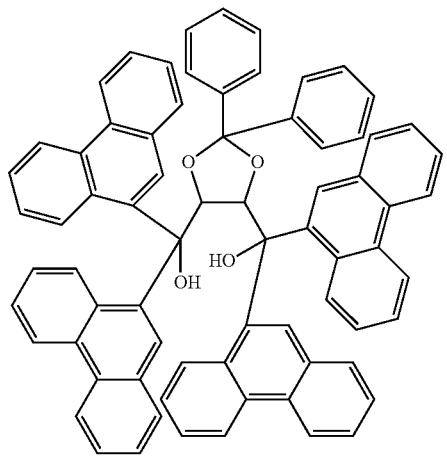
(104)
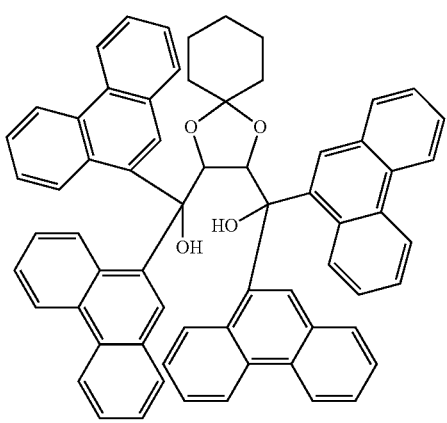
(105)
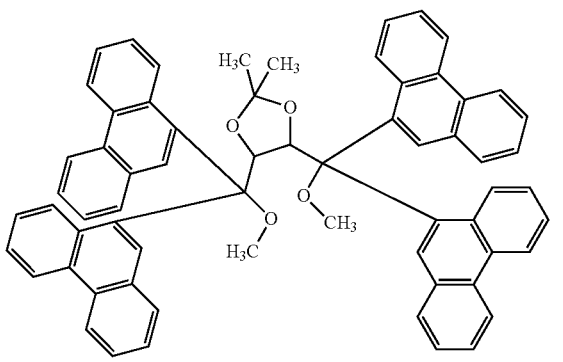
(110)
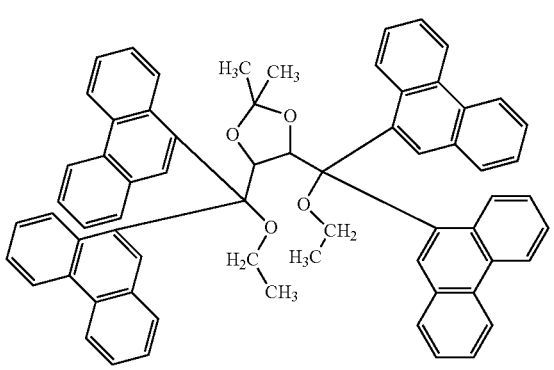
(111)
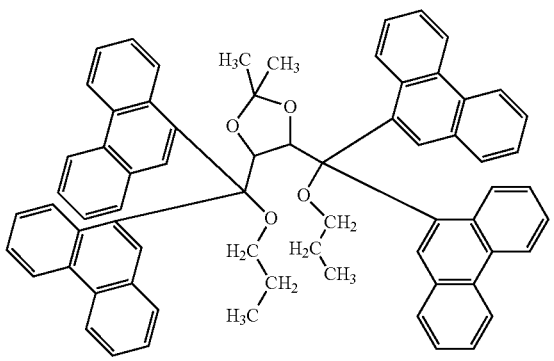
(112)

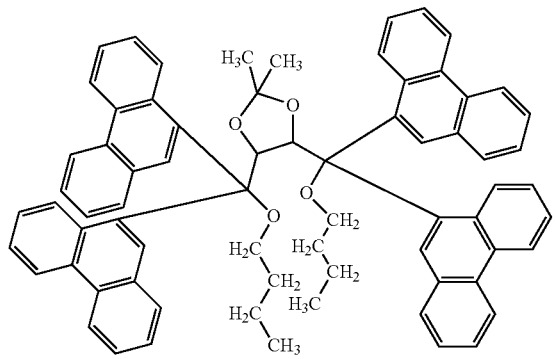

(113)

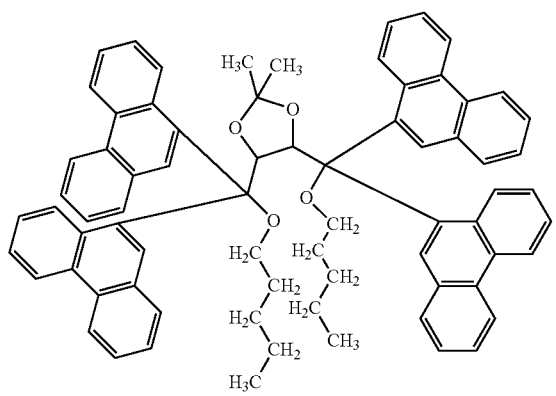

(114)

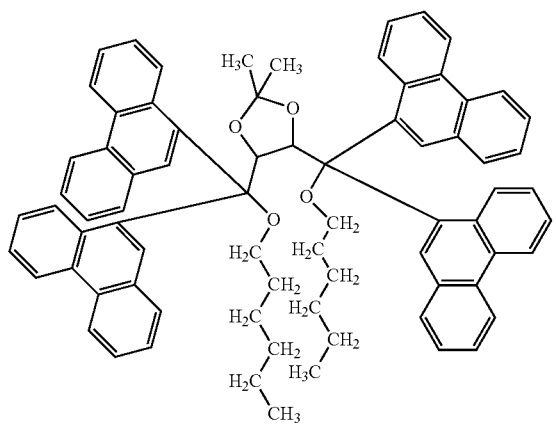

(115)

A variety of reactions can be applied to a synthesis method of the dioxolane compound which is represented by the general formula (G1) and included in the liquid crystal composition according to one embodiment of the present invention. For example, through synthesis reactions shown in the following synthesis schemes (K-1) and (K-2), the dioxolane compound which is represented by the general formula (G1) and included in the liquid crystal composition according to one embodiment of the present invention can be synthesized. Note that the synthesis method of the dioxolane compound represented by the general formula (G1) according to one embodiment of the present invention is not limited to the following synthesis method.

A synthesis method of the compound represented by the following general formula (G1) is described.

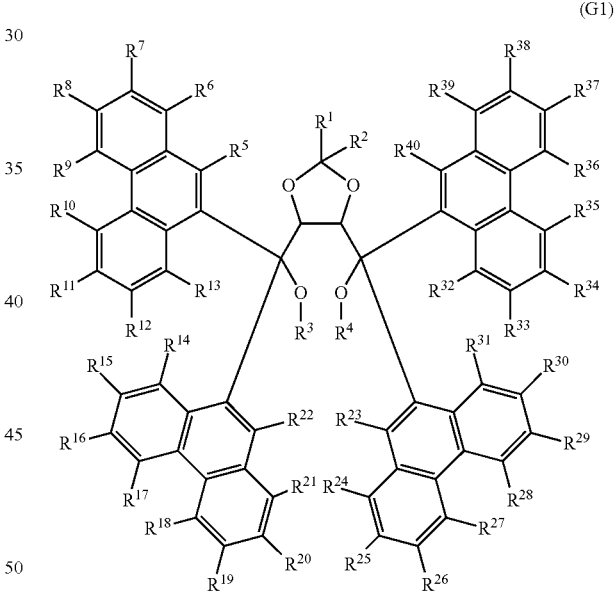

(G1)

A synthesis method in the case where in the general formula (G1), α, β, γ, and δ each representing a phenanthrene skeleton have the following relation α=β=γ=δ is described. In the case where the general formula (G1) has the relation α=β=γ=δ, the general formula (G1) is represented by the following general formula (G1-1).

(G1)
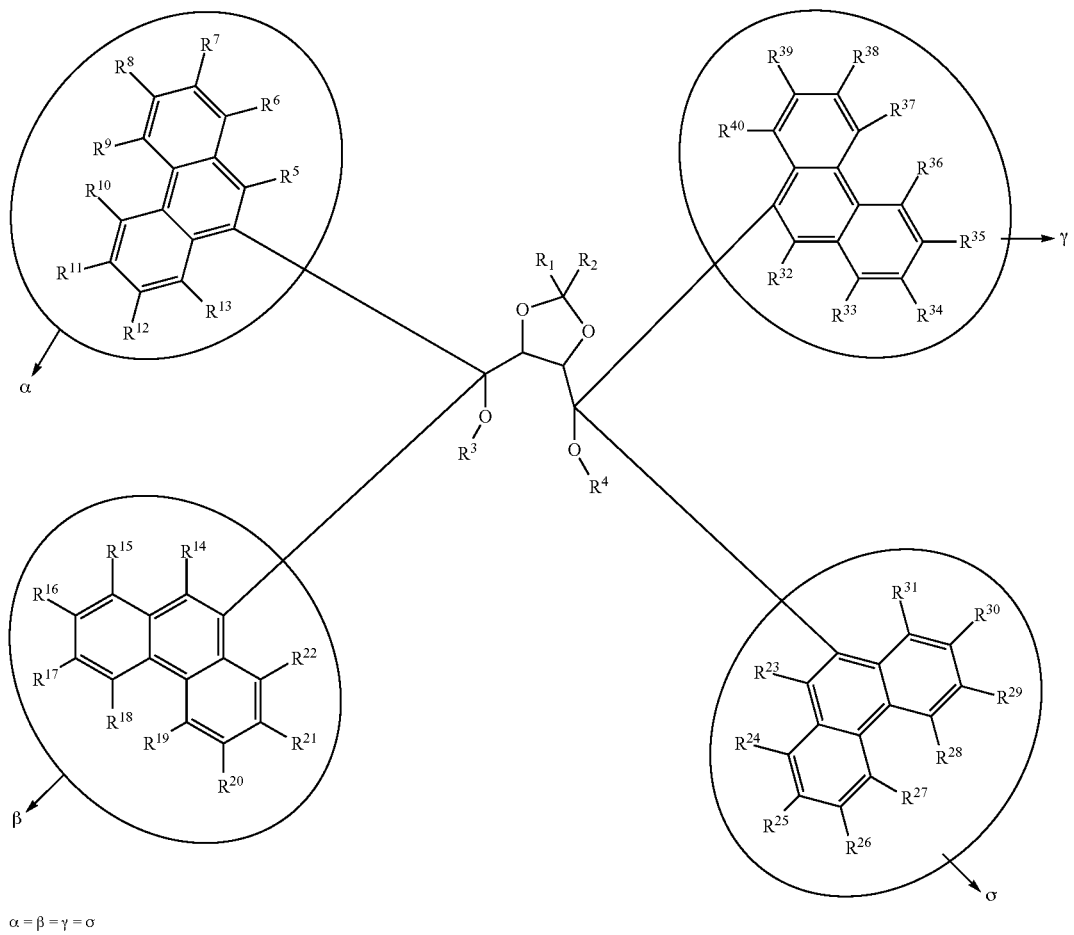
α = β = γ = σ
(G1-1)
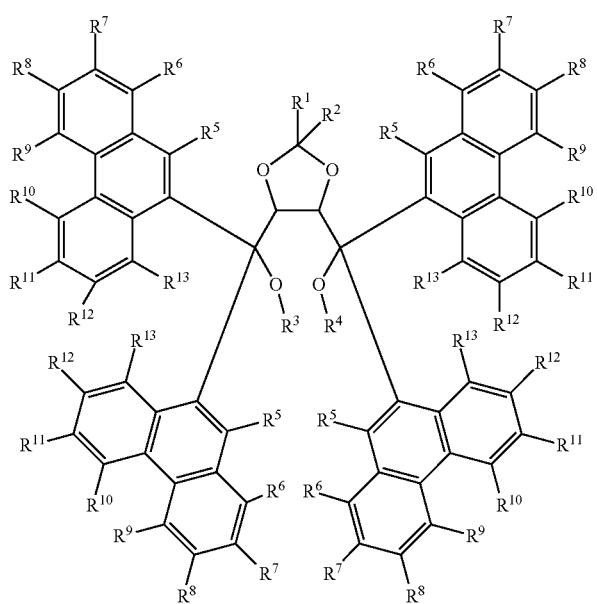

A synthesis method of a compound represented by the general formula (G1-1) is described.

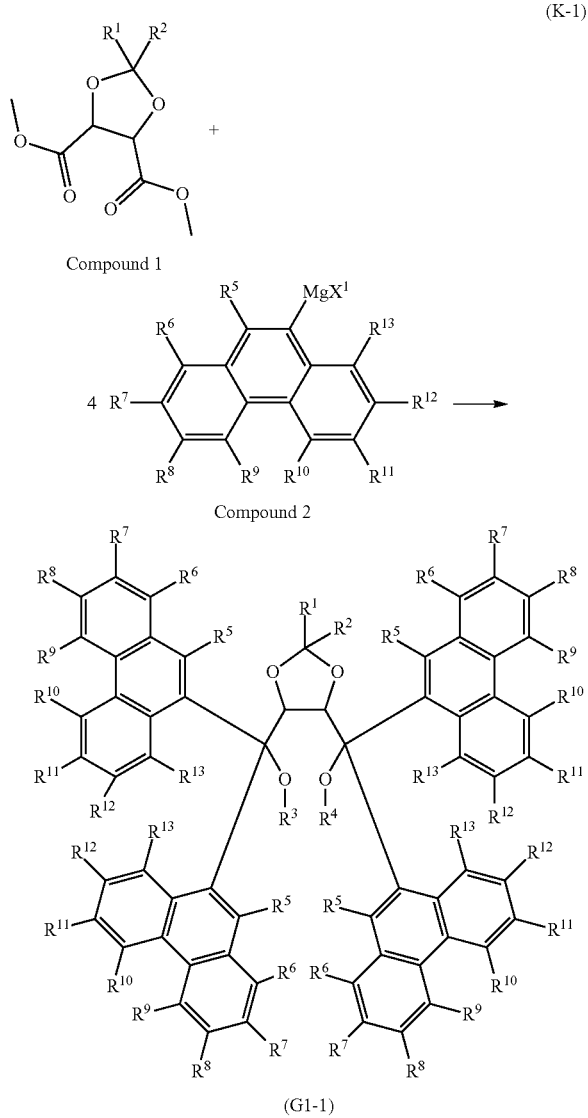

By making a compound having 1,3-dioxolane-4,5-dicarboxylic acid skeleton (Compound 1) react with four equivalents of Grignard reagent (Compound 2) which is a compound having a phenanthrene skeleton, a dioxolane compound (the general formula (G1-1)), which is a target substance, can be obtained (the reaction formula (K-1)).

In the reaction formula (K-1), $R^1$ and $R^2$ individually represent any of hydrogen, an alkyl group having 1 to 6 carbon atoms, an alkoxy group having 1 to 6 carbon atoms, and an aryl group having 6 to 12 carbon atoms; and $R^1$ and $R^2$ may be bonded to each other to form a ring. In the reaction formula (K-1), $R^3$ and $R^4$ represent hydrogen. An alkoxy group may be substituted for a hydroxyl group of a diol (the general formula (G1-1)) obtained by the reaction formula (K-1) by Williamson ether synthesis reaction or the like. In that case, $R^3$ and $R^4$ individually represent an alkyl group having 1 to 6 carbon atoms or a cycloalkyl group. In the reaction formula (K-1), $R^5$ to $R^{13}$ individually represent any of hydrogen, an alkyl group having 1 to 4 carbon atoms, an alkoxy group having 1 to 4 carbon atoms, and an aryl group having 6 to 12 carbon atoms.

In the reaction formula (K-1), a similar reaction can occur when instead of the Grignard reagent, a reagent having nucleophilicity such as a lithiation substance is used as the compound having a phenanthrene skeleton, whereby the compound represented by the general formula (G1-1) can be synthesized.

Furthermore, the compound represented by the general formula (G1) can be synthesized by making Compound 1 react with four equivalents of the compound having a phenanthrene skeleton one by one in four steps (the reaction formula (K-2)).

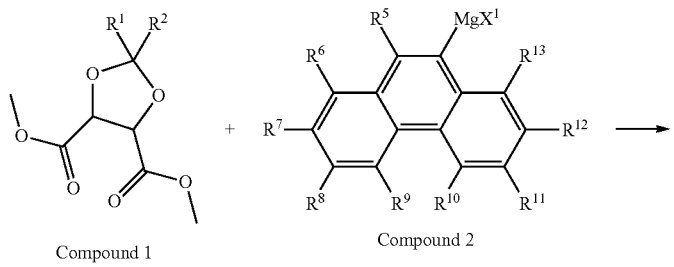

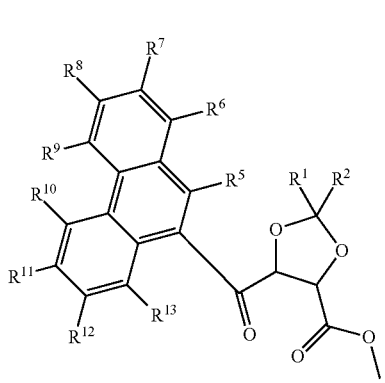 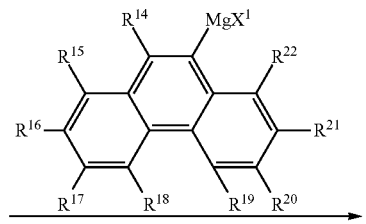
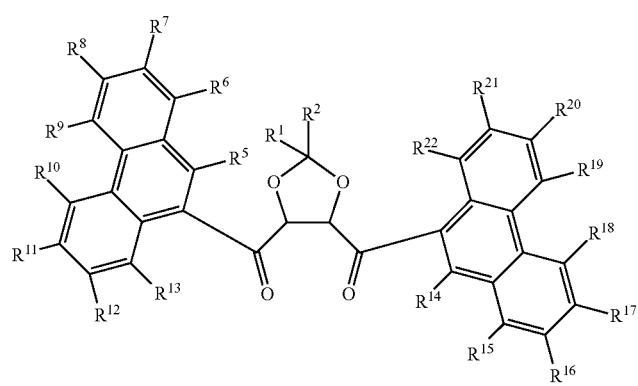 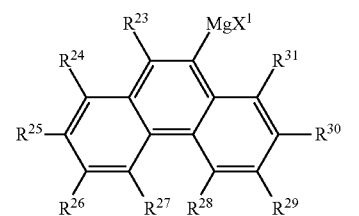
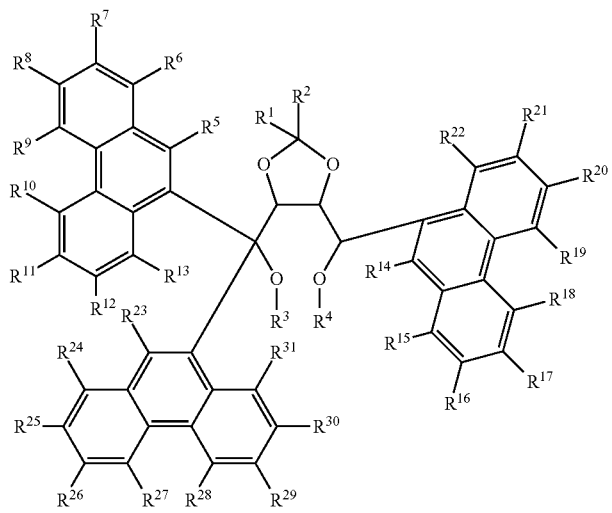 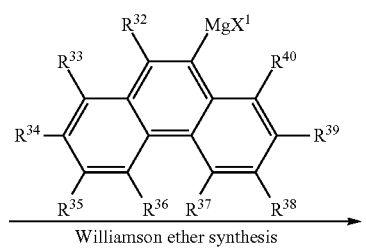
Williamson ether synthesis -continued

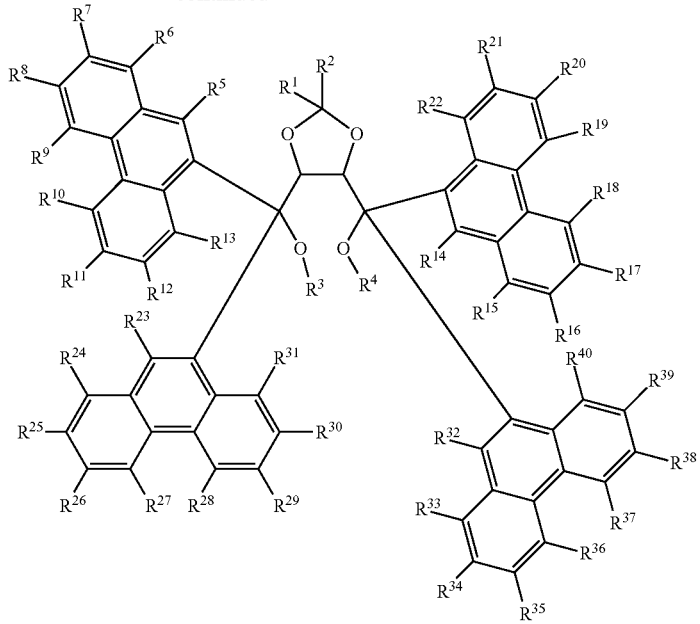

(G1)

In the above manner, the dioxolane compound which is represented by the general formula (G1) and included in the liquid crystal composition according to one embodiment of the present invention can be synthesized. The dioxolane compound represented by the general formula (G1) can be used as a chiral agent.

The nematic liquid crystal is not particularly limited, and examples thereof are a biphenyl-based compound, a terphenyl-based compound, a phenylcyclohexyl-based compound, a biphenylcyclohexyl-based compound, a phenylbicyclohexyl-based compound, a benzoic acid phenyl-based compound, a cyclohexyl benzoic acid phenyl-based compound, a phenyl benzoic acid phenyl-based compound, a bicyclohexyl carboxylic acid phenyl-based compound, an azomethine-based compound, an azo-based compound, an azoxy-based compound, a stilbene-based compound, a bicyclohexyl-based compound, a phenylpyrimidine-based compound, a biphenylpyrimidine-based compound, a pyrimidine-based compound, and a biphenyl ethyne-based compound.

A blue phase is optically isotropic and thus has no viewing angle dependence. Consequently, an alignment film is not necessarily formed; therefore, display image quality can be improved and cost can be reduced.

In a liquid crystal display device, it is preferable that a polymerizable monomer be added to a liquid crystal composition and polymer stabilization treatment be performed in order to broaden the temperature range within which a blue phase is exhibited. As the polymerizable monomer, for example, a thermopolymerizable (thermosetting) monomer which can be polymerized by heat, a photopolymerizable (photocurable) monomer which can be polymerized by light, or a polymerizable monomer which can be polymerized by heat and light can be used. Further, a polymerization initiator may be added to the liquid crystal composition.

The polymerizable monomer may be a monofunctional monomer such as acrylate or methacrylate; a polyfunctional monomer such as diacrylate, triacrylate, dimethacrylate, or trimethacrylate; or a mixture thereof. Further, the polymerizable monomer may have liquid crystallinity, non-liquid crystallinity, or both of them.

As the polymerization initiator, a radical polymerization initiator which generates radicals by light irradiation, an acid generator which generates an acid by light irradiation, or a base generator which generates a base by light irradiation may be used.

For example, polymer stabilization treatment can be performed in such a manner that a photopolymerizable monomer and a photopolymerization initiator are added to the liquid crystal composition and the liquid crystal composition is irradiated with light having a wavelength at which the photopolymerizable monomer and the photopolymerization initiator react with each other. As the photopolymerizable monomer, typically, a UV polymerizable monomer can be used. When a UV-polymerizable monomer is used as a photopolymerizable monomer, the liquid crystal composition may be irradiated with ultraviolet light.

This polymer stabilization treatment may be performed on a liquid crystal composition exhibiting an isotropic phase or a liquid crystal composition exhibiting a blue phase under the control of the temperature. Note that a temperature at which the phase changes from a blue phase to an isotropic phase when the temperature rises, or a temperature at which the phase changes from an isotropic phase to a blue phase when the temperature falls is referred to as the phase transition temperature between a blue phase and an isotropic phase. For example, the polymer stabilization treatment can be performed in the following manner: after a liquid crystal composition to which a photopolymerizable monomer is added is heated to exhibit an isotropic phase, the temperature of the liquid crystal composition is gradually lowered so that the phase changes to a blue phase, and then, light irradiation is performed while the temperature at which a blue phase is exhibited is kept.

FIGS. 1A and 1B each illustrate an example of a liquid crystal element and a liquid crystal display device according to one embodiment of the present invention.

A liquid crystal element according to one embodiment of the present invention includes at least, between a pair of electrode layers (a pixel electrode layer 230 and a common electrode layer 232 having different potentials), a liquid crystal composition 208 including the dioxolane compound represented by the general formula (G1) and a nematic liquid crystal.

FIGS. 1A and 1B each illustrate a liquid crystal element and a liquid crystal display device in which the liquid crystal composition 208 including the dioxolane compound represented by the general formula (G1) and a nematic liquid crystal is provided between a first substrate 200 and a second substrate 201. A difference between the liquid crystal element and the liquid crystal display device in FIG. 1A and those in FIG. 1B is positions of the pixel electrode layer 230 and the common electrode layer 232 with respect to the liquid crystal composition 208.

In the liquid crystal element and the liquid crystal display device illustrated in FIG. 1A, the pixel electrode layer 230 and the common electrode layer 232 are adjacently provided between the first substrate 200 and the liquid crystal composition 208. With the structure in FIG. 1A, a method in which the gray scale is controlled by generating an electric field substantially parallel (i.e., in the lateral direction) to a substrate to move liquid crystal molecules in a plane parallel to the substrate can be used.

The structure in FIG. 1A can be favorably applied to the case where the liquid crystal composition including the dioxolane compound represented by the general formula (G1) and a nematic liquid crystal and exhibiting a blue phase, which is a liquid crystal composition according to one embodiment of the present invention, is used as the liquid crystal composition 208. The liquid crystal composition provided as the liquid crystal composition 208 may contain an organic resin.

With an electric field generated between the pixel electrode layer 230 and the common electrode layer 232, liquid crystal is controlled. An electric field in the lateral direction is applied to the liquid crystal, so that liquid crystal molecules can be controlled by the electric field. The liquid crystal composition exhibiting a blue phase is capable of quick response. Thus, a high-performance liquid crystal element and a high-performance liquid crystal display device can be achieved.

For example, such a liquid crystal composition exhibiting a blue phase, which is capable of quick response, can be favorably used for a successive additive color mixing method (field sequential method) in which light-emitting diodes (LEDs) of RGB or the like are arranged in a backlight unit and color display is performed by time division, or a three-dimensional display method using a shutter glasses system in which images for the right eye and images for the left eye are alternately viewed by time division.

In the liquid crystal element and the liquid crystal display device illustrated in FIG. 1B, the pixel electrode layer 230 and the common electrode layer 232 are provided on the first substrate 200 side and the second substrate 201 side respectively, with the liquid crystal composition 208 interposed therebetween. With the structure in FIG. 1B, a method in which the gray scale is controlled by generating an electric field substantially perpendicular to a substrate to move liquid crystal molecules in a plane perpendicular to the substrate can be used. An alignment film 202a may be provided between the liquid crystal composition 208 and the pixel electrode layer 230 and an alignment film 202b may be provided between the liquid crystal composition 208 and the common electrode layer 232. A liquid crystal composition including the dioxolane compound represented by the general formula (G1) and a nematic liquid crystal and exhibiting a blue phase, which is a liquid crystal composition according to one embodiment of the present invention, can be used in liquid crystal elements with a variety of structures and liquid crystal display devices with a variety of display modes.

The distance between the pixel electrode layer 230 and the common electrode layer 232, which are adjacent to each other with the liquid crystal composition 208 interposed therebetween, is a distance at which liquid crystal in the liquid crystal composition 208 between the pixel electrode layer 230 and the common electrode layer 232 responds to a predetermined voltage applied to each of the pixel electrode layer 230 and the common electrode layer 232. Alternatively, the voltage applied is controlled depending on the distance as appropriate.

The maximum thickness (film thickness) of the liquid crystal composition 208 is preferably greater than or equal to 1 μm and less than or equal to 20 μm.

The liquid crystal composition 208 can be formed by a dispensing method (dropping method), or an injection method in which liquid crystal is injected using capillary action or the like after the first substrate 200 and the second substrate 201 are attached to each other.

Although not illustrated in FIGS. 1A and 1B, an optical film such as a polarizing plate, a retardation plate, or an anti-reflection film, or the like is provided as appropriate. For example, circular polarization with the polarizing plate and the retardation plate may be used. In addition, a backlight or the like can be used as a light source.

In this specification, a substrate provided with a semiconductor element (e.g., a transistor) or a common electrode layer is referred to as an element substrate (a first substrate), and a substrate which faces the element substrate with a liquid crystal composition interposed therebetween is referred to as a counter substrate (a second substrate).

As a liquid crystal display device according to one embodiment of the present invention, a transmissive liquid crystal display device in which display is performed by transmission of light from a light source, a reflective liquid crystal display device in which display is performed by reflection of incident light, or a transflective liquid crystal display device in which a transmissive type and a reflective type are combined can be provided.

In the case of the transmissive liquid crystal display device, a pixel electrode layer, a common electrode layer, a first substrate, a second substrate, and other components such as an insulating film and a conductive film, which are provided in a pixel region through which light is transmitted, have a property of transmitting light in the visible wavelength range. In the liquid crystal display device having the structure illustrated in FIG. 1A, it is preferable that the pixel electrode layer and the common electrode layer have a light-transmitting property; however, if an opening pattern is provided, a non-light-transmitting material such as a metal film may be used depending on the shape.

On the other hand, in the case of the reflective liquid crystal display device, a reflective component which reflects light transmitted through the liquid crystal composition (e.g., a reflective film or substrate) may be provided on the side opposite to the viewing side of the liquid crystal composition. Therefore, a substrate, an insulating film, and a conductive film which are provided between the viewing side and the reflective component and through which light is transmitted have a light-transmitting property with respect to light in the visible wavelength range. Note that in this specification, a light-transmitting property refers to a property of transmitting at least light in the visible wavelength range. In the liquid crystal display device having the structure illustrated in FIG. 1B, the pixel electrode layer or the common electrode layer on the side opposite to the viewing side may have a light-reflecting property so that it can be used as a reflective component.

The pixel electrode layer 230 and the common electrode layer 232 may be formed with the use of one or more of the following: indium tin oxide, a conductive material in which zinc oxide is mixed into indium oxide, a conductive material in which silicon oxide ($SiO_2$) is mixed into indium oxide, organoindium, organotin, indium oxide containing tungsten oxide, indium zinc oxide containing tungsten oxide, indium oxide containing titanium oxide, and indium tin oxide containing titanium oxide; graphene; metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

As the first substrate 200 and the second substrate 201, a glass substrate of barium borosilicate glass, aluminoborosilicate glass, or the like, a quartz substrate, a plastic substrate, or the like can be used. Note that in the case of the reflective liquid crystal display device, a metal substrate such as an aluminum substrate or a stainless steel substrate may be used as a substrate on the side opposite to the viewing side.

In the above manner, a novel liquid crystal composition which includes the dioxolane compound represented by the general formula (G1) and a nematic liquid crystal can be provided. The liquid crystal composition can exhibits a blue phase.

The use of the liquid crystal composition including the dioxolane compound represented by the general formula (G1) and a nematic liquid crystal makes it possible to provide a liquid crystal element and a liquid crystal display device with lower driving voltage. Consequently, a liquid crystal display device with lower power consumption can be provided.

This embodiment can be implemented in appropriate combination with any of the structures described in the other embodiments.

Embodiment 2

As a liquid crystal display device according to one embodiment of the present invention, a passive matrix liquid crystal display device and an active matrix liquid crystal display device can be provided. In this embodiment, an example of an active matrix liquid crystal display device according to one embodiment of the present invention will be described with reference to FIGS. 2A and 2B and FIGS. 3A to 3D.

Figure 2A:
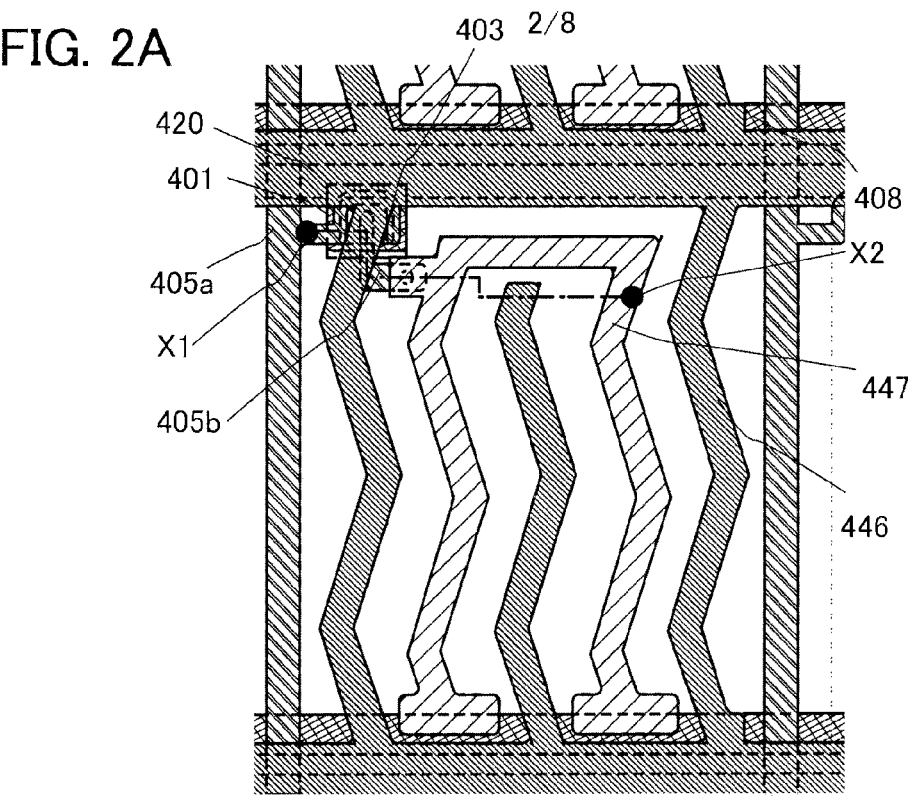
FIGS. 2A and 2B are views illustrating one mode of a liquid crystal display device.
Figure 2B:
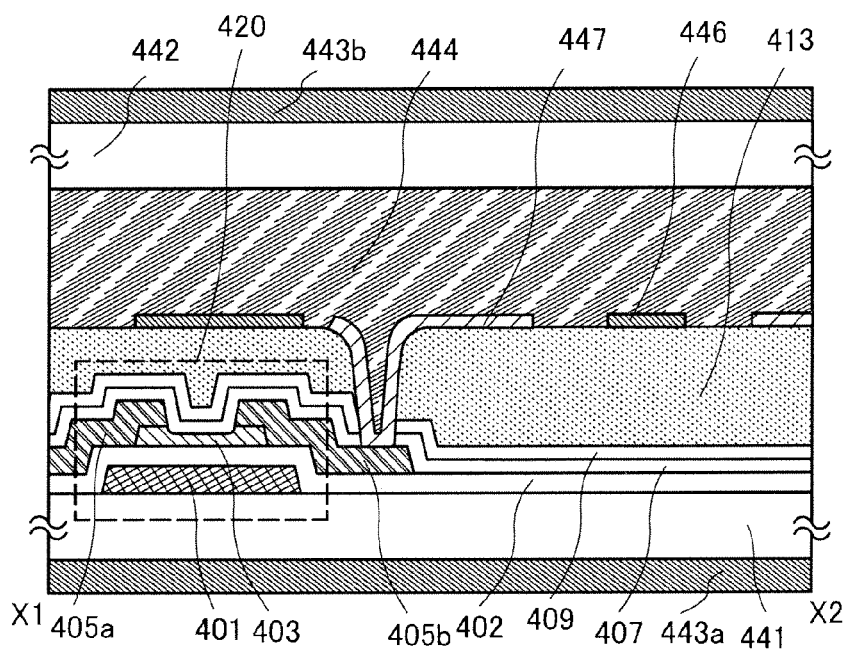

FIG. 2A is a plan view of the liquid crystal display device and illustrates one pixel. FIG. 2B is a cross-sectional view taken along line X1-X2 in FIG. 2A.

In FIG. 2A, a plurality of source wiring layers (including a wiring layer 405a) is arranged so as to be parallel to (extend in the longitudinal direction in the drawing) and apart from each other. A plurality of gate wiring layers (including a gate electrode layer 401) is arranged so as to be extended in the direction perpendicular to or substantially perpendicular to the source wiring layers (in the horizontal direction in the drawing) and apart from each other. Common wiring layers 408 are provided so as to be adjacent to the respective gate wiring layers and extended in the direction parallel to or substantially parallel to the gate wiring layers, that is, in the direction perpendicular to or substantially perpendicular to the source wiring layers (in the horizontal direction in the drawing). A roughly rectangular space is surrounded by the source wiring layers, the common wiring layer 408, and the gate wiring layer. In this space, a pixel electrode layer and a common electrode layer of the liquid crystal display device are provided. A transistor 420 for driving the pixel electrode layer is provided at the upper left corner of the drawing. A plurality of pixel electrode layers and a plurality of transistors are arranged in a matrix.

In the liquid crystal display device in FIGS. 2A and 2B, a first electrode layer 447 electrically connected to the transistor 420 serves as a pixel electrode layer, while a second electrode layer 446 electrically connected to the common wiring layer 408 serves as a common electrode layer. Note that a capacitor is formed by the first electrode layer and the common wiring layer. Although the common electrode layer can operate in a floating state (electrically isolated state), the potential of the common electrode layer may be set to a fixed potential, preferably to a potential around an intermediate potential of an image signal which is transmitted as data at such a level as not to generate flickers.

A method can be used in which the gray scale is controlled by generating an electric field parallel to or substantially parallel to a substrate (i.e., in the lateral direction) to move liquid crystal molecules in a plane parallel to the substrate. For such a method, an electrode structure used in an IPS mode illustrated in FIGS. 2A and 2B and FIGS. 3A to 3D can be employed.

In a lateral electric field mode such as an IPS mode, a first electrode layer (e.g., a pixel electrode layer with which a voltage is controlled in each pixel) and a second electrode layer (e.g., a common electrode layer with which a common voltage is applied to all pixels), each of which has an opening pattern, are located below a liquid crystal composition. Therefore, the first electrode layer 447 and the second electrode layer 446, one of which is a pixel electrode layer and the other of which is a common electrode layer, are formed over a first substrate 441, and at least one of the first electrode layer and the second electrode layer is formed over an insulating film. The first electrode layer 447 and the second electrode layer 446 have not a flat shape but various opening patterns including a bent portion or a branched comb-like portion. The first electrode layer 447 and the second electrode layer 446 have the same shape and do not overlap with each other in order to generate an electric field between the electrodes.

The first electrode layer 447 and the second electrode layer 446 may have an electrode structure used in an FFS mode. In a lateral electric field mode such as an FFS mode, a first electrode layer (e.g., a pixel electrode layer with which a voltage is controlled in each pixel) having an opening pattern is located below a liquid crystal composition, and further, a second electrode layer (e.g., a common electrode layer with which a common voltage is applied to all pixels) having a flat shape is located below the opening pattern. In this case, the first electrode layer and the second electrode layer, one of which is a pixel electrode layer and the other of which is a common electrode layer, are formed over the first substrate 441, and the pixel electrode layer and the common electrode layer are stacked with an insulating film (or an interlayer insulating film) interposed therebetween. One of the pixel electrode layer and the common electrode layer is formed below the insulating film (or the interlayer insulating film), whereas the other is formed above the insulating film (or the interlayer insulating film) and has various opening patterns including a bent portion or a branched comb-like portion. The first electrode layer 447 and the second electrode layer 446 have the same shape and do not overlap with each other in order to generate an electric field between the electrodes.

The liquid crystal composition including the dioxolane compound represented by the general formula (G1) and a nematic liquid crystal, which is described in Embodiment 1, is used as a liquid crystal composition 444. The liquid crystal composition 444 may further include an organic resin. In this embodiment, the liquid crystal composition 444, which exhibits a blue phase, is provided in a liquid crystal display device with a blue phase exhibited (with a blue phase shown) by being subjected to polymer stabilization treatment.

With an electric field generated between the first electrode layer 447 as the pixel electrode layer and the second electrode layer 446 as the common electrode layer, liquid crystal of the liquid crystal composition 444 is controlled. An electric field in the lateral direction is formed in the liquid crystal, so that liquid crystal molecules can be controlled using the electric field. Since the liquid crystal molecules aligned to exhibit a blue phase can be controlled in the direction parallel to the substrate, a wide viewing angle is obtained.

Figure 3A:
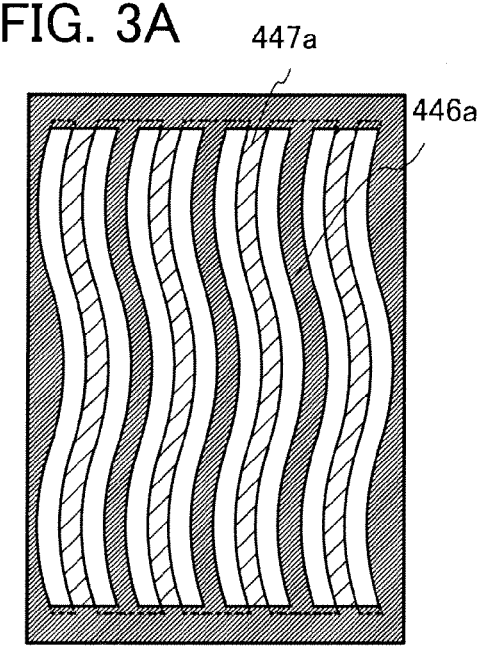
FIGS. 3A to 3D are each a view illustrating one mode of an electrode structure of a liquid crystal display device.
Figure 3B:
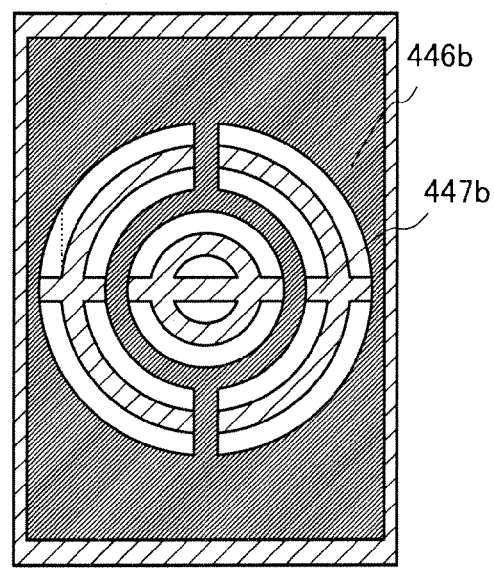
Figure 3C:
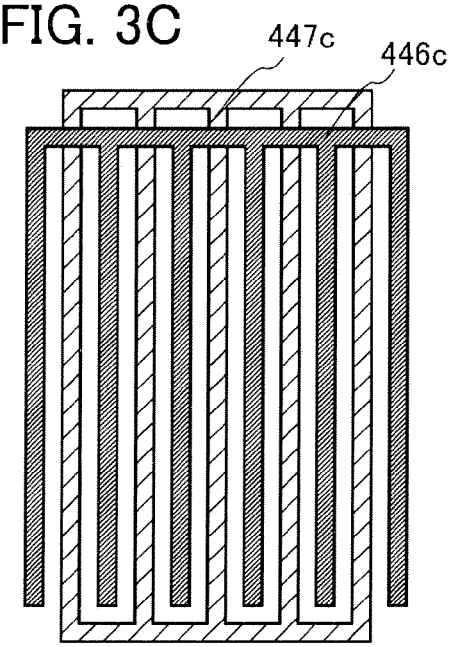
Figure 3D:
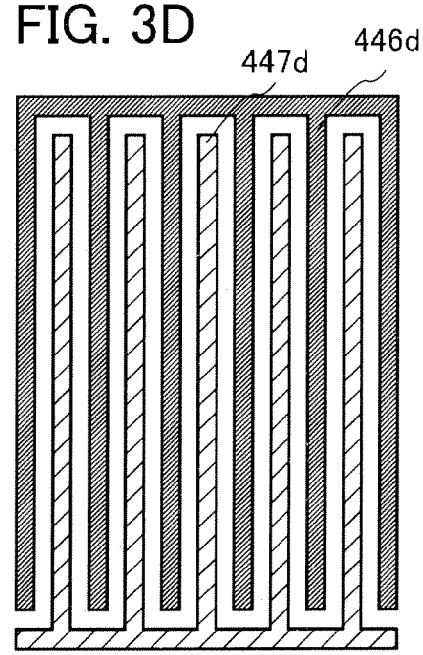

FIGS. 3A to 3D illustrate other examples of the first electrode layer 447 and the second electrode layer 446. As illustrated in top views of FIGS. 3A to 3D, first electrode layers 447a to 447d and second electrode layers 446a to 446d are arranged alternately. In FIG. 3A, the first electrode layer 447a and the second electrode layer 446a have wavelike shapes with curves. In FIG. 3B, the first electrode layer 447b and the second electrode layer 446b have shapes with concentric circular openings. In FIG. 3C, the first electrode layer 447c and the second electrode layer 446c have comb-like shapes and partially overlap with each other. In FIG. 3D, the first electrode layer 447d and the second electrode layer 446d have comb-like shapes in which the electrode layers are engaged with each other. In the case where the first electrode layers 447a, 447b, and 447c overlap with the second electrode layers 446a, 446b, and 446c, respectively, as illustrated in FIGS. 3A to 3C, an insulating film is formed between the first electrode layer 447 and the second electrode layer 446 so that the first electrode layer 447 and the second electrode layer 446 are formed over different films.

Since the first electrode layer 447 and the second electrode layer 446 have opening patterns, they are illustrated as divided plural electrode layers in the cross-sectional view in FIG. 2B. The same applies to the other drawings of this specification.

The transistor 420 is an inverted staggered thin film transistor in which the gate electrode layer 401, a gate insulating layer 402, a semiconductor layer 403, and wiring layers 405a and 405b which function as a source electrode layer and a drain electrode layer are formed over the first substrate 441 having an insulating surface.

There is no particular limitation on the structure of a transistor which can be used for a liquid crystal display device disclosed in this specification. For example, a staggered type or a planar type having a top-gate structure or a bottom-gate structure can be employed. The transistor may have a single-gate structure in which one channel formation region is formed, a double-gate structure in which two channel formation regions are formed, or a triple-gate structure in which three channel formation regions are formed. Alternatively, the transistor may have a dual-gate structure including two gate electrode layers positioned over and below a channel region with a gate insulating layer interposed therebetween.

An insulating film 407 which is in contact with the semiconductor layer 403, and an insulating film 409 are provided to cover the transistor 420. An interlayer film 413 is stacked over the insulating film 409.

There is no particular limitation on the method for forming the interlayer film 413, and the following method can be employed depending on the material: spin coating, dip coating, spray coating, a droplet discharging method (such as an ink-jet method), a printing method (such as screen printing or offset printing), roll coating, curtain coating, knife coating, or the like.

The first substrate 441 and a second substrate 442 which is a counter substrate are firmly attached to each other with a sealant with the liquid crystal composition 444 interposed therebetween. The liquid crystal composition 444 can be formed by a dispensing method (a dropping method), or an injection method in which liquid crystal is injected using capillary action or the like after the first substrate 441 is attached to the second substrate 442.

As the sealant, typically, a visible light curable resin, a UV curable resin, or a thermosetting resin is preferably used. Typically, an acrylic resin, an epoxy resin, an amine resin, or the like can be used. Further, a photopolymerization initiator (typically, a UV polymerization initiator), a thermosetting agent, a filler, or a coupling agent may be contained in the sealant.

Since a liquid crystal composition including a photopolymerization initiator, a polymerizable monomer, and the dioxolane compound represented by the general formula (G1), and a nematic liquid crystal is used as the liquid crystal composition 444, polymer stabilization treatment can be performed by light irradiation.

After the space between the first substrate 441 and the second substrate 442 is filled with the liquid crystal composition, polymer stabilization treatment is performed by light irradiation, whereby the liquid crystal composition 444 is formed. The light has a wavelength at which the polymerizable monomer and the photopolymerization initiator which are used for the liquid crystal composition 444 react. By such polymer stabilization treatment by light irradiation, the temperature range where the liquid crystal composition 444 exhibits a blue phase can be broadened.

In the case where a photocurable resin such as a UV curable resin is used as a sealant and a liquid crystal composition is formed by a dropping method, for example, the sealant may be cured in the light irradiation step of the polymer stabilization treatment.

In this embodiment, a polarizing plate 443a is provided on the outer side (on the side opposite to the liquid crystal composition 444) of the first substrate 441, and a polarizing plate 443b is provided on the outer side (on the side opposite to the liquid crystal composition 444) of the second substrate 442. In addition to the polarizing plate, an optical film such as a retardation plate or an anti-reflection film may be provided. For example, circular polarization with the polarizing plate and the retardation plate may be used. Through the above process, a liquid crystal display device can be completed.

In the case of manufacturing a plurality of liquid crystal display devices using a large-sized substrate (a so-called multiple panel method), a division step can be performed before performing the polymer stabilization treatment or before providing the polarizing plates. In consideration of the influence of the division step on the liquid crystal composition (such as alignment disorder due to force applied in the division step), it is preferable that the division step be performed after attaching the first substrate and the second substrate and before performing the polymer stabilization treatment.

Although not illustrated, a backlight, a sidelight, or the like may be used as a light source. Light from the light source is emitted from the side of the first substrate 441 which is an element substrate so as to pass through the second substrate 442 on the viewing side.

The first electrode layer 447 and the second electrode layer 446 can be formed using a light-transmitting conductive material such as indium oxide containing tungsten oxide, indium zinc oxide containing tungsten oxide, indium oxide containing titanium oxide, indium tin oxide containing titanium oxide, indium tin oxide, indium zinc oxide, indium tin oxide to which silicon oxide is added, or graphene.

The first electrode layer 447 and the second electrode layer 446 can be formed of one or more materials selected from metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

The first electrode layer 447 and the second electrode layer 446 can be formed using a conductive composition including a conductive high molecule (also referred to as a conductive polymer). The pixel electrode formed using the conductive composition preferably has a sheet resistance of less than or equal to 10000 ohms per square and a transmittance of greater than or equal to 70% at a wavelength of 550 nm. Further, the resistivity of the conductive high molecule included in the conductive composition is preferably less than or equal to 0.1 Ω·cm.

As the conductive high molecule, a so-called π-electron conjugated conductive polymer can be used. Examples thereof include polyaniline or a derivative thereof, polypyrrole or a derivative thereof, polythiophene or a derivative thereof, a copolymer of two or more kinds of aniline, pyrrole, and thiophene or a derivative thereof.

An insulating film serving as a base film may be provided between the first substrate 441 and the gate electrode layer 401. The base film has a function of preventing diffusion of an impurity element from the first substrate 441, and can be formed to have a single-layer structure or a layered structure using one or more of a silicon nitride film, a silicon oxide film, a silicon nitride oxide film, and a silicon oxynitride film. The gate electrode layer 401 can be formed to have a single-layer structure or a layered structure using any of metal materials such as molybdenum, titanium, chromium, tantalum, tungsten, aluminum, copper, neodymium, and scandium, and an alloy material which contains any of these materials as its main component. Alternatively, a semiconductor film typified by a polycrystalline silicon film doped with an impurity element such as phosphorus, or a silicide film such as a nickel silicide film may be used as the gate electrode layer 401. By using a light-blocking conductive film as the gate electrode layer 401, light from a backlight (light emitted through the first substrate 441) can be prevented from entering the semiconductor layer 403.

For example, as a two-layer structure of the gate electrode layer 401, the following structures are preferable: a two-layer structure of an aluminum layer and a molybdenum layer stacked thereover, a two-layer structure of a copper layer and a molybdenum layer stacked thereover, a two-layer structure of a copper layer and a titanium nitride layer or a tantalum nitride layer stacked thereover, and a two-layer structure of a titanium nitride layer and a molybdenum layer. As a three-layer structure, a layered structure in which a tungsten layer or a tungsten nitride layer, an alloy layer of aluminum and silicon or an alloy layer of aluminum and titanium, and a titanium nitride layer or a titanium layer are stacked is preferable.

For example, the gate insulating layer 402 can be formed by a plasma CVD method or a sputtering method, with the use of a silicon oxide film, a gallium oxide film, an aluminum oxide film, a silicon nitride film, a silicon oxynitride film, an aluminum oxynitride film, or a silicon nitride oxide film. Alternatively, a high-k material such as hafnium oxide, yttrium oxide, lanthanum oxide, hafnium silicate (HfSi$_x$O$_y$ (x>0, y>0)), hafnium aluminate (HfAl$_x$O$_y$ (x>0, y>0)), hafnium silicate to which nitrogen is added, or hafnium aluminate to which nitrogen is added may be used as a material for the gate insulating layer 402. The use of such a high-k material enables a reduction in gate leakage current.

Alternatively, the gate insulating layer 402 can be formed using a silicon oxide layer by a CVD method using an organosilane gas. As an organosilane gas, a silicon-containing compound such as tetraethoxysilane (TEOS) (chemical formula: Si(OC$_2$H$_5$)$_4$), tetramethylsilane (TMS) (chemical formula: Si(CH$_3$)$_4$), tetramethylcyclotetrasiloxane (TMCTS), octamethylcyclotetrasiloxane (OMCTS), hexamethyldisilazane (HMDS), triethoxysilane (SiH(OC$_2$H$_5$)$_3$), or trisdimethylaminosilane (SiH(N(CH$_3$)$_2$)$_3$) can be used. Note that the gate insulating layer 402 may have a single layer structure or a stacked structure.

A material of the semiconductor layer 403 is not particularly limited and may be determined as appropriate depending on characteristics needed for the transistor 420. Examples of a material which can be used for the semiconductor layer 403 will be described.

The semiconductor layer 403 can be formed using the following material: an amorphous semiconductor formed by a chemical vapor deposition method using a semiconductor source gas typified by silane or germane or by a physical vapor deposition method such as sputtering; a polycrystalline semiconductor formed by crystallizing the amorphous semiconductor with the use of light energy or thermal energy; a microcrystalline semiconductor in which a minute crystalline phase and an amorphous phase coexist; or the like. The semiconductor layer can be formed by a sputtering method, an LPCVD method, a plasma CVD method, or the like.

A typical example of an amorphous semiconductor is hydrogenated amorphous silicon, while a typical example of a crystalline semiconductor is polysilicon. Examples of polysilicon (polycrystalline silicon) are as follows: so-called high-temperature polysilicon which contains polysilicon formed at a process temperature of 800° C. or higher as its main component, so-called low-temperature polysilicon which contains polysilicon formed at a process temperature of 600° C. or lower as its main component, and polysilicon obtained by crystallizing amorphous silicon with the use of an element that promotes crystallization, or the like. It is needless to say that a microcrystalline semiconductor or a semiconductor partly containing a crystal phase can be used as described above.

Alternatively, an oxide semiconductor may be used. In that case, any of the following can be used: indium oxide; tin oxide; zinc oxide; a two-component metal oxide such as an In—Zn-based oxide, a Sn—Zn-based oxide, an Al—Zn-based oxide, a Zn—Mg-based oxide, a Sn—Mg-based oxide, an In—Mg-based oxide, or an In—Ga-based oxide; a three-component metal oxide such as an In—Ga—Zn-based oxide (also referred to as IGZO), an In—Al—Zn-based oxide, an In—Sn—Zn-based oxide, a Sn—Ga—Zn-based oxide, an Al—Ga—Zn-based oxide, a Sn—Al—Zn-based oxide, an In—Hf—Zn-based oxide, an In—La—Zn-based oxide, an In—Ce—Zn-based oxide, an In—Pr—Zn-based oxide, an In—Nd—Zn-based oxide, an In—Sm—Zn-based oxide, an In—Eu—Zn-based oxide, an In—Gd—Zn-based oxide, an In—Tb—Zn-based oxide, an In—Dy—Zn-based oxide, an In—Ho—Zn-based oxide, an In—Er—Zn-based oxide, an In—Tm—Zn-based oxide, an In—Yb—Zn-based oxide, or an In—Lu—Zn-based oxide; and a four-component metal oxide such as an In—Sn—Ga—Zn-based oxide, an In—Hf—Ga—Zn-based oxide, an In—Al—Ga—Zn-based oxide, an In—Sn—Al—Zn-based oxide, an In—Sn—Hf—Zn-based oxide, or an In—Hf—Al—Zn-based oxide. In addition, any of the above oxide semiconductors may contain an element other than In, Ga, Sn, and Zn, for example, $SiO_2$.

Here, for example, the In—Ga—Zn-based oxide semiconductor refers to an oxide semiconductor containing indium (In), gallium (Ga), and zinc (Zn) and there is no particular limitation on the composition ratio thereof.

For the oxide semiconductor layer, a thin film expressed by the chemical formula, $InMO_3(ZnO)_m$ (m>0), can be used. Here, M represents one or more metal elements selected from Ga, Al, Mn, and Co. For example, M can be Ga, Ga and Al, Ga and Mn, or Ga and Co.

In the case where the In—Sn—Zn—O-based material is used as the oxide semiconductor, the atomic ratio of metal elements in a target may be In:Sn:Zn=1:2:2, 2:1:3, or 1:1:1, for example.

In the case where an In—Zn—O-based material is used as the oxide semiconductor, the atomic ratio is set so that In/Zn is in a range from 0.5 to 50, preferably from 1 to 20, more preferably from 1.5 to 15. When the atomic ratio of Zn is in the above-described range, a transistor can be improved in field-effect mobility. Here, when the atomic ratio of the compound is In:Zn:O=X:Y:Z, the relation Z>1.5X+Y is satisfied.

For the oxide semiconductor layer, a crystalline oxide semiconductor which is neither a single crystal nor an amorphous and has c-axis orientation (also referred to as c-axis aligned crystalline oxide semiconductor (CAAC-OS)).

In a process of forming the semiconductor layer and the wiring layer, an etching step is used to process thin films into desired shapes. Dry etching or wet etching can be employed for the etching step.

The etching conditions (such as an etchant, etching time, and temperature) are appropriately adjusted depending on the material so that the material can be etched to have a desired shape.

As a material of the wiring layers 405*a* and 405*b* serving as source and drain electrode layers, an element selected from Al, Cr, Ta, Ti, Mo, and W; an alloy containing any of the above elements as its component; an alloy film containing a combination of any of these elements; and the like can be given. Further, in the case where heat treatment is performed, the conductive film preferably has heat resistance against the heat treatment. Since the use of aluminum alone brings disadvantages such as low heat resistance and a tendency to corrosion, aluminum is used in combination with a conductive material having heat resistance. As the conductive material having heat resistance, which is combined with aluminum, it is possible to use an element selected from titanium (Ti), tantalum (Ta), tungsten (W), molybdenum (Mo), chromium (Cr), neodymium (Nd), and scandium (Sc); an alloy containing any of these elements as its component; an alloy containing a combination of any of these elements; or a nitride containing any of these elements as its component.

The gate insulating layer 402, the semiconductor layer 403, and the wiring layers 405*a* and 405*b* serving as source and drain electrode layers may be successively formed without being exposed to the air. Successive film formation without exposure to the air makes it possible to obtain each interface between stacked layers, which is not contaminated by atmospheric components or impurity elements in the air. Therefore, variation in characteristics of the transistor can be reduced.

Note that the semiconductor layer 403 is partly etched so as to have a groove (a depressed portion).

As the insulating film 407 and the insulating film 409 which cover the transistor 420, an inorganic insulating film or an organic insulating film formed by a dry method or a wet method can be used. For example, it is possible to use a silicon nitride film, a silicon oxide film, a silicon oxynitride film, an aluminum oxide film, or a tantalum oxide film, which is formed by a CVD method, a sputtering method, or the like. Alternatively, an organic material such as polyimide, acrylic, a benzocyclobutene-based resin, polyamide, or epoxy can be used. As an alternative to such organic materials, it is possible to use a low-dielectric constant material (a low-k material), a siloxane-based resin, phosphosilicate glass (PSG), borophosphosilicate glass (BPSG), or the like. A gallium oxide film can also be used as the insulating film 407.

Note that the siloxane-based resin corresponds to a resin including a Si—O—Si bond formed using a siloxane-based material as a starting material. The siloxane-based resin may include as a substituent an organic group (e.g., an alkyl group or an aryl group) or a fluoro group. The organic group may include a fluoro group. A siloxane-based resin is applied by a coating method and baked; thus, the insulating film 407 can be formed.

Alternatively, the insulating film 407 and the insulating film 409 may be formed by stacking a plurality of insulating films formed using any of these materials. For example, a structure may be employed in which an organic resin film is stacked over an inorganic insulating film.

Further, with the use of a resist mask having regions with plural thicknesses (typically, two different thicknesses) which is formed using a multi-tone mask, the number of photomasks can be reduced, resulting in a simplified process and lower cost.

As described above, the use of the liquid crystal composition including the dioxolane compound represented by the general formula (G1) and a nematic liquid crystal makes it possible to provide a liquid crystal element and a liquid crystal display device with lower driving voltage. Consequently, a liquid crystal display device with lower power consumption can be provided.

Since the liquid crystal composition including the dioxolane compound represented by the general formula (G1) and a nematic liquid crystal and exhibiting a blue phase is capable of quick response, a high-performance liquid crystal display device can be achieved.

This embodiment can be implemented in appropriate combination with any of the structures described in the other embodiments.

Embodiment 3

A liquid crystal display device having a display function can be manufactured by manufacturing transistors and using the transistors for a pixel portion and further for a driver circuit. Further, part or the whole of the driver circuit can be formed over the same substrate as the pixel portion, using the transistor, whereby a system-on-panel can be obtained.

The liquid crystal display device includes a liquid crystal element (also referred to as a liquid crystal display element) as a display element.

Further, a liquid crystal display device includes a panel in which a liquid crystal display element is sealed, and a module in which an IC or the like including a controller is mounted to the panel. One embodiment of the present invention also relates to an element substrate, which corresponds to one mode in which the display element has not been completed in a manufacturing process of the liquid crystal display device, and the element substrate is provided with a means for supplying current to the display element in each of a plurality of pixels. Specifically, the element substrate may be in a state where it is provided only with a pixel electrode of the display element, in a state where a conductive film to be a pixel electrode has been formed and the conductive film has not yet been etched to form the pixel electrode, or in any other state.

Note that a liquid crystal display device in this specification means an image display device, a display device, or a light source (including a lighting device). Further, the liquid crystal display device includes any of the following modules in its category: a module to which a connector such as a flexible printed circuit (FPC), tape automated bonding (TAB) tape, or a tape carrier package (TCP) is attached; a module having TAB tape or a TCP which is provided with a printed wiring board at the end thereof; and a module having an integrated circuit (IC) directly mounted on a display element by a chip on glass (COG) method.

Figure 4B:
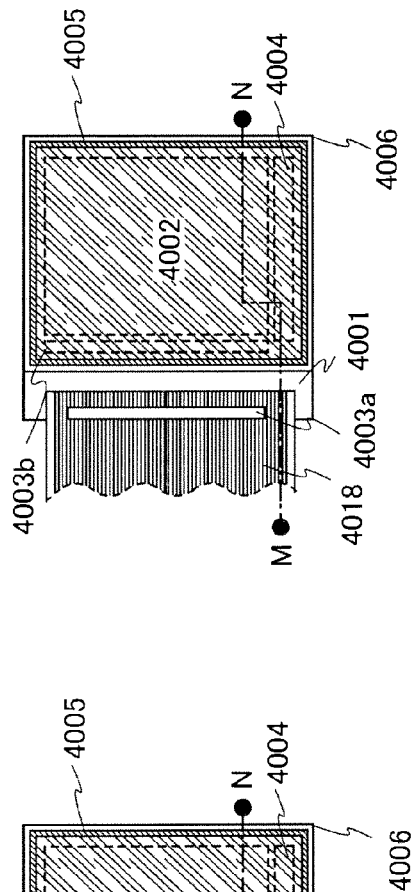
Figure 4B:
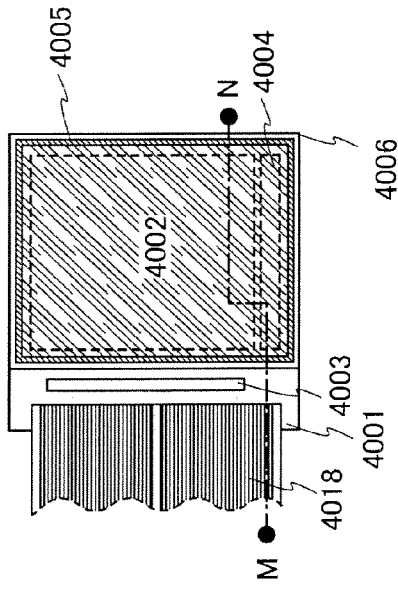
Figure 4B:
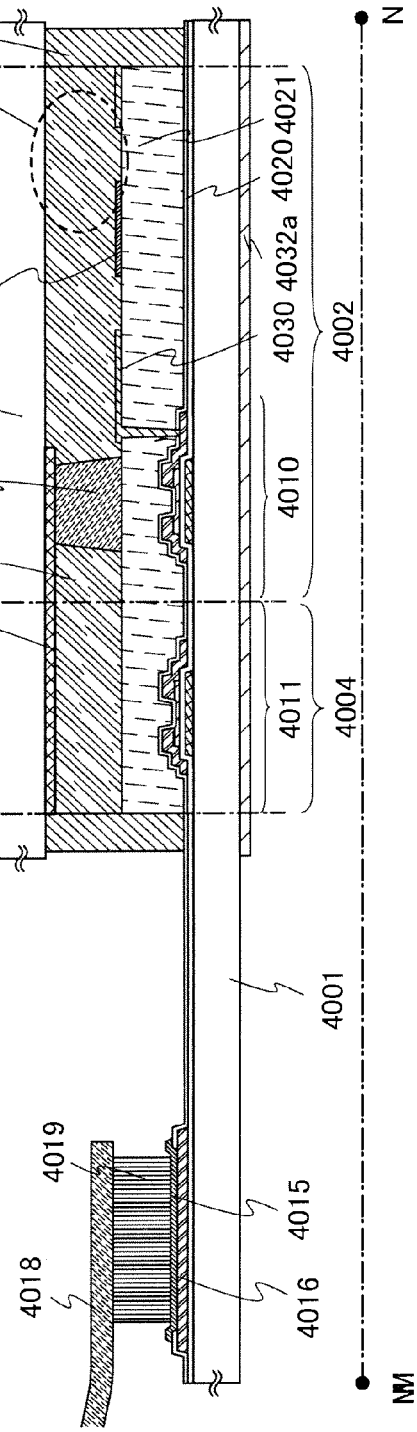

The appearance and a cross section of a liquid crystal display panel, which is an embodiment of a liquid crystal display device, will be described with reference to FIGS. 4A1, 4A2, and 4B. FIGS. 4A1 and 4A2 are each a top view of a panel in which transistors 4010 and 4011 formed over a first substrate 4001 and a liquid crystal element 4013 are sealed between the first substrate 4001 and a second substrate 4006 with a sealant 4005. FIG. 4B is a cross-sectional view taken along line M-N of FIGS. 4A1 and 4A2.

The sealant 4005 is provided to surround a pixel portion 4002 and a scanning line driver circuit 4004 that are provided over the first substrate 4001. The second substrate 4006 is provided over the pixel portion 4002 and the scanning line driver circuit 4004. Therefore, the pixel portion 4002 and the scanning line driver circuit 4004 are sealed together with a liquid crystal composition 4008, by the first substrate 4001, the sealant 4005, and the second substrate 4006.

In FIG. 4A1, a signal line driver circuit 4003 that is formed using a single crystal semiconductor film or a polycrystalline semiconductor film over a substrate separately prepared is mounted in a region different from the region surrounded by the sealant 4005 over the first substrate 4001. Note that FIG. 4A2 illustrates an example in which part of the signal line driver circuit is formed using a transistor provided over the first substrate 4001. A signal line driver circuit 4003b is formed over the first substrate 4001, and a signal line driver circuit 4003a formed using a single crystal semiconductor film or a polycrystalline semiconductor film is mounted on a substrate separately prepared.

Note that there is no particular limitation on the connection method of a driver circuit which is separately formed, and COG, wire bonding, TAB, or the like can be used. FIG. 4A1 illustrates an example of mounting the signal line driver circuit 4003 by COG, and FIG. 4A2 illustrates an example of mounting the signal line driver circuit 4003 by TAB.

The pixel portion 4002 and the scanning line driver circuit 4004 provided over the first substrate 4001 each include a plurality of transistors. FIG. 4B illustrates the transistor 4010 included in the pixel portion 4002 and the transistor 4011 included in the scanning line driver circuit 4004. An insulating layer 4020 and an interlayer film 4021 are provided over the transistors 4010 and 40111.

As the transistors 4010 and 4011, the transistor which is described in Embodiment 2 or 3 can be employed.

Further, a conductive layer may be provided over the interlayer film 4021 or the insulating layer 4020 so as to overlap with a channel formation region of a semiconductor layer of the transistor 4011 for the driver circuit. The conductive layer may have the same potential as or a potential different from that of a gate electrode layer of the transistor 4011 and can function as a second gate electrode layer. Further, the potential of the conductive layer may be GND or the conductive layer may be in a floating state.

A pixel electrode layer 4030 and a common electrode layer 4031 are provided over the interlayer film 4021, and the pixel electrode layer 4030 is electrically connected to the transistor 4010. The liquid crystal element 4013 includes the pixel electrode layer 4030, the common electrode layer 4031, and the liquid crystal composition 4008. Note that a polarizing plate 4032a and a polarizing plate 4032b are provided on the outer sides of the first substrate 4001 and the second substrate 4006, respectively.

The liquid crystal composition including the dioxolane compound represented by the general formula (G1) and a nematic liquid crystal, which is described in Embodiment 1, is used as the liquid crystal composition 4008. The structures of the pixel electrode layer and the common electrode layer described in Embodiment 1 or 2 can be used for the pixel electrode layer 4030 and the common electrode layer 4031.

In this embodiment, the liquid crystal composition 4008, which exhibits a blue phase, is provided in a liquid crystal display device with a blue phase exhibited (with a blue phase shown) by being subjected to polymer stabilization treatment. Therefore, in this embodiment, the pixel electrode layer 4030 and the common electrode layer 4031 have opening patterns, as the electrode layers illustrated in FIG. 1A in Embodiment 1 or FIGS. 3A to 3D in Embodiment 2.

With an electric field generated between the pixel electrode layer 4030 and the common electrode layer 4031, liquid crystal of the liquid crystal composition 4008 is controlled. An electric field in a lateral direction is formed in the liquid crystal, so that liquid crystal molecules can be controlled using the electric field. Since the liquid crystal molecules aligned to exhibit a blue phase can be controlled in the direction parallel to the substrate, a wide viewing angle is obtained.

As the first substrate 4001 and the second substrate 4006, glass, plastic, or the like having a light-transmitting property can be used. As plastic, a polyvinyl fluoride (PVF) film, a polyester film, or an acrylic resin film can be used. A sheet with a structure in which an aluminum foil is sandwiched between PVF films or polyester films, or a fiberglass-reinforced plastics (FRP) plate can also be used.

A columnar spacer denoted by reference numeral 4035 is obtained by selective etching of an insulating film and is provided in order to control the thickness of the liquid crystal composition 4008 (a cell gap). Alternatively, a spherical spacer may be used. In the liquid crystal display device including the liquid crystal composition 4008, the cell gap which is the thickness of the liquid crystal composition is preferably greater than or equal to 1 μm and less than or equal to 20 μm. In this specification, the thickness of a cell gap refers to the maximum thickness (film thickness) of a liquid crystal composition.

Although FIGS. 4A1, 4A2, and 4B illustrate examples of transmissive liquid crystal display devices, one embodiment of the present invention can also be applied to a transflective liquid crystal display device and a reflective liquid crystal display device.

FIGS. 4A1, 4A2, and 4B illustrate examples of liquid crystal display devices in which a polarizing plate is provided on the outer side (the viewing side) of a substrate; however, the polarizing plate may be provided on the inner side of the substrate. The position of the polarizing plate may be determined as appropriate depending on the material of the polarizing plate and conditions of the manufacturing process. Furthermore, a light-blocking layer serving as a black matrix may be provided.

A color filter layer or a light-blocking layer may be formed as part of the interlayer film 4021. In FIGS. 4A1, 4A2, and 4B, a light-blocking layer 4034 is provided on the second substrate 4006 side so as to cover the transistors 4010 and 4011. By providing the light-blocking layer 4034, the contrast can be more increased and the transistors can be more stabilized.

The transistors may be, but is not necessarily, covered with the insulating layer 4020 which functions as a protective film of the transistors.

Note that the protective film is provided to prevent entry of contaminant impurities such as an organic substance, metal, and moisture in the air and is preferably a dense film. The protective film may be formed by a sputtering method to have a single-layer structure or a layered structure including any of a silicon oxide film, a silicon nitride film, a silicon oxynitride film, a silicon nitride oxide film, an aluminum oxide film, an aluminum nitride film, an aluminum oxynitride film, and an aluminum nitride oxide film.

Further, in the case of further forming a light-transmitting insulating layer as a planarizing insulating film, the light-transmitting insulating layer can be formed using an organic material having heat resistance, such as polyimide, acrylic, a benzocyclobutene-based resin, polyamide, or epoxy. As an alternative to such organic materials, it is possible to use a low-dielectric constant material (a low-k material), a siloxane-based resin, phosphosilicate glass (PSG), borophosphosilicate glass (BPSG), or the like. The insulating layer may be formed by stacking a plurality of insulating films formed of these materials.

There is no particular limitation on the method for forming the insulating layer having a stacked structure, and the following method can be employed depending on the material: sputtering, spin coating, dip coating, spray coating, a droplet discharging method (such as an ink-jet method), a printing method (such as screen printing or offset printing), roll coating, curtain coating, knife coating, or the like.

The pixel electrode layer 4030 and the common electrode layer 4031 can be formed using a light-transmitting conductive material such as indium oxide containing tungsten oxide, indium zinc oxide containing tungsten oxide, indium oxide containing titanium oxide, indium tin oxide containing titanium oxide, indium tin oxide, indium zinc oxide, indium tin oxide to which silicon oxide is added, or graphene.

Alternatively, the pixel electrode layer 4030 and the common electrode layer 4031 can be formed using one or more of the following: metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and nitrides thereof.

The pixel electrode layer 4030 and the common electrode layer 4031 can be formed using a conductive composition including a conductive macromolecule (also referred to as a conductive polymer).

Further, a variety of signals and potentials are supplied to the signal line driver circuit 4003 which is formed separately, the scanning line driver circuit 4004, or the pixel portion 4002 from an FPC 4018.

Further, since the transistor is easily broken by static electricity or the like, a protective circuit for protecting the driver circuits is preferably provided over the same substrate as a gate line or a source line. The protection circuit is preferably formed using a nonlinear element.

In FIGS. 4A1, 4A2, and 4B, a connection terminal electrode 4015 is formed using the same conductive film as the pixel electrode layer 4030, and a terminal electrode 4016 is formed using the same conductive film as source electrode layers and drain electrode layers of the transistors 4010 and 4011.

The connection terminal electrode 4015 is electrically connected to a terminal included in the FPC 4018 through an anisotropic conductive film 4019.

Although FIGS. 4A1, 4A2, and 4B illustrate an example in which the signal line driver circuit 4003 is formed separately and mounted on the first substrate 4001, one embodiment of the present invention is not limited to this structure. The scanning line driver circuit may be separately formed and then mounted, or only part of the signal line driver circuit or part of the scanning line driver circuit may be separately formed and then mounted.

As described above, with the use of a liquid crystal composition including the dioxolane compound represented by the general formula (G1) and a nematic liquid crystal, a liquid crystal element and a liquid crystal display device which is driven at low voltage can be provided. Thus, a liquid crystal display device with lower power consumption can be provided.

Since the liquid crystal composition including the dioxolane compound represented by the general formula (G1) and a nematic liquid crystal and exhibiting a blue phase is capable of quick response, a high-performance liquid crystal display device can be achieved.

This embodiment can be implemented in appropriate combination with any of the structures described in the other embodiments.

Embodiment 4

A liquid crystal display device disclosed in this specification can be applied to a variety of electronic apparatuses (including game machines). Examples of electronic apparatuses are a television set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a portable information terminal, an audio reproducing device, a large-sized game machine such as a pachinko machine, and the like.

Figure 5A:
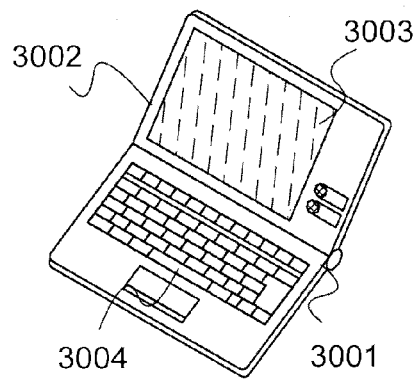
FIGS. 5A to 5F are each a view illustrating an electronic apparatus.

FIG. 5A illustrates a laptop personal computer, which includes a main body 3001, a housing 3002, a display portion 3003, a keyboard 3004, and the like. The liquid crystal display device described in any of Embodiments 1 to 3 is used for the display portion 3003, whereby a laptop personal computer with low power consumption can be provided.

Figure 5B:
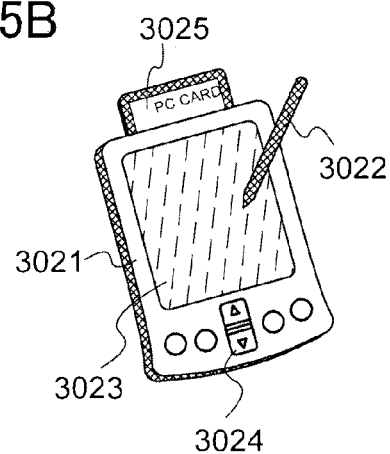

FIG. 5B illustrates a personal digital assistant (PDA), which includes a main body 3021 provided with a display portion 3023, an external interface 3025, operation buttons 3024, and the like. A stylus 3022 is provided as an accessory for operation. The liquid crystal display device described in any of Embodiments 1 to 3 is used for the display portion 3023, whereby a personal digital assistant (PDA) with low power consumption can be provided.

Figure 5C:
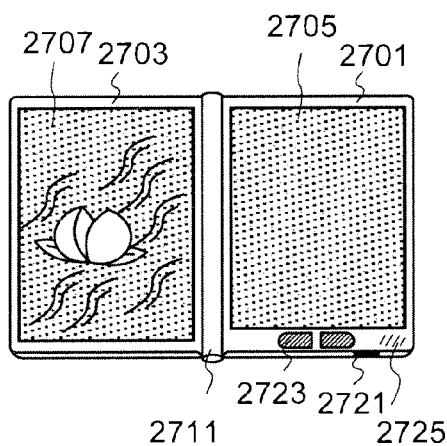

FIG. 5C illustrates an e-book reader, which includes two housings, a housing 2701 and a housing 2703. The housing 2701 and the housing 2703 are combined with a hinge 2711 so that the e-book reader can be opened and closed with the hinge 2711 as an axis. With such a structure, the e-book reader can operate like a paper book.

A display portion 2705 and a display portion 2707 are incorporated in the housing 2701 and the housing 2703, respectively. The display portion 2705 and the display portion 2707 may display one image or different images. In the structure where different images are displayed in the above display portions, for example, the right display portion (the display portion 2705 in FIG. 5C) can display text and the left display portion (the display portion 2707 in FIG. 5C) can display images. The liquid crystal display device described in any of Embodiments 1 to 3 is used for the display portions 2705 and 2707, whereby an e-book reader with low power consumption can be provided. In the case of using a transflective or reflective liquid crystal display device as the display portion 2705, the e-book reader may be used in a comparatively bright environment; therefore, a solar cell may be provided so that power generation by the solar cell and charge by a battery can be performed. When a lithium ion battery is used as the battery, there are advantages of downsizing and the like.

FIG. 5C illustrates an example in which the housing 2701 is provided with an operation portion and the like. For example, the housing 2701 is provided with a power switch 2721, operation keys 2723, a speaker 2725, and the like. With the operation keys 2723, pages can be turned. Note that a keyboard, a pointing device, or the like may also be provided on the surface of the housing, on which the display portion is provided. Furthermore, an external connection terminal (an earphone terminal, a USB terminal, or the like), a recording medium insertion portion, and the like may be provided on the back surface or the side surface of the housing. Further, the e-book reader may have a function of an electronic dictionary.

The e-book reader may transmit and receive data wirelessly. Through wireless communication, desired book data or the like can be purchased and downloaded from an electronic book server.

Figure 5D:
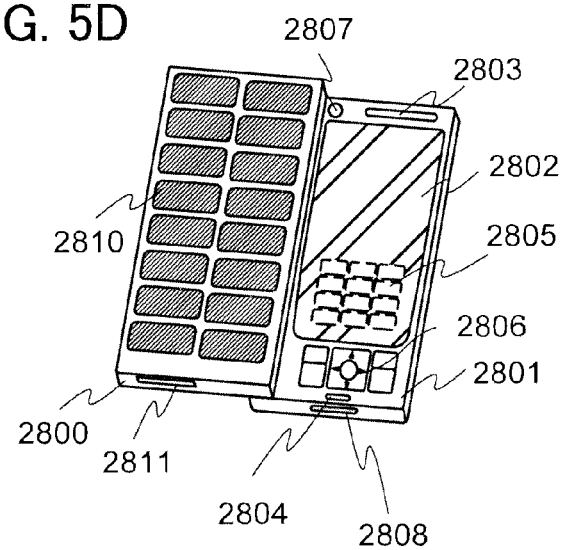

FIG. 5D illustrates a mobile phone, which includes two housings, a housing 2800 and a housing 2801. The housing 2801 includes a display panel 2802, a speaker 2803, a microphone 2804, a pointing device 2806, a camera lens 2807, an external connection terminal 2808, and the like. In addition, the housing 2800 includes a solar cell 2810 having a function of charge of the mobile phone, an external memory slot 2811, and the like. An antenna is incorporated in the housing 2801. The liquid crystal display device described in any of Embodiments 1 to 3 is used for the display panel 2802, whereby a mobile phone with low power consumption can be provided.

Further, the display panel 2802 is provided with a touch panel. A plurality of operation keys 2805 which is displayed as images is illustrated by dashed lines in FIG. 5D. Note that a boosting circuit by which a voltage output from the solar cell 2810 is increased to be sufficiently high for each circuit is also provided.

The display direction of the display panel 2802 is changed as appropriate depending on a usage pattern. Further, the camera lens 2807 is provided on the same surface as the display panel 2802, so that the mobile phone can be used as a video phone. The speaker 2803 and the microphone 2804 can be used for videophone calls, recording and playing sound, and the like as well as voice calls. Furthermore, the housings 2800 and 2801 which are developed as illustrated in FIG. 5D can overlap with each other by sliding; thus, the size of the mobile phone can be decreased, which makes the mobile phone suitable for being carried.

The external connection terminal 2808 can be connected to an AC adapter and various types of cables such as a USB cable, and charging and data communication with a personal computer are possible. Moreover, a large amount of data can be stored by inserting a storage medium into the external memory slot 2811 and can be moved.

Further, in addition to the above functions, an infrared communication function, a television reception function, or the like may be provided.

Figure 5E:
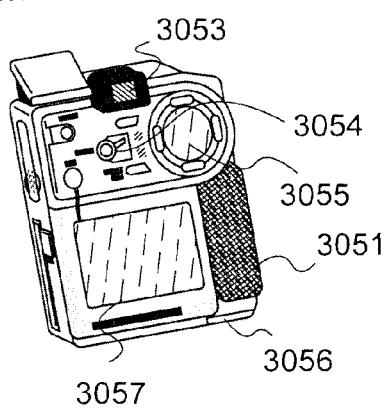

FIG. 5E illustrates a digital video camera, which includes a main body 3051, a display portion A 3057, an eyepiece 3053, an operation switch 3054, a display portion B 3055, a battery 3056, and the like. The liquid crystal display device described in any of Embodiments 1 to 3 is used for the display portion A 3057 and the display portion B 3055, whereby a digital video camera with low power consumption can be provided.

Figure 5F:
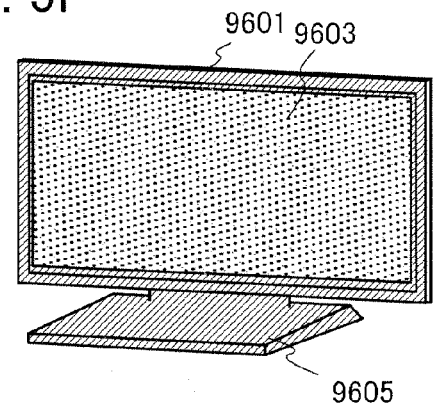

FIG. 5F illustrates a television set, which includes a housing 9601, a display portion 9603, and the like. The display portion 9603 can display images. Here, the housing 9601 is supported by a stand 9605. The liquid crystal display device described in any of Embodiments 1 to 3 is used for the display portion 9603, whereby a television set with low power consumption can be provided.

The television set can operate with an operation switch of the housing 9601 or a separate remote control device. Further, the remote controller may be provided with a display portion for displaying data output from the remote controller.

Note that the television set is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) data communication can be performed.

This embodiment can be implemented in appropriate combination with any of the structures described in the other embodiments.

Example 1

This example shows an example of synthesizing (R)(R)-4,5-bis[hydroxy(diphenanthryl)methyl]-2,2-dimethyl-1,3-dioxolane (abbreviation: R-DOL-Pn) represented by the structural formula (101) in Embodiment 1.

Synthesis method of (R)(R)-4,5-bis[hydroxy(diphenanthrvyl)methyl]-2,2-dimethyl-1,3-dioxolane (abbreviation: R-DOL-Pn)

A synthesis scheme of R-DOL-Pn (abbreviation) represented by the structural formula (101) is shown in (L-1) below.

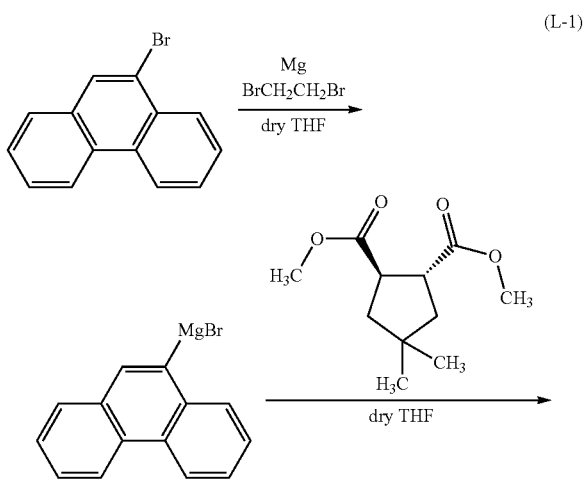

(L-1)

-continued

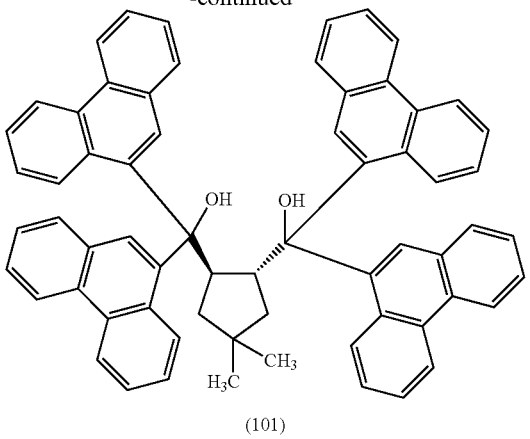

(101)

In a 200-mL three-neck flask was put 2.3 g (95 mmol) of magnesium, and the atmosphere in the flask was replaced with nitrogen. Into this mixture were added 50 mL of dehydrated tetrahydrofuran and 0.5 mL, of dibromoethane, and the mixture was stirred. Into this mixture was gradually added a solution obtained by dissolving 25 g (97 mmol) of 9-bromophenanthrene in 50 ml, of dehydrated tetrahydrofuran with a dropping funnel while the mixture was being refluxed. After the dropping, this mixture was refluxed under a nitrogen stream at 80° C. for two hours. After a predetermined time, this mixture was returned to room temperature. Into this mixture was gradually added a solution obtained by dissolving 3.6 mL (20 mmol) of (R)(R)-2,3-O-isopropylidene-L-tartaric acid dimethyl in 10 mL of dehydrated tetrahydrofuran with a dropping funnel while the mixture was being refluxed. After the dropping, this mixture was refluxed under a nitrogen stream at 80° C. for an hour. After a predetermined time, into this mixture were added methanol, water, and dilute hydrochloric acid sequentially, and an aqueous layer of this mixture was extracted with toluene. The obtained extracted solution and an organic layer were combined, washed with a saturated aqueous solution of sodium hydrogen carbonate and saturated saline, and dried with magnesium sulfate. The mixture was separated by gravity filtration, and the obtained filtrate was concentrated to give an oily yellow substance. This oily substance was purified by silica gel column chromatography (developing solvent: toluene). The obtained fraction was concentrated to give an oily yellow substance. This oily substance was purified by high performance liquid chromatography (developing solvent: chloroform) to give a yellow solid. This solid was recrystallized with toluene, so that 10 g of a white solid, which was a target substance, was obtained in a yield of 58%.

Example 2

In this example, liquid crystal compositions each according to one embodiment of the present invention, and liquid crystal elements including the liquid crystal compositions were made, and the characteristics of the liquid crystal compositions and the liquid crystal elements were evaluated.

Tables 1 to 3 show components of liquid crystal compositions 1 to 5 made in this example. Note that in each of Tables 1 to 3, the mixture proportions are all represented in weight ratios, and the proportion (wt %)$_{*1}$ indicates a proportion in liquid crystal and the proportion (wt %)$_{*2}$ indicates a proportion in a liquid crystal composition.

TABLE 1

| Components | | | Proportion (wt %)$_{*1}$ | Liquid crystal composition 1 Proportion (wt %)$_{*2}$ | Liquid crystal composition 2 Proportion (wt %)$_{*2}$ |
|---|---|---|---|---|---|
| Liquid crystal | Liquid crystal 1 | MDA-00-3506 | 30 | 94.32 | 96.03 |
| | Liquid crystal 2 | NEDO LC-C | 20 | | |
| | Liquid crystal 3 | CPP-3FFF | 20 | | |
| | Liquid crystal 4 | PEP-5FCNF | 30 | | |
| Chiral agent | | R-DOL-Pn | | 5.68 | 3.97 |

$_{*1}$shows a proportion in a liquid crystal,
$_{*2}$shows a proportion in a liquid crystal composition.

TABLE 2

| Components | | | Proportion (wt %)$_{*1}$ | Liquid crystal composition 3 Proportion (wt %)$_{*2}$ | Liquid crystal composition 4 Proportion (wt %)$_{*2}$ |
|---|---|---|---|---|---|
| Liquid crystal | Liquid crystal 1 | E-8 | 40 | 96.25 | 95.65 |
| | Liquid crystal 2 | CPP-3FF | 30 | | |
| | Liquid crystal 3 | PEP-5CNF | 30 | | |
| Chiral agent | | R-DOL-Pn | | 4.75 | 4.35 |

$_{*1}$shows a proportion in a liquid crystal,
$_{*2}$shows a proportion in a liquid crystal composition.

TABLE 3

|  | Components |  | Proportion (wt %)*1 | Liquid crystal composition 5 Proportion (wt %)*2 |
|---|---|---|---|---|
| Liquid crystal | Liquid crystal 1 | PEP-5FCNF | 18 | 97.01 |
|  | Liquid crystal 2 | 5CT | 4.4 |  |
|  | Liquid crystal 3 | PP-O3FCNF | 6.4 |  |
|  | Liquid crystal 4 | PP-O5FCNF | 4.8 |  |
|  | Liquid crystal 5 | PP-O8FCNF | 6.4 |  |
|  | Liquid crystal 6 | CPEP-5FCNF | 30 |  |
|  | Liquid crystal 7 | PEP-3FCNF | 30 |  |
| Chiral agent |  | R-DOL-Pn |  | 2.99 |

*1 shows a proportion in a liquid crystal,
*2 shows a proportion in a liquid crystal composition.

In the liquid crystal compositions 1 and 2, MDA-00-3506 (produced by Merck Ltd., Japan) as liquid crystal 1, NEDO LC-C (produced by Merck Ltd., Japan) as liquid crystal 2, 4-(trans-4-n-propylcyclohexyl)-3',4',5'-trifluoro-1,1'-biphenyl (abbreviation: CPP-3FFF) as liquid crystal 3, and 4-n-pentylbenzoic acid 4-cyano-3,5-difluorophenyl ester (abbreviation: PEP-5FCNF) as liquid crystal 4 were used.

In the liquid crystal compositions 3 and 4, liquid crystal mixture E-8 (produced by LCC Corporation) as liquid crystal 1, 4-(trans-4-n-propylcyclohexyl)-3',4'-difluoro-1,1'-biphenyl (abbreviation: CPP-3FF) (produced by Daily Polymer Corporation) as liquid crystal 2, and 4-n-pentylbenzoic acid 4-cyano-3-fluorophenyl ester (abbreviation: PEP-5CNF) (produced by Daily Polymer Corporation) as liquid crystal 3 were used.

In the liquid crystal composition 5, 4-n-pentylbenzoic acid 4-cyano-3,5-difluorophenyl ester (abbreviation: PEP-5FCNF) as liquid crystal 1, 4-cyano-4''-n-pentyl-p-terphenyl (abbreviation: 5CT) (produced by LCC Corporation) as liquid crystal 2, 4-(4-n-propoxyphenyl)-2,6-difluorobenzonitrile (abbreviation: PP—O3FCNF) as liquid crystal 3, 4-(4-n-pentoxyphenyl)-2,6-difluorobenzonitrile (abbreviation: PP—O5FCNF) as liquid crystal 4, 4-(4-n-octoxyphenyl)-2,6-difluorobenzonitrile (abbreviation: PP—O8FCNF) as liquid crystal 5, 4-(trans-4-n-pentylcyclohexyl)benzoic acid 4-cyano-3,5-difluorophenyl ester (abbreviation: CPEP-5FCNF) as liquid crystal 6, and 4-n-propylbenzoic acid 4-cyano-3,5-difluorophenyl ester (abbreviation: PEP-3FCNF) as liquid crystal 7 were used.

In the liquid crystal compositions 1 to 5, R-DOL-Pn (abbreviation) represented by the structural formula (101) was used as a chiral agent.

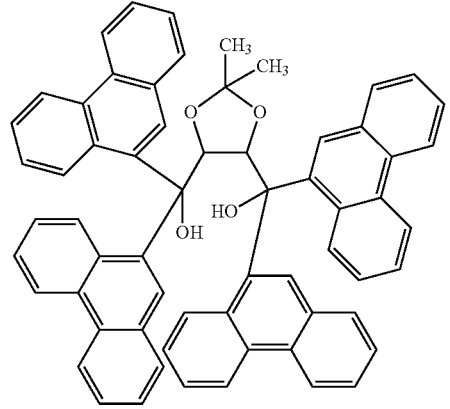

(101)

Note that structural formulae of CPP-3FFF (abbreviation), CPP-3FF (abbreviation), PEP-5FCNF (abbreviation), PEP-5CNF (abbreviation), 5CT (abbreviation), PP—O3FCNF (abbreviation), PP—O5FCNF (abbreviation), PP—O8FCNF (abbreviation), CPEP-5FCNF (abbreviation), and PEP-3FCNF (abbreviation) used in this example are shown below.

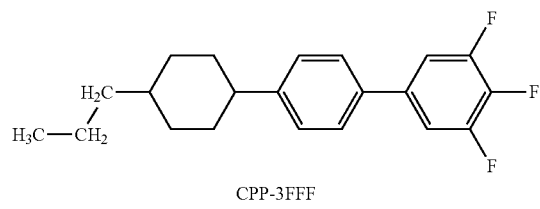

CPP-3FFF

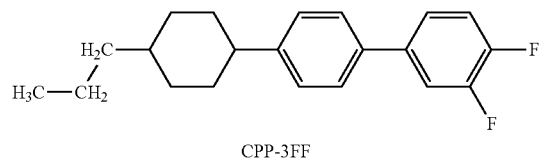

CPP-3FF

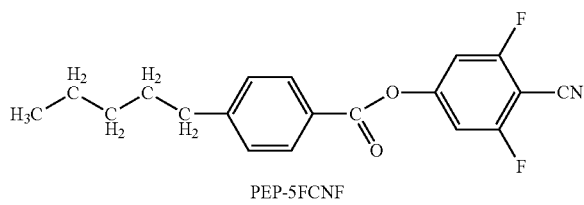

PEP-5FCNF

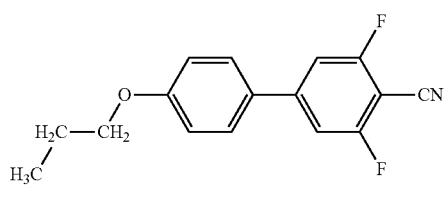

PP-O3FCNF

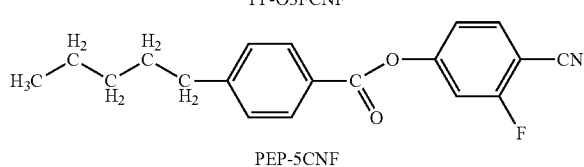

PEP-5CNF

-continued

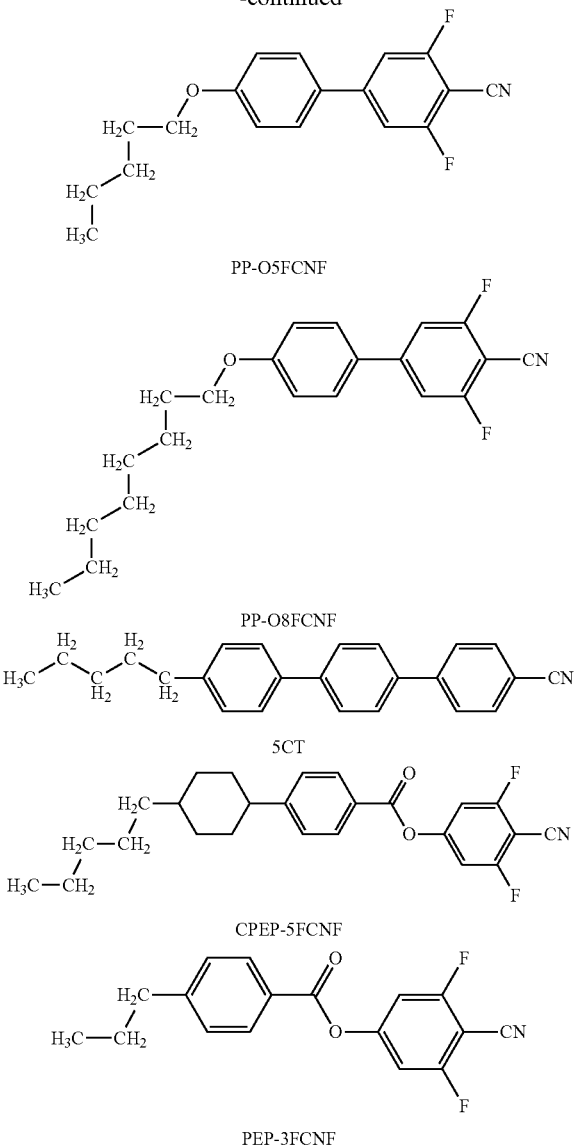

PP-O5FCNF

PP-O8FCNF

5CT

CPEP-5FCNF

PEP-3FCNF

In this example, a liquid crystal element 1A, a liquid crystal element 2A, a liquid crystal element 3A, a liquid crystal element 4A, and a liquid crystal element 5A were fabricated with the use of the liquid crystal composition 1, the liquid crystal composition 2, the liquid crystal composition 3, the liquid crystal composition 4, and the liquid crystal composition 5, respectively. The fabrication method is described below.

The liquid crystal elements 1A to 5A were each fabricated in such a manner that a glass substrate over which a pixel electrode layer and a common electrode layer were formed in comb-like shapes as in FIG. 3D and a glass substrate serving as a counter substrate were bonded to each other using sealant with a space (4 μm) provided therebetween and then each of the liquid crystal compositions 1 to 5 stirred in an isotropic phase was injected between the substrates by an injection method.

The pixel electrode layer and the common electrode layer were formed with the use of indium tin oxide containing silicon oxide by a sputtering method. The thickness of each of the pixel electrode layer and the common electrode layer was 110 nm, the width thereof was 2 μm, and the distance between the pixel electrode layer and the common electrode layer was 2 μm. Further, an ultraviolet light and heat curable sealant was used as the sealant. As curing treatment, irradiation of ultraviolet light with an irradiance of 100 mW/cm$^2$ was performed for 90 seconds, and then, heat treatment was performed at 120° C. for an hour.

The reflectance spectra of the liquid crystal compositions 1 to 5 in the liquid crystal elements 1A to 5A were evaluated. The evaluation was performed with a polarizing microscope (MX-61L produced by Olympus Corporation), a temperature controller (HCS302-MK1000 produced by Instec, Inc.), and a microspectroscope (LVmicroUV/VIS produced by Lambda Vision Inc.).

First, the liquid crystal compositions 1 to 5 in the liquid crystal elements 1A to 5A were made to exhibit an isotropic phase. Then, the liquid crystal elements were observed with the polarizing microscope while the temperature was decreased by 1.0° C. per minute with the temperature controller. In this manner, the temperature range where the liquid crystal compositions 1 to 5 exhibit a blue phase was measured.

The measurement conditions of the observation were as follows. In the polarizing microscope, a measurement mode was a reflective mode; polarizers were in crossed nicols; and the magnification was 50 times to 200 times.

Next, each of the liquid crystal elements 1A to 5A was set at a given constant temperature within the temperature range where a blue phase was exhibited, and the spectra of the intensity of reflected light from the liquid crystal compositions 1 to 5 were measured with the microspectroscope.

The measurement conditions of the microspectroscope were as follows. A measurement mode was a reflective mode; polarizers were in crossed nicols; the measurement area was 12 μmφ; and the measurement wavelength was 250 nm to 800 nm. Since the measurement area was small, for the measurement, an area where the color of a blue phase had a long wavelength was determined with a monitor of the microspectroscope. Note that the measurement was performed from the side of the glass substrate serving as the counter substrate, over which the pixel electrode layer and the common electrode layer were not formed, in order to avoid an influence of the electrode layer and the common electrode layer in measurement.

Figure 6:
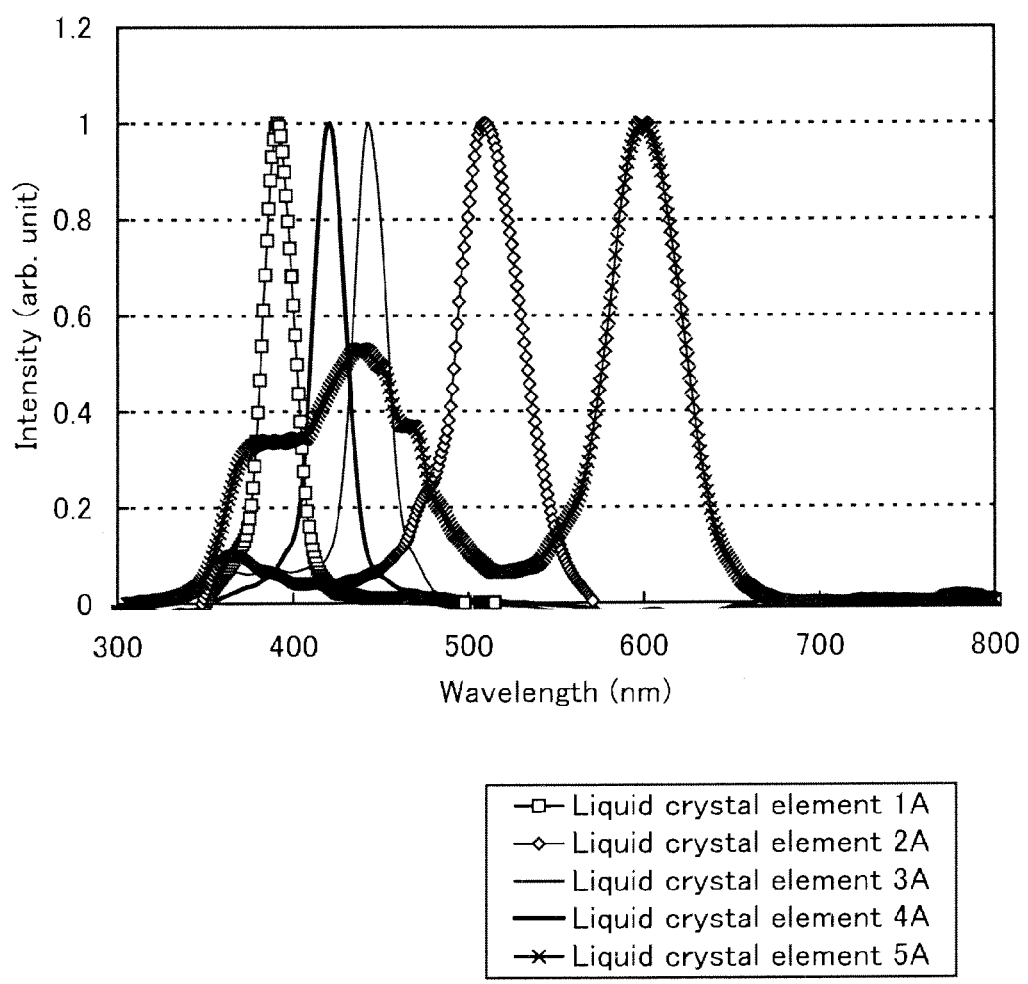
FIG. 6 shows relations between the wavelengths and the intensities of reflected light of the liquid crystal elements in Example 1.

FIG. 6 shows spectra of the intensity of reflected light from the liquid crystal compositions 1 to 5 in the liquid crystal elements 1A to 5A (quadrangular dots correspond to the liquid crystal element 1A, rhombic dots correspond to the liquid crystal element 2A, a thin solid line corresponds to the liquid crystal element 3A, a bold solid line corresponds to the liquid crystal element 4A, and x dots correspond to the liquid crystal element 5A). In the reflectance spectra of the liquid crystal compositions 1 to 5 in the liquid crystal elements 1A to 5A, peaks of the diffraction wavelengths were detected.

The peaks of the diffraction wavelengths in the reflectance spectra of the liquid crystal composition 1 in the liquid crystal element 1A, the liquid crystal composition 2 in the liquid crystal element 2A, the liquid crystal composition 3 in the liquid crystal element 3A, the liquid crystal composition 4 in the liquid crystal element 4A, and the liquid crystal composition 5 in the liquid crystal element 5A were detected at 391 nm, 510 nm, 443 nm, 421 nm, and 559 nm, respectively.

According to the above results, it was demonstrated that the liquid crystal compositions each according to one embodiment of the present invention exhibit a blue phase and the liquid crystal elements can be fabricated with the use of the liquid crystal compositions.

Example 3

In this example, liquid crystal elements each including the liquid crystal composition according to one embodiment of the present invention were made, and the characteristics of the liquid crystal elements were evaluated.

Table 4 shows components of a liquid crystal composition 6 made in this example. Note that in Table 4, the mixture proportions are all represented in weight ratios, and the proportion (wt %)$_{*1}$ indicates a proportion in liquid crystal and the proportion (wt %)$_{*2}$ indicates a proportion in a liquid crystal composition.

TABLE 4

| Components | | | Proportion (wt %)$_{*1}$ | Liquid crystal composition 6 Proportion (wt %)$_{*2}$ |
|---|---|---|---|---|
| Liquid crystal | Liquid crystal 1 | MDA-00-3506 | 50 | 93.5 |
| | Liquid crystal 2 | PPEP-5FCNF | 20 | |
| | Liquid crystal 3 | PEP-3FCNF | 30 | |
| Chiral agent | | R-DOL-Pn | | 6.5 |

$*_1$shows a proportion in a liquid crystal,
$*_2$shows a proportion in a liquid crystal composition.

A liquid crystal element 1B and liquid crystal elements 3B to 6B were fabricated with the use of the liquid crystal composition 1 and the liquid crystal compositions 3 to 6 to each of which a polymerizable monomer and a polymerization initiator are added. Table 5 shows components of the liquid crystal compositions used for the liquid crystal element 1B and the liquid crystal elements 3B to 6B.

TABLE 5

| | Liquid crystal composition | Polymerizable monomer | Polymerization initiator |
|---|---|---|---|
| Liquid crystal element 1B | Liquid crystal composition 1 | RM257-O6 DMeAc | DMPAP |
| Liquid crystal element 3B | Liquid crystal composition 3 | RM257 | |
| Liquid crystal element 4B | Liquid crystal composition 4 | RM257 | |
| Liquid crystal element 5B | Liquid crystal composition 5 | RM257-O6 | |
| Liquid crystal element 6B | Liquid crystal composition 6 | RM257-O8 Dac | |
| Proportion (wt %) | 91.8 | 4    4 | 0.2 |

As the polymerizable monomers, 1,4-bis-[4-(3-acryloyloxy-n-propyl-1-oxy)benzoyloxy]-2-methylbenzene (abbreviation: RM257) (produced by Merck Ltd., Japan), 1,4-bis-[4-(4-acryloyloxy-n-hexyl-1-oxy)benzoyloxy]-2-methylbenzene (abbreviation: RM257-O6) (produced by SHYNTHON Chemicals), 1,4-bis-[4-(8-acryloyloxy-n-octyl-1-oxy)benzoyloxy]-2-methylbenzene (abbreviation: RM257-O8), n-dodecyl methacrylate (abbreviation: DMeAc) (produced by Tokyo Chemical Industry Co., Ltd.), and n-dodecyl acrylate (abbreviation: DAc) (produced by Wako Pure Chemical Industries, Ltd.) were used. As the polymerization initiator, 2,2-dimethoxy-2-phenylacetophenone (abbreviation: DMPAP) (produced by Tokyo Chemical Industry Co., Ltd.) was used.

Note that structural formulae of PPEP-5FCNF (abbreviation), RM257 (abbreviation), RM257-O6 (abbreviation), RM257-O8 (abbreviation), DMeAc (abbreviation), DAc (abbreviation), and DMPAP (abbreviation) used in this example are shown below.

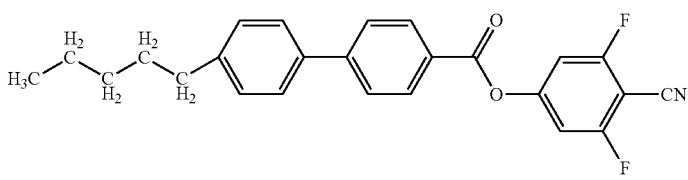

PPEP-5FCNF

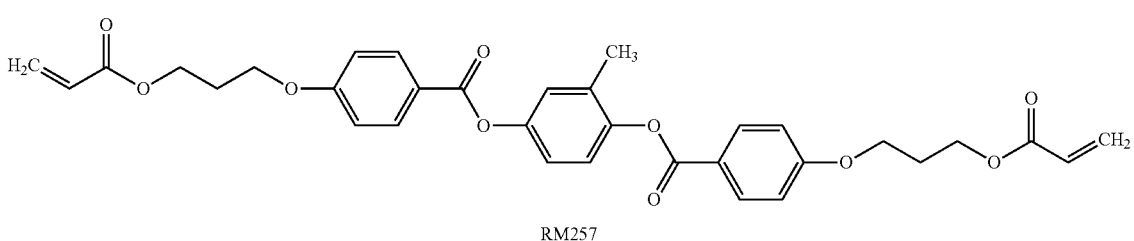

RM257

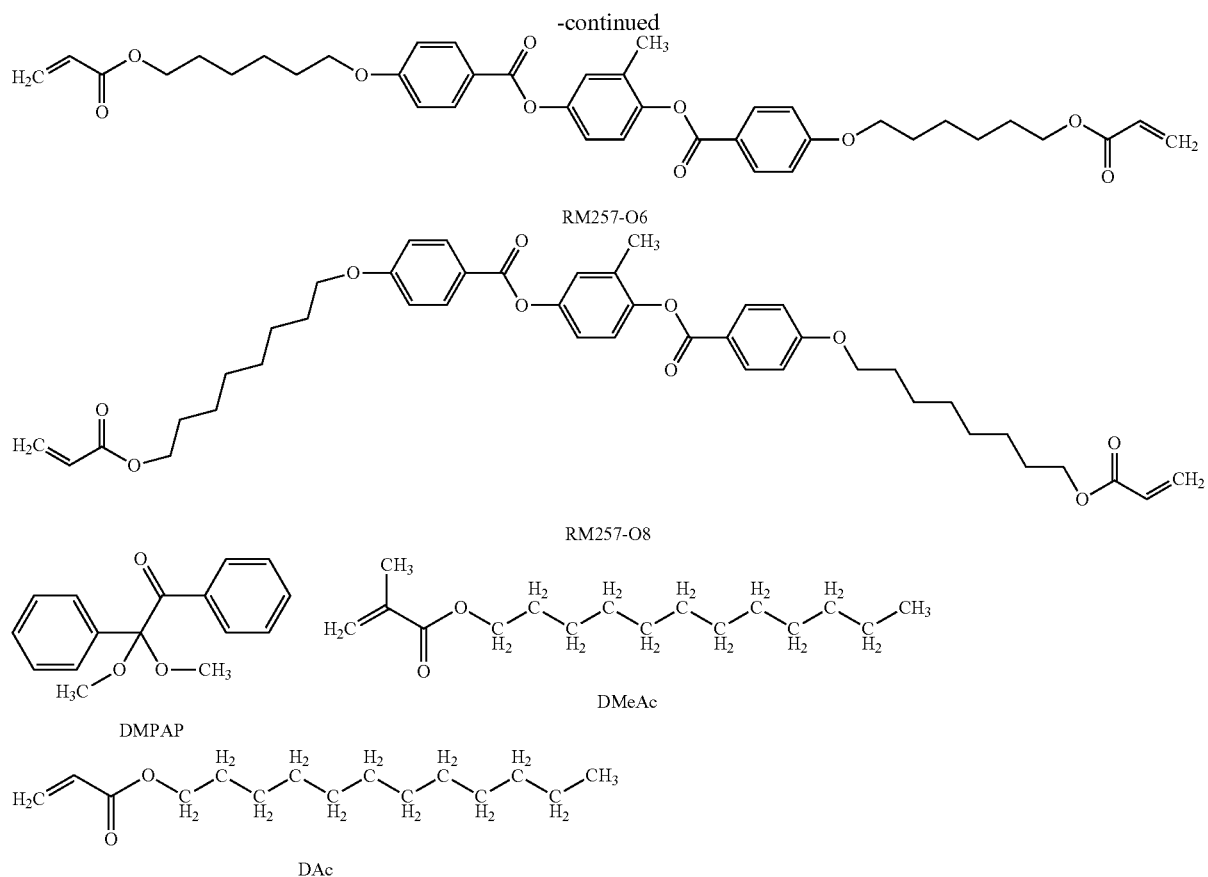

In this example, a liquid crystal element 1B, a liquid crystal element 3B, a liquid crystal element 4B, a liquid crystal element 5B, and a liquid crystal element 6B were fabricated with the use of the liquid crystal composition 1, the liquid crystal composition 3, the liquid crystal composition 4, the liquid crystal composition 5, and the liquid crystal composition 6, respectively. The fabrication method is described below.

The liquid crystal elements 1B and 3B to 6B were each fabricated in such a manner that a glass substrate over which a pixel electrode layer and a common electrode layer were formed in comb-like shapes as in FIG. 3D and a glass substrate serving as a counter substrate were bonded to each other using sealant with a space (4 μm) provided therebetween and then each of the liquid crystal compositions obtained by mixing materials in Table 4 stirred in an isotropic phase at a ratio shown in Table 4 was injected between the substrates by an injection method.

The pixel electrode layer and the common electrode layer were formed with the use of indium tin oxide containing silicon oxide by a sputtering method. The thickness of each of the pixel electrode layer and the common electrode layer was 110 nm, the width thereof was 2 μm, and the distance between the pixel electrode layer and the common electrode layer was 2 μm. Further, an ultraviolet light and heat curable sealant was used as the sealant. As curing treatment, irradiation of ultraviolet light with an irradiance of 100 mW/cm$^2$ was performed for 90 seconds, and then, heat treatment was performed at 120° C. for an hour.

Each of the liquid crystal element 1B and the liquid crystal elements 3B to 6B was set at a given constant temperature within the temperature range from the minimum temperature at which a blue phase is exhibited to a temperature higher than the maximum temperature at which a blue phase is exhibited by 1° C. to 3° C. (the maximum temperature plus 1° C. to 3° C.). As polymer stabilization treatment, irradiation with ultraviolet light (light source: Deep UV lamp, main wavelength: 365 nm, irradiance: 8 mW/cm$^2$) was performed on the liquid crystal element 1B and the liquid crystal elements 3B to 5B for six minutes and on the liquid crystal element 6B for 30 minutes. Note that polymerizable monomers contained in the liquid crystal compositions in the liquid crystal element 1B and the liquid crystal elements 3B to 5B are polymerized by the polymer stabilization treatment, so that each of the liquid crystal element 1B and the liquid crystal elements 3B to 5B becomes a liquid crystal element including a liquid crystal composition containing an organic resin.

Next, in the liquid crystal elements 1B, 3B, 4B, and 5B which had been subjected to the polymer stabilization treatment, the spectra of the intensity of reflected light from the liquid crystal compositions were measured at room temperature with the microspectroscope.

The conditions for measuring the intensity of reflected light from the liquid crystal compositions with the polarizing microscope were the same as those in Example 2.

Figure 7:
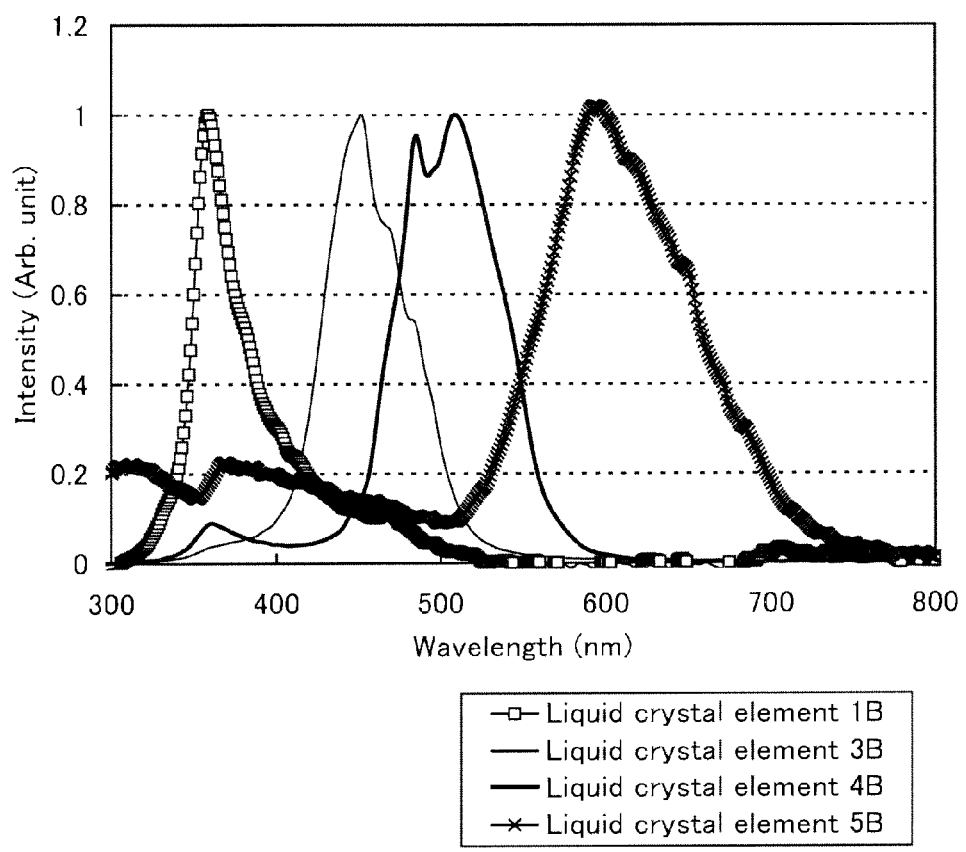
FIG. 7 shows relations between the wavelengths and the intensities of reflected light of the liquid crystal elements in Example 2.

FIG. 7 shows spectra of the intensity of reflected light from the liquid crystal compositions in the liquid crystal elements 1B, 3B, 4B, and 5B (quadrangular dots correspond to the liquid crystal element 1B, a thin solid line corresponds to the liquid crystal element 3B, a bold solid line corresponds to the liquid crystal element 4B, and x dots correspond to the liquid crystal element 5B). In the reflectance spectra of the liquid crystal compositions in the liquid crystal elements 1B, 3B, 4B, and 5B, peaks of the diffraction wavelengths on the longest wavelength side were detected.

The detected peak of the diffracted wavelength in the reflectance spectrum has the maximum value and is on the longest wavelength side among peaks. For example, although the liquid crystal element 4B has two peaks at around 486 nm and around 509 nm, the peak with the maximum value at around 509 nm on the long wavelength side was detected. Further, a peak with the maximum value is the peak of the diffracted wavelength even when the peak has a shoulder (a level difference or a low peak).

The peaks of the diffraction wavelengths on the longest wavelength side in the reflectance spectra of the liquid crystal composition in the liquid crystal element 1B, the liquid crystal composition in the liquid crystal element 3B, the liquid crystal composition in the liquid crystal element 4B, and the liquid crystal composition in the liquid crystal element 5B were detected at 359 nm, 452 nm, 509 nm, and 594 nm, respectively.

According to the above results, it was demonstrated that the liquid crystal compositions each according to one embodiment of the present invention exhibit a blue phase and the liquid crystal elements 1A, 3B, 4B, and 5B can be fabricated with the use of the liquid crystal compositions.

Next, voltage was applied to the liquid crystal elements 1B, 3B, 4B, and 6B, and characteristics of transmittance with respect to the applied voltage were evaluated. The characteristic evaluation was performed with a liquid crystal evaluation system (produced by Otsuka Electronics Co., Ltd.) under the following conditions: a halogen lamp was used as a light source, the temperature was set to room temperature, and each of the liquid crystal elements 1B, 3B, 4B, and 6B was sandwiched between polarizers in crossed nicols.

Figure 8:
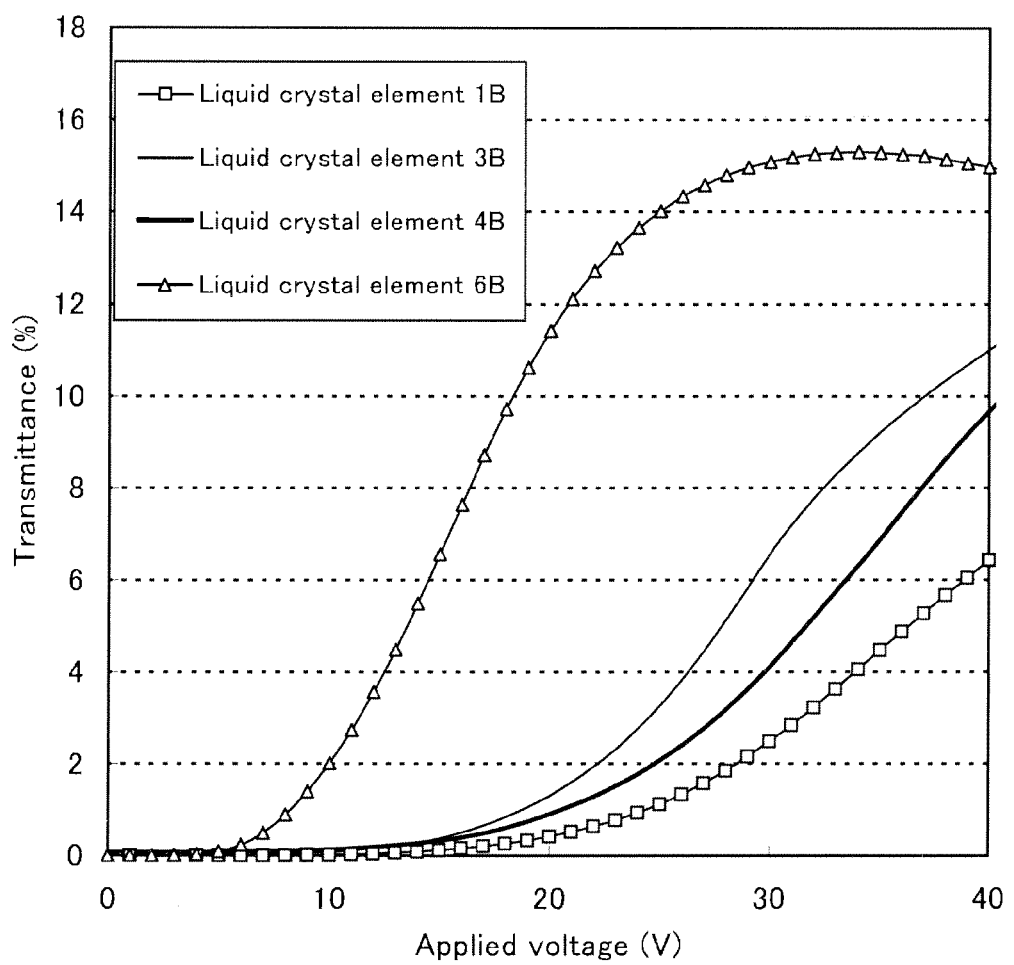
FIG. 8 shows relations between applied voltage and transmittance of the liquid crystal elements in Example 2.

FIG. 8 shows the relations between the applied voltage and the transmittance of the liquid crystal elements 1B, 3B, 4B, and 6B. The transmittance in FIG. 8 is the ratio of the intensity of light through the liquid crystal element to the intensity of light from the light source (the intensity of the light source is assumed to be 100%). Note that in FIG. 8, quadrangular dots correspond to the liquid crystal element 1B, a thin solid line corresponds to the liquid crystal element 3B, a bold solid line corresponds to the liquid crystal element 4B, and triangular dots correspond to the liquid crystal element 6B.

As shown in FIG. 8, the liquid crystal elements 1B, 3B, 4B, and 6B each have a high transmittance at low applied voltage; therefore, it was demonstrated that the liquid crystal elements 1B, 3B, 4B, and 6B can be driven at low voltage.

Since the liquid crystal elements of this example can be driven at low voltage, a reduction in power consumption of a liquid crystal display device and an electronic apparatus including the liquid crystal elements can be achieved.

Example 4

The synthesis methods of CPP-3FFF (abbreviation), PEP-5FCNF (abbreviation), PP—O3FCNF (abbreviation), PP—O5FCNF (abbreviation), PP—O8FCNF (abbreviation), CPEP-5FCNF (abbreviation), and PEP-3FCNF (abbreviation) used in Example 2 and Example 3 are described below.

Synthesis method of 4-(trans-4-n-propylcyclohexyl)-3',4',5'-trifluoro-1,1'-biphenyl (abbreviation: CPP-3FFF)

Step 1: Synthesis of trifluoromethanesulfonic acid 4-(trans-4-n-propylcyclohexyl)phenyl A synthesis scheme of trifluoromethanesulfonic acid 4-(trans-4-n-propylcyclohexyl)phenyl is shown in (E-1) below.

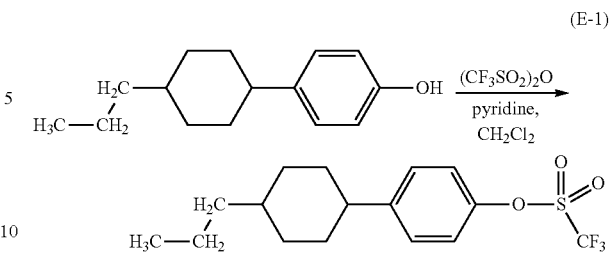

Into a 300-mL recovery flask were put 10 g (46 mmol) of 4-(trans-n-propylhexyl)phenol, 100 mL of dichloromethane, and 7.3 g (92 mmol) of pyridine, stirring was performed, and this solution was cooled to 0° C. After the cooling, a solution in which 25 g (92 mmol) of trifluoromethanesulfonic acid anhydride was dissolved in 50 mL of dichloromethane was dropped from a dropping funnel at the same temperature. After the dropping, the temperature of this solution was raised to room temperature, the solution was stirred for 15 hours at the same temperature and cooled to 0° C., and water was added to the solution slowly to inactivate part of the trifluoromethanesulfonic acid anhydride, which did not react. An aqueous layer of the obtained mixture was extracted with dichloromethane. The obtained extracted solution and an organic layer were combined, and the mixture was washed with a dilute hydrochloric acid, water, and saturated saline and then dried with magnesium sulfate. This mixture was separated by gravity filtration, and the filtrate was concentrated to give an oily substance. This oily substance was purified by silica gel column chromatography. The silica gel column chromatography was conducted using a developing solvent of toluene and hexane (toluene: hexane=1:1). The obtained fraction was concentrated to give 2.1 g of a white solid, which was a target substance, in a yield of 70%.

Step 2: Synthesis of 4-(trans-4-n-propytcyclohexyl)-3',4',5'-trifluoro-1,1'-biphenyl (abbreviation: CPP-3FFF)

A synthetic scheme of CPP-3FFF is shown in (E-2) below.

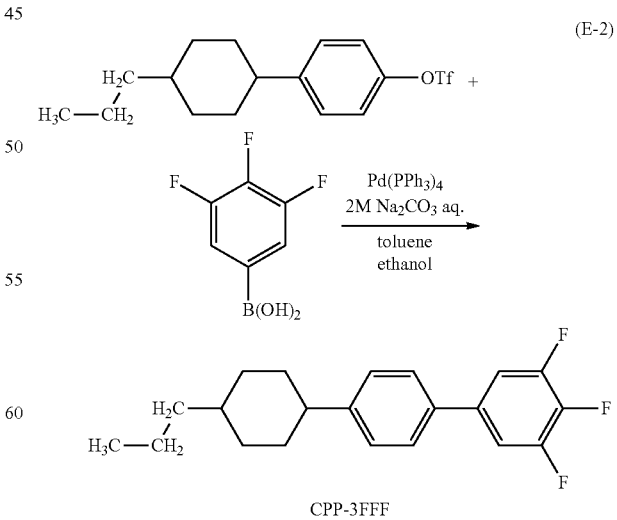

In a 100-mL, three-neck flask was put 1.7 g (9.7 mmol) of 3,4,5-trifluorophenylboronic acid, and the atmosphere in the flask was replaced with nitrogen. To the mixture were added 3.1 g (8.8 mmol) of trifluoromethanesulfonic acid 4-(trans-4-n-propylcyclohexyl)phenyl, 10 mL of 2.0M potassium carbonate solution, 34 mL of toluene, and 11 mL of ethanol, and this mixture was degassed by being stirred under reduced pressure. To the mixture was added 0.31 g (0.27 mmol) of tetrakis(triphenylphosphine)palladium(0), and this mixture was stirred at 90° C. for 3.5 hours under a nitrogen stream. After predetermined time, water was added to the obtained mixture to extract an aqueous layer with toluene. The obtained extracted solution and an organic layer were combined, washed with a saturated aqueous solution of sodium hydrogen carbonate and saturated saline, and dried with magnesium sulfate. The mixture was separated by gravity filtration, and the obtained filtrate was concentrated to give an oily substance. This oily substance was purified by silica gel column chromatography (developing solvent: hexane). The obtained fraction was concentrated to give a solid. This solid was purified by high performance liquid chromatography (HPLC) (developing solvent: chloroform). The obtained fraction was concentrated to give 2.1 g of a white solid, which was a target substance, in a yield of 70%.

Then, 1.4 g of the obtained white solid was purified by a train sublimation method. In the purification by sublimation, the white solid was heated at 100° C. under a pressure of 2.5 Pa with a flow rate of argon of 5 mL/min. After the purification by sublimation, 1.0 g of a white solid was obtained in a yield of 71%.

This compound was identified as 4-(trans-4-n-propylcyclohexyl)-3',4',5'-trifluoro-1,1'-biphenyl (abbreviation: CPP-3FFF), which was a target substance, by nuclear magnetic resonance (NMR).

The $^1$H NMR data of the obtained substance (CPP-3FFF) is shown below. $^1$H NMR (CDCl$_3$, 300 MHz): δ (ppm)=0.91 (t, 3H), 1.00-1.13 (m, 2H), 1.18-1.55 (m, 7H), 1.86-1.93 (m, 4H), 2.46-2.56 (m, 1H), 7.14-7.19 (m, 2H), 7.29 (d, 2H), 7.42 (d, 2H).

Synthesis method of 4-n-pentylbenzoic acid 4-cyano-3,5-difluorophenyl ester (abbreviation: PEP-5FCNF)

A synthesis scheme of PEP-5FCNF (abbreviation) is shown in (M-1) below.

(M-1)

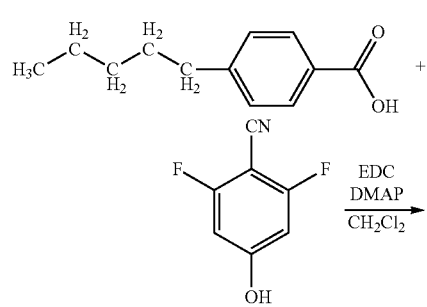

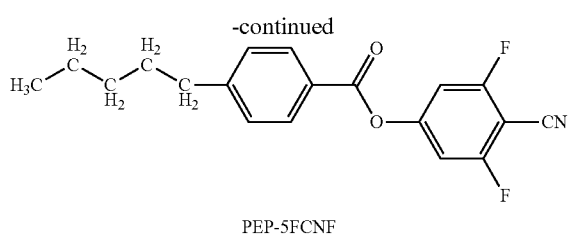

PEP-5FCNF

Into a 200-mL recovery flask were put 10 g (52 mmol) of 4-n-pentyl benzoic acid, 8.1 g (52 mmol) of 2,6-difluoro-4-hydroxybenzonitrile, 0.95 g (7.8 mmol) of 4-(N,N-dimethyl) aminopyridine (DMAP), and 52 mL of dichloromethane, and the mixture was stirred. To the mixture was added 11 g (57 mmol) of 1-ethyl-3-(3-dimethylaminopropyl) carbodiimide hydrochloride (EDC), and the resulting mixture was stirred overnight under atmospheric pressure at room temperature. After a predetermined time, water was added to the obtained mixture to extract an aqueous layer with dichloromethane. The obtained extracted solution and an organic layer were combined, washed with a saturated aqueous solution of sodium hydrogen carbonate and saturated saline, and dried with magnesium sulfate. This mixture was separated by gravity filtration, and the filtrate was concentrated to give a solid. This solid was purified by silica gel column chromatography (developing solvent: toluene) to give an oily colorless substance. This oily substance was purified by high performance liquid column chromatography (developing solvent: chloroform) to give 14 g of a white solid in a yield of 84%.

Then, 14 g of the obtained white solid was purified by a train sublimation method. In the purification by sublimation, the white solid was heated at 140° C. under a pressure of 3.0 Pa with a flow rate of argon of 5 mL/min. After the purification by sublimation, 11 g of a white solid was obtained in a yield of 79%. This white solid was identified as 4-n-pentylbenzoic acid 4-cyano-3,5-difluorophenyl ester (abbreviation: PEP-5FCNF), which was a target substance, by nuclear magnetic resonance (NMR).

$^1$H NMR data of the obtained substance is shown below.
$^1$H NMR (CDCl$_3$, 300 MHz): δ (ppm)=0.90 (t, J=6.6 Hz, 3H), 1.27-1.36 (m, 4H), 1.61-1.71 (m, 2H), 2.71 (t, J=7.2 Hz, 2H), 7.05 (dd, J1=3.0 Hz, J2=10.8 Hz, 2H), 7.34 (d, J=8.1 Hz, 2H), 8.06 (d, J=6.3 Hz, 2H).

Synthesis method of 4-(4-n-propoxyphenyl)-2,6-difluorobenzonitrile (abbreviation: PP—O3FCNF)

A synthesis scheme of PP—O3 FCNF is shown in (A-1) below.

(A-1)

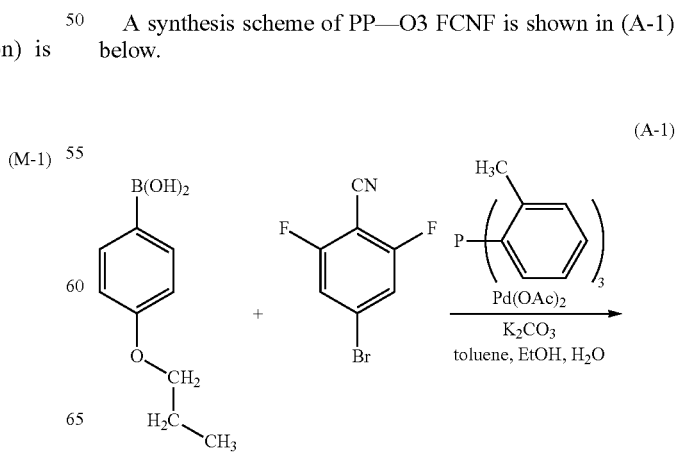

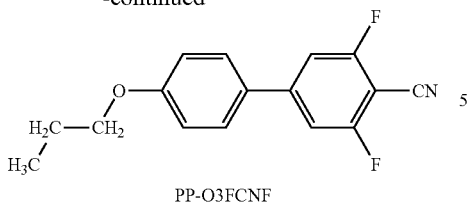

PP—O3FCNF

In a 500-mL three-neck flask were put 3.0 g (14 mmol) of 4-n-propoxyphenylboronic acid, 3.1 g (14 mmol) of 4-bromo-2,6-difluorobenzonitrile, 0.22 g (0.70 mmol) of tris(2-methylphenyl)phosphine, 30 mg (0.10 mmol) of palladium(II)acetate, and 4.0 g (29 mmol) of potassium carbonate. Into this mixture were added 54 mL of toluene, 18 mL of ethanol, and 14 mL of pure water. The obtained mixture was degassed by being stirred under reduced pressure. After the degassing, the flask was placed under a nitrogen stream, and the mixture was refluxed at 90° C. for three hours.

After the reflux, an aqueous layer of the obtained mixture was extracted with toluene. The extracted solution and the organic layer were combined, washed with saturated saline, and dried with magnesium sulfate. The mixture was gravity filtered, and the obtained filtrate was concentrated to give a light yellow solid. The obtained solid was purified by silica gel column chromatography (developing solvent: a mixed solvent of hexane: toluene=2:1) to give 2.8 g of a white solid. This solid was purified by high performance liquid column chromatography (developing solvent: chloroform) to give 2.5 g of white powder in a yield of 64%.

Then, 2.5 g of the obtained white solid was purified by a train sublimation method. In the purification by sublimation, the white solid was heated at 100° C. under a pressure of 5.5 Pa with a flow rate of argon of 15 mL/min. After the purification by sublimation, 1.9 g of white powder was obtained in a yield of 76%.

This compound was identified as 4-(4-n-propoxyphenyl)-2,6-difluorobenzonitrile (abbreviation: PP—O3FCNF) by nuclear magnetic resonance (NMR).

$^1$H NMR data of the obtained compound is shown below.

$^1$H NMR (CDCl$_3$, 300 MHz): δ=1.06 (t, J=15.0 Hz, 3H), 1.85 (m, J=3.6 Hz, 2H), 3.98 (t, J=13.2 Hz, 2H), 7.00 (d, J=2.4 Hz, 2H), 7.23 (t, J=17.4 Hz, 2H), 7.50 (d, J=2.4 Hz, 2H).

Synthesis method of
4-(4-n-pentoxyphenyl)-2,6-difluorobenzonitrile
(abbreviation: PP—O5FCNF)

A synthesis scheme of PP—O5FCNF is shown in (B-1) below.

(B-1)

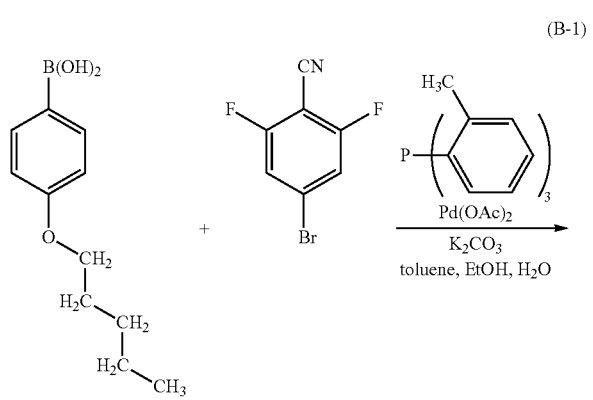

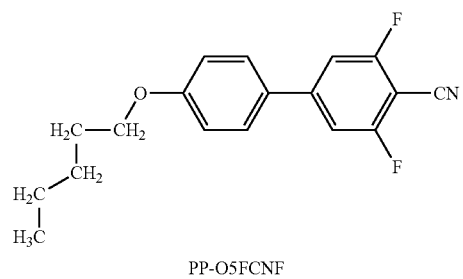

PP—O5FCNF

In a 500-mL three-neck flask were put 3.0 g (14 mmol) of 4-n-pentoxyphenylboronic acid, 3.1 g (14 mmol) of 4-bromo-2,6-difluorobenzonitrile, 0.22 g (0.70 mmol) of tris(2-methylphenyl)phosphine, 30 mg (0.10 mmol) of palladium(II) acetate, and 4.0 g (29 mmol) of potassium carbonate. Into this mixture were added 54 mL of toluene, 18 mL of ethanol, and 14 mL of pure water. While the pressure was reduced, the obtained mixture was stirred to be degassed. After the degassing, this mixture was refluxed at 90° C. for three hours.

After the reflux, an aqueous layer of the obtained mixture was extracted with toluene. The extracted solution and the organic layer were combined, washed with saturated saline, and dried with magnesium sulfate. The mixture was gravity filtered, and the obtained filtrate was concentrated to give an oily colorless substance. The oily substance was purified by silica gel column chromatography (developing solvent: a mixed solvent of hexane: toluene=5:1) to give 5.0 g of light yellow liquid.

The obtained liquid was purified by high performance liquid column chromatography (developing solvent: chloroform) to give 3.9 g of white powder.

Then, 3.9 g of the obtained white powder was purified by a train sublimation method. In the purification by sublimation, the white powder was heated at 95° C. under a pressure of 2.0 Pa with a flow rate of argon of 5 mL/min. After the purification by sublimation, 2.0 g of white powder was obtained in a yield of 46%.

This compound was identified as 4-(4-n-pentoxyphenyl)-2,6-difluorobenzonitrile (abbreviation: PP—O5FCNF) by nuclear magnetic resonance (NMR).

1H NMR data of the obtained compound is shown below.

$^1$H NMR (CDCl$_3$, 300 MHz): δ=0.89 (t, J=14.1 Hz, 3H), 1.28-1.49 (m, 4H), 1.77 (m, J=27.6 Hz, 2H), 3.96 (t, J=13.2 Hz, 2H), 6.94 (d, J=2.1 Hz, 2H), 7.18 (t, J=18.0 Hz, 2H), 7.45 (d, J=2.6 Hz, 2H).

Synthesis method of
4-(4-n-octoxyphenyl)-2,6-difluorobenzonitrile
(abbreviation: PP—O8FCNF)

A synthesis scheme of PP—O8FCNF is shown in (C-1) below.

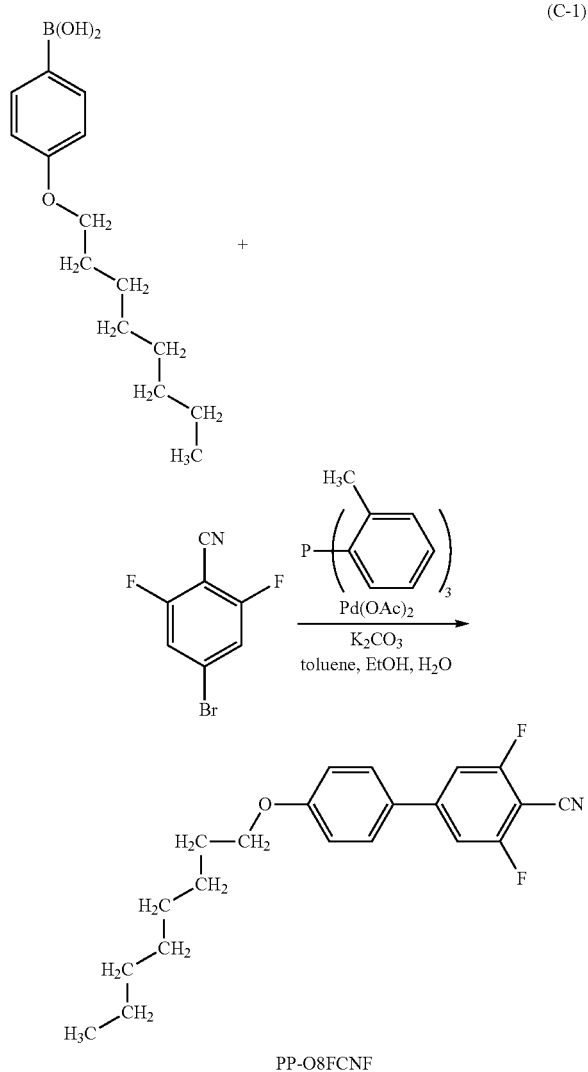

PP-O8FCNF

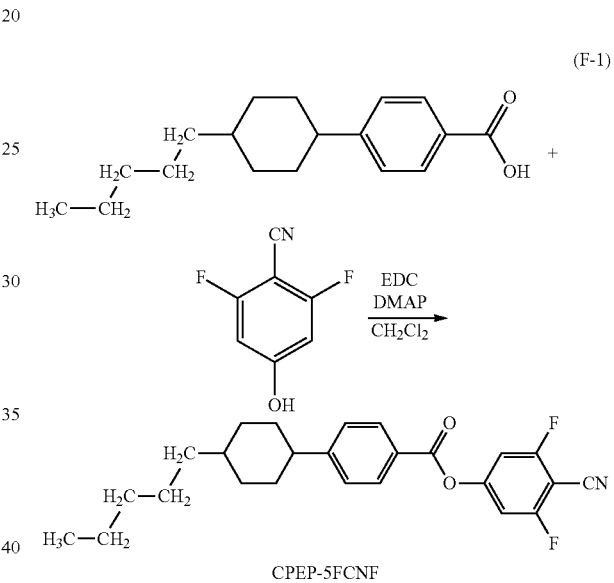

CPEP-5FCNF

In a 500-mL three-neck flask were put 3.0 g (14 mmol) of (4-n-octoxyphenyl)boronic acid, 3.1 g (14 mmol) of 4-bromo-2,6-difluorobenzonitrile, 0.22 g (0.70 mmol) of tris(2-methylphenyl)phosphine, 30 mg (0.10 mmol) of palladium(II)acetate, and 4.0 g (29 mmol) of potassium carbonate. Into this mixture were added 54 mL of toluene, 18 mL of ethanol, and 14 mL of pure water. The obtained mixture was degassed by being stirred under reduced pressure. After the degassing, this mixture was refluxed at 90° C. for three hours.

After the reflux, an aqueous layer of the obtained mixture was extracted with toluene. The extracted solution and the organic layer were combined, washed with saturated saline, and dried with magnesium sulfate. The mixture was gravity filtered, and the obtained filtrate was concentrated to give a pale red solid. The obtained solid was purified by silica gel column chromatography (developing solvent: a mixed solvent of hexane:toluene=3:1) to give 3.5 g of a white solid. The obtained white solid was purified by high performance liquid column chromatography (developing solvent: chloroform) to give 2.8 g of white powder.

Then, 2.8 g of the obtained white powder was purified by a train sublimation method. In the purification by sublimation, the white solid was heated at 110° C. under a pressure of 5.5 Pa with a flow rate of argon of 15 mL/min. After the purification by sublimation, 2.2 g of white powder was obtained in a yield of 64%.

This compound was identified as 4-(4-n-octoxyphenyl)-2,6-difluorobenzonitrile (abbreviation: PP—O8FCNF) by nuclear magnetic resonance (NMR).

$^1$H NMR data of the obtained compound is shown below.
$^1$H NMR (CDCl$_3$, 300 MHz): δ=0.89 (t, J=13.5 Hz, 3H), 1.30-1.34 (m, 8H), 1.43-1.53 (m, 2H), 1.81 (m, J=27.9 Hz, 2H), 4.01 (t, J=12.6 Hz, 2H), 7.00 (d, J=2.4 Hz, 2H), 7.23 (t, J=18.0 Hz, 2H), 7.50 (d, J=2.3 Hz, 2H).

Synthesis method of (4-(trans-4-n-pentylcyclohexyl)benzoic acid 4-cyano-3,5-difluorophenyl ester (abbreviation: CPEP-5FCNF)

A synthesis scheme of CPEP-5FCNF is shown in (F-1) below.

In a 50-ml recovery flask were put 1.9 g (6.9 nmol) of 4-(trans-4-n-pentylcyclohexyl)benzoic acid, 1.1 g (7.1 mmol) of 2,6-difluoro-4-hydroxybenzonitrile, 0.13 g (1.1 mmol) of 4-(N,N-dimethylamino)pyridine (DMAP), and 7.0 mL of dichloromethane, and the mixture was stirred. To this mixture was added 1.5 g (7.8 mmol) of 1-ethyl-3-(3-dimethylaminopropyl)carbodiimide hydrochroride (EDC), and stirred under atmospheric pressure at room temperature for 28 hours. After a predetermined time, water was added to this mixture to extract an aqueous layer with dichloromethane. The obtained extracted solution and an organic layer were combined, washed with saturated saline, and dried with magnesium sulfate. The mixture was separated by gravity filtration, and the obtained filtrate was concentrated to give a solid. This solid was purified by silica gel column chromatography (developing solvent: toluene). The obtained fraction was concentrated to give a solid. This solid was purified by high performance liquid chromatography (HPLC) (developing solvent: chloroform).

The obtained fraction was concentrated, so that 2.0 g of a white solid, which was a target substance, was obtained in a yield of 69%. Then, 2.0 g of the obtained white solid was purified by a train sublimation method. In the purification by sublimation, the white solid was heated at 155° C. under a pressure of 2.7 Pa with a flow rate of argon of 5 mL/min. After the purification by sublimation, 1.8 g of a white solid was obtained in a yield of 90%.

This compound was identified as 4-(trans-4-n-pentylcyclohexyl)benzoic acid 4-cyano-3,5-difluorophenyl ester (abbreviation: CPEP-5FCNF), which was a target substance, by nuclear magnetic resonance (NMR).

The $^1$H NMR data of the obtained substance (CPEP-5FCNF) is shown below. $^1$H NMR (CDCl$_3$, 300 MHz): δ (ppm)=0.90 (t, 3H), 1.02-1.13 (m, 2H), 1.20-1.35 (m, 9H), 1.43-1.54 (m, 2H), 1.89-1.93 (m, 4H), 2.54-2.62 (m, 1H), 7.05 (d, 2H), 7.37 (d, 2H), 8.06 (d, 2H).

Synthesis method of 4-n-propylbenzoic acid 4-cyano-3,5-difluorophenyl ester (abbreviation: PEP-3FCNF)

A synthesis scheme of 4-n-propylbenzoic acid 4-cyano-3,5-difluorophenyl ester (abbreviation: PEP-3FCNF) is shown in (G-1) below.

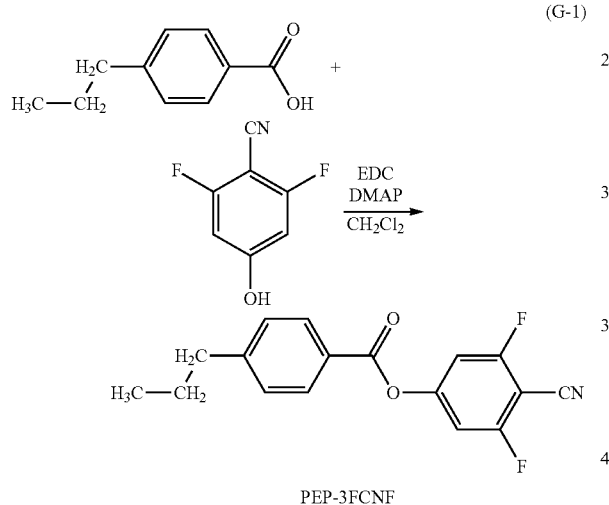

PEP-3FCNF

In a 50-mL recovery flask were put 1.6 g (10 mmol) of 4-n-propylbenzoic acid, 1.6 g (10 mmol) of 2,6-difluoro-4-hydroxybenzonitrile, 0.19 g (1.5 mmol) of (4-N,N-dimethylamino)pyridine, and 10 mL of dichloromethane, and the mixture was stirred. To this mixture was added 2.1 g (11 mmol) of 1-ethyl-3-(3-dimethylaminopropyl)carbodiimide hydrochroride (EDC), and was stirred under atmospheric pressure at room temperature for 15 hours. After a predetermined time, water was added to the obtained mixture to extract an aqueous layer of this mixture with dichloromethane. The obtained extracted solution and an organic layer were combined, washed with a saturated aqueous solution of sodium hydrogen carbonate and saturated saline, and dried with magnesium sulfate. This mixture was separated by gravity filtration, and the filtrate was concentrated to give a white solid. This solid was purified by silica gel column chromatography (developing solvent: toluene). The resulting fraction was concentrated to give a white solid. This solid was purified by high performance liquid chromatography (HPLC) (developing solvent: chloroform). The obtained fraction was concentrated to give 2.4 g of a white solid, which was a target substance, in a yield of 79%.

Then, 2.4 g of the obtained white solid was purified by a train sublimation method. In the purification by sublimation, the white solid was heated at 130° C. under a pressure of 2.1 Pa with a flow rate of argon of 10 mL/min. After the purification by sublimation, 1.3 g of a white solid was obtained in a yield of 42%.

This compound was identified as 4-n-propylbenzoic acid 4-cyano-3,5-difluorophenyl ester (abbreviation: PEP-3FCNF), which was a target substance, by nuclear magnetic resonance (NMR).

The $^1$H NMR data of the obtained substance (PEP-3FCNF) is shown below. $^1$H NMR (CDCl$_3$, 300 MHz): δ (ppm)=0.97 (t, 3H), 1.63-1.76 (m, 2H), 2.70 (t, 2H), 7.05 (d, 2H), 7.34 (d, 2H), 8.06 (d, 2H).

Synthesis method of 4-(4-n-pentylphenyl)benzoic acid 4-cyano-3,5-difluorophenyl (abbreviation: PPEP-5FCNF)

A synthesis scheme of PPEP-5FCNF (abbreviation) is shown in (N-1) below.

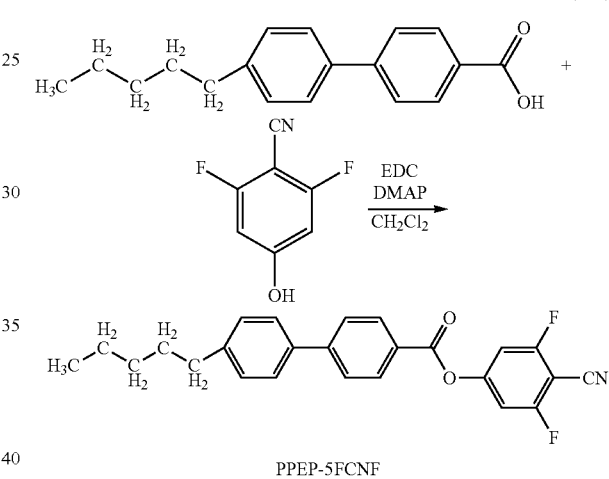

PPEP-5FCNF

In a 50-mL recovery flask were put 2.3 g (8.6 mmol) of 4-(4-n-pentylphenyl)benzoic acid, 1.3 g (8.4 mmol) of 2,6-difluoro-4-hydroxybenzonitrile, 0.16 g (1.3 mmol) of 4-dimethylaminopyridine, and 8.6 mL of dichloromethane, and the mixture was stirred. To the mixture was put 1.8 g (9.4 mmol) of 1-ethyl-3-(3-dimethylaminopropyl) carbodiimide hydrochloride (EDC), and the resulting mixture was stirred under atmospheric pressure at room temperature for 18 hours. After a predetermined time, water was added to the obtained mixture to extract an aqueous layer with dichloromethane. The obtained extracted solution and an organic layer were combined, washed with a saturated aqueous solution of sodium hydrogen carbonate and saturated saline, and dried with magnesium sulfate. The mixture was separated by gravity filtration, and the obtained filtrate was concentrated to give a light brown solid. This solid was purified by silica gel column chromatography (developing solvent: toluene). The resulting fraction was concentrated to give a white solid. This solid was purified by high performance liquid chromatography (HPLC) (developing solvent: chloroform). The obtained fraction was concentrated to give 2.7 g of a white solid, which was a target substance, in a yield of 79%.

Then, 2.7 g of the obtained white solid was purified by distillation, so that 2.5 g of a white solid, which was a target substance, was obtained in a yield of 93%.

This compound was identified as 4-(4-n-pentylphenyl)benzoic acid 4-cyano-3,5-difluorophenyl (PPEP-5FCNF), which was a target substance, by a nuclear magnetic resonance (NMR).

$^1$H NMR data of the obtained substance is shown below.

$^1$H NMR (CDCl$_3$, 300 MHz): δ (ppm)=0.91 (t, 3H), 1.31-1.40 (m, 4H), 1.62-1.72 (m, 2H), 2.67 (t, 2H), 7.09 (d, 2H), 7.31 (d, 2H), 7.58 (d, 2H), 7.75 (d, 2H), 8.20 (d, 2H).

Synthesis method of 1,4-bis-[4-(8-acryloyloxy-n-octyl-1-oxy)benzoyloxy]-2-methylbenzene (abbreviation: RM257-O8)

A synthesis scheme of RM257-O8 (abbreviation) is shown in (N-1) below.

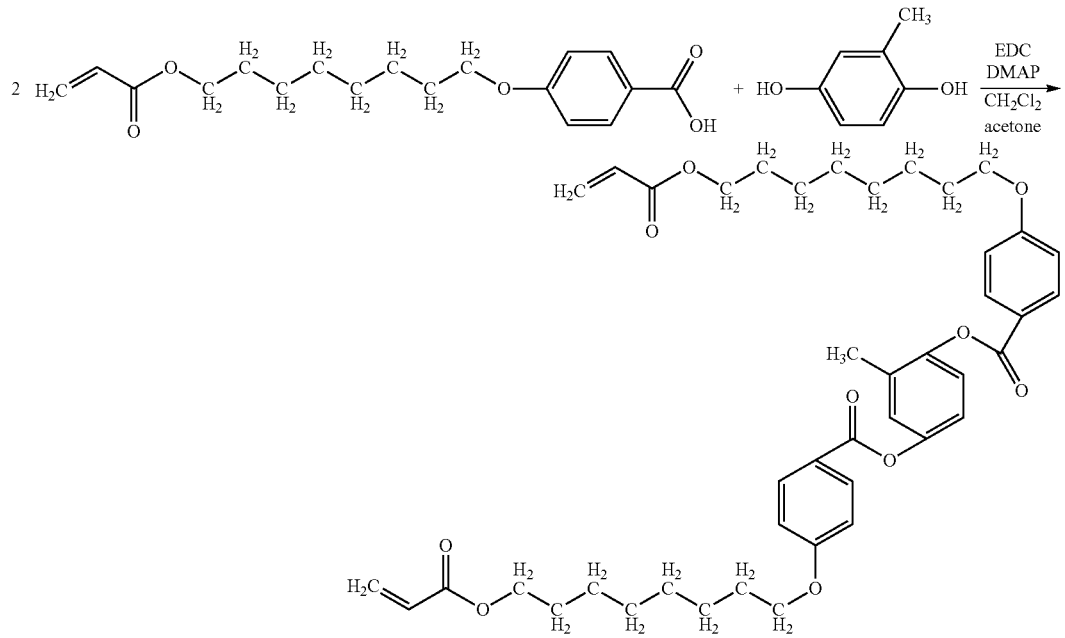

In a 300-mL recovery flask were put 3.0 g (9.4 mmol) of 4-(8-acryloyloxy-n-octyl-1-oxy)benzoic acid, 0.47 g (3.8 mmol) of 2-methyl-1,4-benzenediol, 0.17 g (1.4 mmol) of 4-dimethylaminopyridine (DMAP), 1.8 g (9.4 mmol) of 1-ethyl-3-(3-dimethylaminopropyl)carbodiimide hydrochloride (EDC), 100 mL of acetone, and 50 mL of dichloromethane, and the mixture was stirred under atmospheric pressure at room temperature for 23 hours. After a predetermined time, the mixture was concentrated and water was added to the mixture, and an aqueous layer was extracted with chloroform. The obtained extracted solution and an organic layer were combined, washed with water, a saturated aqueous solution of sodium hydrogen carbonate, and saturated saline, and the organic layer, and dried with magnesium sulfate. This mixture was separated by gravity filtration, and the filtrate was concentrated to give a solid. The obtained solid was purified by silica gel column chromatography (developing solvent: chloroform). The resulting fraction was concentrated to give a white solid. The obtained white solid was purified by high performance liquid chromatography (HPLC) (developing solvent: chloroform) to give 0.92 g of a white solid, which was a target substance, in a yield of 34%.

$^1$H NMR data of the obtained substance is shown below.

$^1$H NMR (CDCl$_3$, 300 MHz): δ (ppm)=1.39-1.54 (m, 16H), 1.67-1.85 (m, 8H), 2.24 (s, 3H), 4.05 (t, J=5.9 Hz, 4H), 4.16 (t, J=6.6 Hz, 4H), 5.82 (dd, J1=10.2 Hz, J2=1.5 Hz, 2H), 6.13 (dd, J1=10.5 Hz, J2=17.4 Hz, 2H), 6.41 (dd, J1=1.5 Hz, J2=17.1 Hz, 2H), 6.98 (dd, J1=3.9 Hz, J2=8.7 Hz, 4H), 7.09-7.19 (m, 3H), 8.15 (d, J=8.3 Hz, 4H).

Example 5

This example shows an example for synthesizing (R)(R)-4,5-bis[hexyloxy(diphenanthryl)methyl]-2,2'-dimethyl-1,3-dioxolane (abbreviation: R-DOL-Pn-O6), which is a dioxolane compound represented by the structural formula (115) in Embodiment 1.

In a 50-mL recovery flask were put 0.50 g (0.58 mmol) of (R)(R)-4,5-bis[hydroxy(diphenanthryl)methyl]-2,2'-dimethyl-1,3-dioxolane, which is made by the synthesis scheme (L-1) in Example 1, 0.21 g (1.3 mmol) of 1-bromohexane, 0.18 g (1.3 mmol) of potassium carbonate, and 5.0 mL of cyclohexanone, and the mixture was stirred under a nitrogen stream at 140° C. for seven hours. After a predetermined time, water was added to the obtained mixture to extract an aqueous layer of the mixture with toluene. The obtained extract solution and an organic layer were combined, washed with water and saturated saline, and dried with magnesium sulfate. This mixture was separated by gravity filtration, and the filtrate was concentrated to give a colorless oily substance.

This oily substance was purified by silica gel column chromatography (developing solvent: toluene). The obtained fraction was concentrated to give a colorless oily substance. This oily substance was purified by high performance liquid column chromatography (HPLC) (developing solvent: chloroform).

The obtained fraction was concentrated to give a white solid. To this solid was added hexane, followed by irradiation with ultrasonic waves. The precipitated solid was collected by suction filtration to give 0.3 g of a white solid, which was a target substance, in a yield of 50%. The above-described synthesis scheme is shown below.

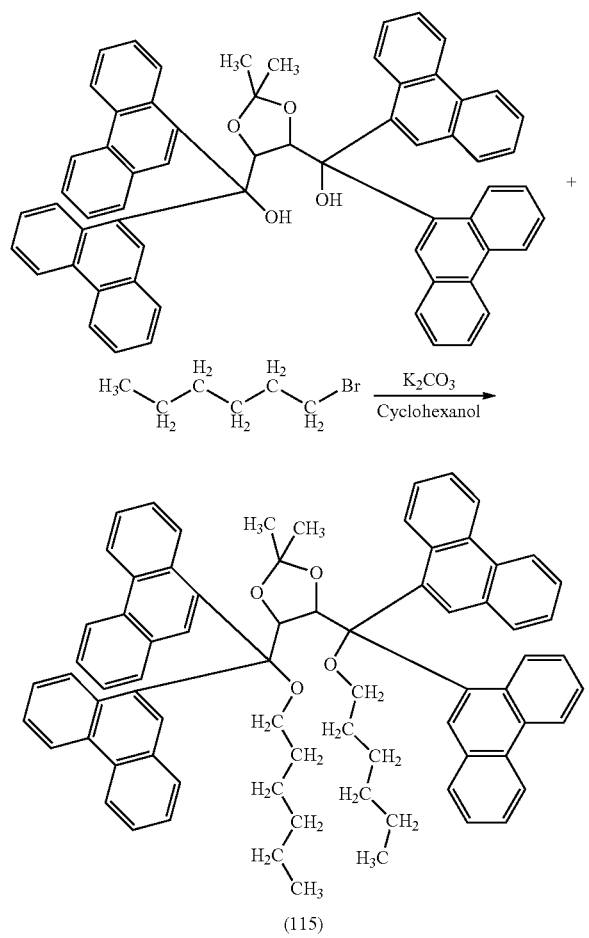

(115)

This compound was identified as (R)(R)-4,5-bis[hexyloxy (diphenanthryl)methyl]-2,2'-dimethyl-1,3-dioxolane (abbreviation: R-DOL-Pn-O6) by nuclear magnetic resonance (NMR).

Furthermore, an absorption spectrum of R-DOL-Pn-O6 in a dichloromethane solution was measured, and absorption was observed at around 302 nm, 291 nm, 256 nm, and 226 nm.

EXPLANATION OF REFERENCE

200: first substrate, 201: second substrate, 202a: alignment film, 202b: alignment film, 208: liquid crystal composition, 230: pixel electrode layer, 232: common electrode layer, 401: gate electrode layer, 402: gate insulating layer, 403: semiconductor layer, 405a: wiring layer, 405b: wiring layer, 407: insulating film, 408: common wiring layer, 409: insulating film, 413: interlayer film, 420: transistor, 441: first substrate, 442: second substrate, 443a: polarizing plate, 443b: polarizing plate, 444: liquid crystal composition, 446: second electrode layer, 446a: second electrode layer, 446b: second electrode layer, 446c: second electrode layer, 446d: second electrode layer, 447: first electrode layer, 447a: first electrode layer, 447b: first electrode layer, 447c: first electrode layer, 447d: first electrode layer, 2701: housing, 2703: housing, 2705: display portion, 2707: display portion, 2711: axis portion, 2721: power supply, 2723: operation key, 2725: speaker, 2800: housing, 2801: housing, 2802: display panel, 2803: speaker, 2804: microphone, 2805: operation key, 2806: pointing device, 2807: camera lens, 2808: external connection terminal, 2810: solar cell, 2811: external memory slot, 3001: main body, 3002: housing, 3003: display portion, 3004: keyboard, 3021: main body, 3022: stylus, 3023: display portion, 3024: operation button, 3025: external interface, 3051: main body, 3053: eyepiece portion, 3054: operation switch, 3056: battery, 4001: first substrate, 4002: pixel portion, 4003: signal line driver circuit, 4003a: signal line driver circuit, 4003b: signal line driver circuit, 4004: scan line driver circuit, 4005: sealing material, 4006: second substrate, 4008: liquid crystal composition, 4010: transistor, 4011: transistor, 4013: liquid crystal element, 4015: connection terminal electrode, 4016: terminal electrode, 4018: FPC, 4019: anisotropic conductive film, 4020: insulating layer, 4021: interlayer film, 4030: pixel electrode layer, 4031: common electrode layer, 4032a: polarizing plate, 4032b: polarizing plate, 4034: light-blocking layer, 9601: housing, 9603: display portion, 9605: stand This application is based on Japanese Patent Application serial no. 2011-161329 filed with Japan Patent Office on Jul. 22, 2011, the entire contents of which are hereby incorporated by reference.

The invention claimed is:
1. A liquid crystal composition comprising:
an organic resin;
a nematic liquid crystal; and
a dioxolane compound represented by a general formula (G1),

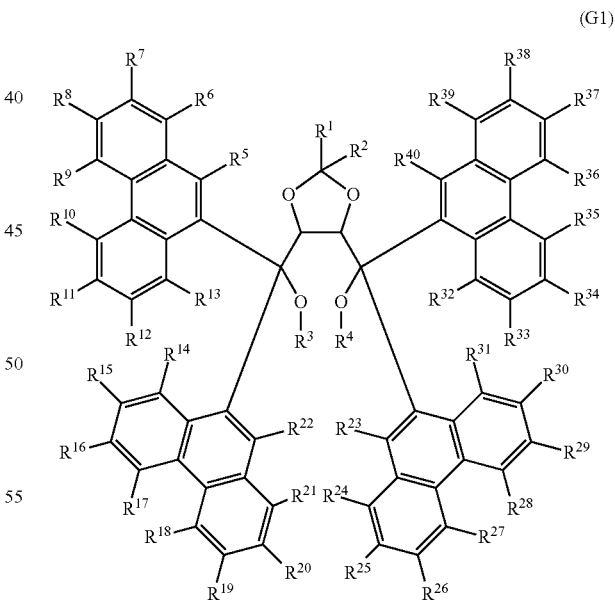

(G1)

wherein in the general formula (G1):
$R^1$ and $R^2$ individually represent any of hydrogen, an alkyl group having 1 to 6 carbon atoms, an alkoxy group having 1 to 20 carbon atoms, an aryl group having 6 to 12 carbon atoms, and an alkyl group having 1 to 20 carbon atoms and having a phenyl group as a substituent or are bonded to each other to form a ring;

R$^3$ and R$^4$ individually represent any of hydrogen, an alkyl group having 1 to 6 carbon atoms, and a cycloalkyl group; and R$^5$ to R$^{40}$ individually represent any of hydrogen, an alkyl group having 1 to 4 carbon atoms, an alkoxy group having 1 to 4 carbon atoms, and an aryl group having 6 to 12 carbon atoms.

2. The liquid crystal composition according to claim 1, wherein the liquid crystal composition exhibits a blue phase.

3. The liquid crystal composition according to claim 1, wherein a proportion of the dioxolane compound in the liquid crystal composition is lower than or equal to 7 wt %.

4. The liquid crystal composition according to claim 1, wherein a peak of a diffraction wavelength on the longest wavelength side in a reflectance spectrum is less than or equal to 700 nm.

5. The liquid crystal composition according to claim 1, wherein a peak of a diffraction wavelength on the longest wavelength side in a reflectance spectrum is less than or equal to 420 nm.

6. A liquid crystal element comprising the liquid crystal composition according to claim 1.

7. A liquid crystal display device comprising the liquid crystal composition according to claim 1.

8. A liquid crystal composition comprising:
a nematic liquid crystal; and
a dioxolane compound represented by a general formula (G2),

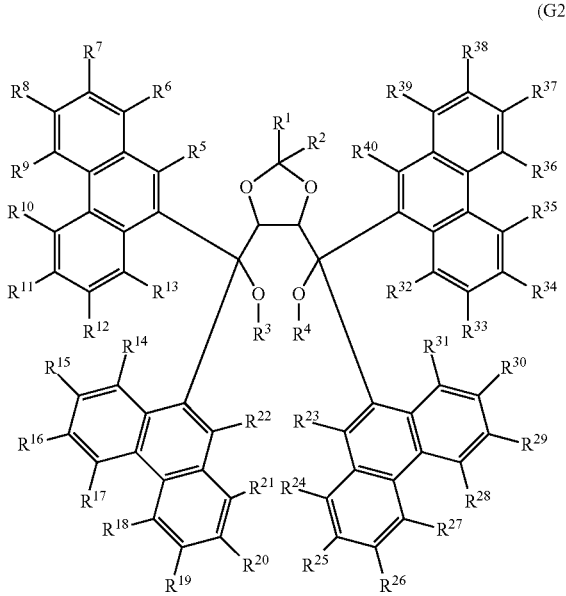

(G2)

wherein in the general formula (G2):
R$^1$ and R$^2$ individually represent any of hydrogen, an alkyl group having 1 to 6 carbon atoms, a methoxy group, and a phenyl group or are bonded to each other to form a cyclohexyl ring; and R$^3$ and R$^4$ individually represent an alkyl group having 1 to 6 carbon atoms or a cycloalkyl group; and R$^5$ to R$^{40}$ individually represent hydrogen.

9. The liquid crystal composition according to claim 8, wherein the liquid crystal composition exhibits a blue phase.

10. The liquid crystal composition according to claim 8, wherein a proportion of the dioxolane compound in the liquid crystal composition is lower than or equal to 7 wt %.

11. The liquid crystal composition according to claim 8, wherein a peak of a diffraction wavelength on the longest wavelength side in a reflectance spectrum is less than or equal to 700 nm.

12. The liquid crystal composition according to claim 8, wherein a peak of a diffraction wavelength on the longest wavelength side in a reflectance spectrum is less than or equal to 420 nm.

13. A liquid crystal element comprising the liquid crystal composition according to claim 8.

14. A liquid crystal display device comprising the liquid crystal composition according to claim 8.

15. The liquid crystal element according to claim 13, wherein the liquid crystal composition includes an organic resin.

16. The liquid crystal display device according to claim 14, wherein the liquid crystal composition includes an organic resin.

17. A liquid crystal composition comprising:
an organic resin:
a dioxolane compound represented by a structural formula (101); and

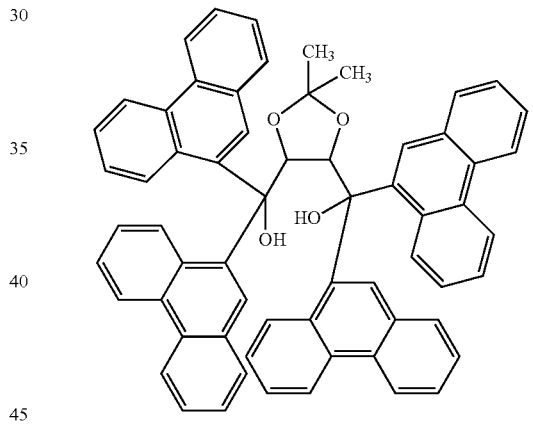

(101)

a nematic liquid crystal.

18. The liquid crystal composition according to claim 17, wherein the liquid crystal composition exhibits a blue phase.

19. The liquid crystal composition according to claim 17, wherein a proportion of the dioxolane compound in the liquid crystal composition is lower than or equal to 7 wt %.

20. The liquid crystal composition according to claim 17, wherein a peak of a diffraction wavelength on the longest wavelength side in a reflectance spectrum is less than or equal to 700 nm.

21. The liquid crystal composition according to claim 17, wherein a peak of a diffraction wavelength on the longest wavelength side in a reflectance spectrum is less than or equal to 420 nm.

22. A liquid crystal element comprising the liquid crystal composition according to claim 17.

23. A liquid crystal display device comprising the liquid crystal composition according to claim 17.

24. The liquid crystal composition according to claim 8, wherein the dioxolane compound is represented by a structural formula (115);
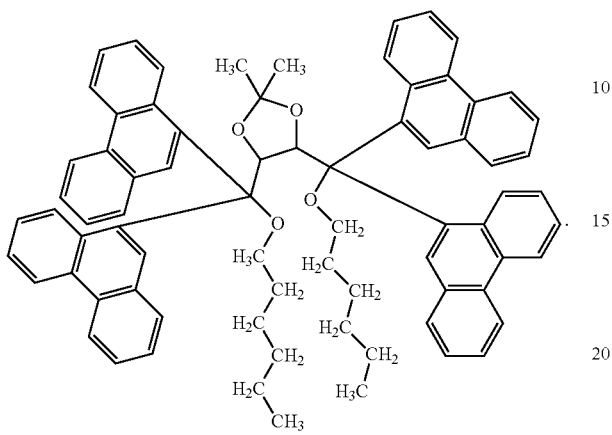
(115)
* * * * *

UNITED STATES PATENT AND TRADEMARK OFFICE
CERTIFICATE OF CORRECTION

PATENT NO. : 8,642,141 B2
APPLICATION NO. : 13/543695
DATED : February 4, 2014
INVENTOR(S) : Tomohiro Tamura et al.

It is certified that error appears in the above-identified patent and that said Letters Patent is hereby corrected as shown below:

In the Specification:

Column 16, line 44; change "Compound l" to "Compound 1"

Column 27, line 66; change "hafinium" to "hafnium"

Column 31, line 58; change "40111" to "4011"

Column 36, line 41; change "diphenanthrvyl" to "diphenanthryl"

Column 37, line 23; change "0.5 mL, of" to "0.5 mL of"

Column 37, line 26; change "in 50 ml" to "in 50 mL"

Column 48, line 37; change "propytcyclohexyl" to "propylcyclohexyl"

Column 48, line 66; change "100-mL, three-neck flask" to "100-mL three-neck flask"

Column 54, line 44; change "50-ml recovery flask" to "50-mL recovery flask"

Column 54, line 44; change "6.9 nmol" to "6.9 mmol"

Table 1 delete " [Table 1 image with proportion data] "

Signed and Sealed this
Ninth Day of September, 2014

Michelle K. Lee
*Deputy Director of the United States Patent and Trademark Office* insert --

| Components | | Proportion (wt%)*1 | Liquid crystal composition 1 Proportion (wt%)*2 | Liquid crystal composition 2 Proportion (wt%)*2 |
|---|---|---|---|---|
| Liquid crystal | Liquid crystal 1 MDA-00-3506 | 30 | 94.32 | 96.03 |
| | Liquid crystal 2 NEDO LC-C | 20 | | |
| | Liquid crystal 3 CPP-3FFF | 20 | | |
| | Liquid crystal 4 PEP-5FCNF | 30 | | |
| Chiral agent | R-DOL-Pn | | 5.68 | 3.97 |

*1 shows a proportion in a liquid crystal, *2 shows a proportion in a liquid crystal composition.

--

Table 2

TABLE 2

| Components | | Proportion (wt%)*1 | Liquid crystal composition 3 Proportion (wt%)*2 | Liquid crystal composition 4 Proportion (wt%)*2 |
|---|---|---|---|---|
| Liquid crystal | Liquid crystal 1 E-8 | 40 | 96.25 | 95.65 |
| | Liquid crystal 2 CPP-3FF | 30 | | |
| | Liquid crystal 3 PEP-5CNF | 30 | | |
| Chiral agent | R-DOL-Pn | | 4.75 | 4.35 | delete "*1 shows a proportion in a liquid crystal. *2 shows a proportion in a liquid crystal composition."

insert --

| Components | | Proportion (wt%)*1 | Liquid crystal composition 3 Proportion (wt%)*2 | Liquid crystal composition 4 Proportion (wt%)*2 |
|---|---|---|---|---|
| Liquid crystal | Liquid crystal 1 E-8 | 40 | 96.25 | 95.65 |
| | Liquid crystal 2 CPP-3FF | 30 | | |
| | Liquid crystal 3 PEP-5CNF | 30 | | |
| Chiral agent | R-DOL-Pn | | 4.75 | 4.35 |

*1 shows a proportion in a liquid crystal, *2 shows a proportion in a liquid crystal composition.

--

Table 3 delete " *shows a proportion in a liquid crystal.*
*shows a proportion in a liquid crystal composition.* "

insert --

| Components | | | Proportion (wt%)*1 | Liquid crystal composition 5 Proportion (wt%)*2 |
|---|---|---|---|---|
| Liquid crystal | Liquid crystal 1 | PEP-5FCNF | 18 | 97.01 |
| | Liquid crystal 2 | 5CT | 4.4 | |
| | Liquid crystal 3 | PP-O3FCNF | 6.4 | |
| | Liquid crystal 4 | PP-O5FCNF | 4.8 | |
| | Liquid crystal 5 | PP-O8FCNF | 6.4 | |
| | Liquid crystal 6 | CPEP-5FCNF | 30 | |
| | Liquid crystal 7 | PEP-3FCNF | 30 | |
| Chiral agent | | R-DOL-Pn | | 2.99 |

*1 shows a proportion in a liquid crystal. *2 shows a proportion in a liquid crystal composition. --

Table 4 delete " *shows a proportion in a liquid crystal.*
*shows a proportion in a liquid crystal composition.* "

CERTIFICATE OF CORRECTION (continued)

U.S. Pat. No. 8,642,141 B2

| Components | | | Proportion (wt%)*1 | Liquid crystal composition 6 |
|---|---|---|---|---|
| | | | | Proportion (wt%)*2 |
| Liquid crystal | Liquid crystal 1 | MDA-00-3506 | 50 | 93.5 |
| | Liquid crystal 2 | PPEP-5FCNF | 20 | |
| | Liquid crystal 3 | PEP-3FCNF | 30 | |
| Chiral agent | | R-DOL-Pn | | 6.5 | and insert -- *1 shows a proportion in a liquid crystal , *2 shows a proportion in a liquid crystal composition. --

Table 5 delete "

TABLE 5

| | Liquid crystal composition | Polymerizable monomer | Polymerization initiator |
|---|---|---|---|
| Liquid crystal element 1B | Liquid crystal composition 1 | RM257-O6 | DMeAc | DMPAP |
| Liquid crystal element 3B | Liquid crystal composition 3 | RM257 | | |
| Liquid crystal element 4B | Liquid crystal composition 4 | RM257 | | |
| Liquid crystal element 5B | Liquid crystal composition 5 | RM257-O6 | | |
| Liquid crystal element 6B | Liquid crystal composition 6 | RM257-O8 | Dac | |
| Proportion (wt %) | 91.8 | 4 | 4 | 0.2 |

"

| | Liquid crystal composition | Polymerizable monomer | Polymerization initiator | |
|---|---|---|---|---|
| Liquid crystal element 1B | Liquid crystal composition 1 | RM257-O6 | DMeAc | DMPAP |
| Liquid crystal element 3B | Liquid crystal composition 3 | RM257 | | |
| Liquid crystal element 4B | Liquid crystal composition 4 | RM257 | | |
| Liquid crystal element 5B | Liquid crystal composition 5 | RM257-O6 | | |
| Liquid crystal element 6B | Liquid crystal composition 6 | RM257-O8 | Dac | |
| Proportion (wt%) | 91.8 | 4 | 4 | 0.2 | and insert -- --

In the Claims:

Claim 17, Column 62, line 26; change "resin:" to "resin;"